US007607338B1

(12) United States Patent
Lewis et al.

(10) Patent No.: US 7,607,338 B1
(45) Date of Patent: Oct. 27, 2009

(54) HANDHELD INSTRUMENT FOR MONITORING AND/OR IDENTIFICATION OF CHEMICALS

(75) Inventors: Wallace J. Lewis, Tifton, GA (US); Glen C. Rains, Tifton, GA (US); Samuel L. Utley, Tifton, GA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 11/185,109

(22) Filed: Jul. 20, 2005

Related U.S. Application Data

(60) Provisional application No. 60/592,737, filed on Jul. 30, 2004.

(51) Int. Cl.
*G01N 19/10* (2006.01)
(52) U.S. Cl. ............... 73/31.02; 73/31.01; 73/23.2
(58) Field of Classification Search .................. None
See application file for complete search history.

(56) References Cited

U.S. PATENT DOCUMENTS

| 6,919,202 | B2 * | 7/2005 | Lewis et al. | 435/287.1 |
| 7,036,454 | B2 * | 5/2006 | Davis et al. | 119/6.5 |
| 7,237,504 | B2 * | 7/2007 | Davis et al. | 119/6.5 |
| 2004/0101851 | A1 * | 5/2004 | White et al. | 435/6 |

OTHER PUBLICATIONS

MacDonald, Jacqueline. Alternatives for Landmine Detection. Santa Monica CA. Random House, 2003. Appendix S: Bromenshenck, Jerry "Biological Systems". University of Montana.*
Library of Congress Catalog Record for MacDonald, Jacqueline, Alternatives for Landmine Detection. Indexing Date 2002.*
Sudduth, K.A., et al., "Sensors for Site-Specific Management", pp. 183-210. In Perce, F.J., and Sadler, E.J. (Eds.) The State of Site Specific Management for Agriculture. Amer. Soc. Agri. Inc., Madison, WI., 1997.
Gould, J.L., "Natural History of Honey Bee Learning", pp. 149-180, Dept. of Biology, Princeton University, Princeton, NJ 08544, USA.
Bitterman, M.E., et al., "Classical Conditioning of Proboscis Extension in Honeybees (Apis mellifera)", *Journal of Comparative Psychology*, vol. 97(2), pp. 107-119, 1983.
Turlings, T.C.J.,et al., "Learning of Host-Findings Cues by Hymenopterous Parasitoids", pp. 51-78. In Papaj, D.R., and Lewis, A.C. (Eds.), Insect Learning. Ecological and Evolutionary Perspectives. Chapman & Hall, New York.
Lewis, W.J., et al., "Host Detection by Chemically Mediated Associative Learning in a Parasitic Wasp", *Nature*, vol. 331, pp. 257-259, 1988.
Menzel, R., et al., "Biology of Invertebrate Learning", In. Marler, P., and Terrace, H.S., (Eds.), The Biology of Learning. Springer-Verlag, Berlin, pp. 249-270, 1984.

(Continued)

*Primary Examiner*—Hezron Williams
*Assistant Examiner*—Mark Shabman
(74) *Attorney, Agent, or Firm*—John D. Fado; Robert Jones

(57) ABSTRACT

A Computer Vision Chemical Detector has been developed that uses invertebrate organisms trained to respond to targeted chemical odors.

18 Claims, 75 Drawing Sheets

OTHER PUBLICATIONS

Perez-Maluf, R., et al., "Genetic Variability of Conditioned Probing Responses to a Fruit Odor in Leptopilina boulardi (Hymenoptera: Eucoilidae), a Drosophila Parasitoid", *Behavior Genetics*, vol. 28(1), pp. 67-73, 1998.

Brandes, C., et al., "Common Mechanisms in Proboscis Extension Conditioning and Visual Learning Revealed by Genetic Selection in Honeybees(Aphis melifera capenis)", *J. Comp. Physiol. A.*, vol. 166, pp. 545-552, 1990.

Heinrich, B., "Learning in Invertebrates", Dept. of Zoology, University of Vermont, Burlington, VT 05405, USA.

Alloway, T.M., "Learning and Memory in Insects", *Annu. Rev. Entomol.*, vol. 17, pp. 43-56, 1972.

Papaj, D.R., et al., "Ecological and Evolutionary aspects of Learning in Phytophagous Insects", *Ann. Rev. Entomol.*, vol. 34, pp. 315-350, 1989.

Tumlinson, J.H., et al., "How Parasitic Wasps Find Their Hosts", *Scientific American*, pp. 100-106, Mar. 1993.

Lunau, K., et al., "Optical Releasers of the Innate Proboscis Extension in the Hoverfly Eristalis tenax L. (Syrphidae, Diptera)", *J. Comp. Physiol. A.*, vol. 174, pp. 575-579, 1994.

Wackers, F.L., "The Effect of Food Deprivationon the Innate Visual and Olfactory Preferences in the Parasitoid Cotesia rubecula", *J. Insect Physiol.*, vol. 40(8), pp. 641-649, 1994.

Lewis, Wallace J., et al., U.S. Appl. No. 09/826,146, filed Apr. 5, 2001.

Rains, G.C., et al., "Integration of Precision and Sustainable Technoligies for Healthy Agroecosystems".

Olson, D.M., et al., "Natural Models for Detector Technology: Agricutural, Defense and Medical Applications".

Kerguelen, V., et al., "Processing of Olfactory Stimuli by Female Microplitis croceipes (Hymenoptera: Braconidae) Foraging for Hosts".

* cited by examiner

APPENDIX D: Wasp Hound Electrical Schematic

Appendix A-1: Real-Time.VI Flow Diagram

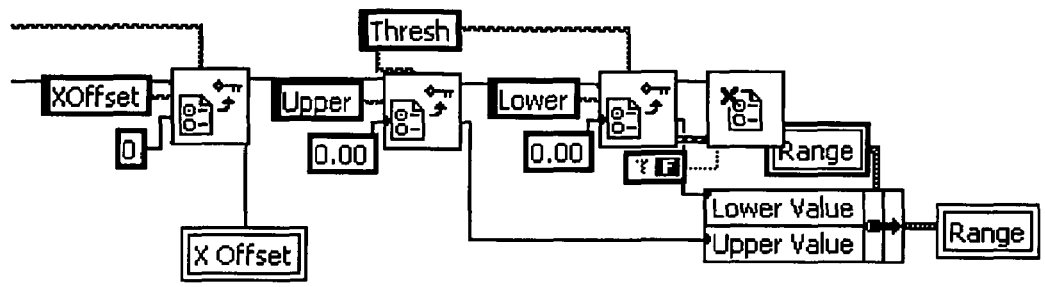
FIG.8B
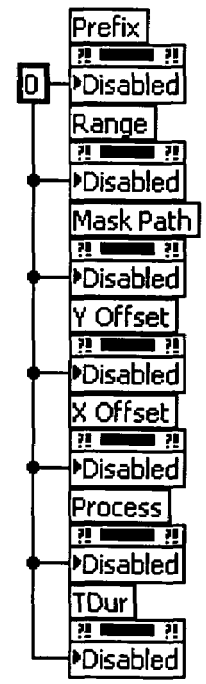

FIG.8G

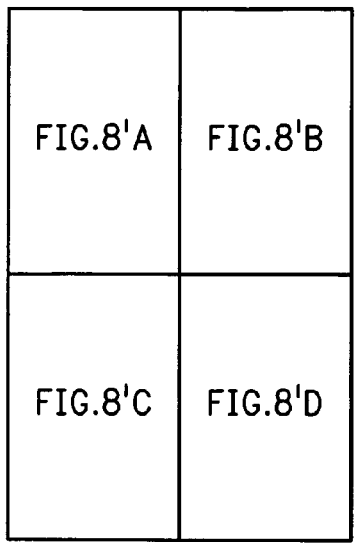
FIG.8'
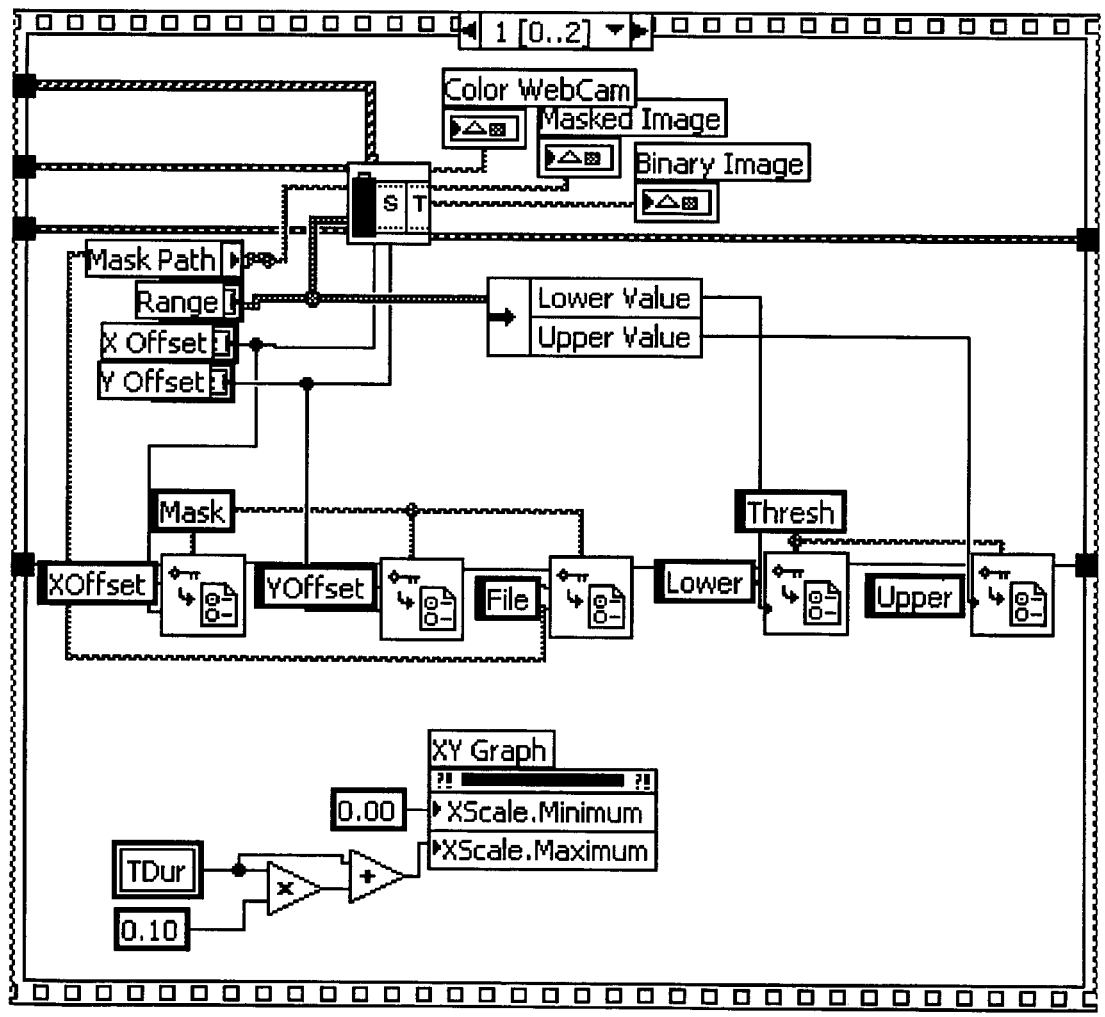
FIG.8'A

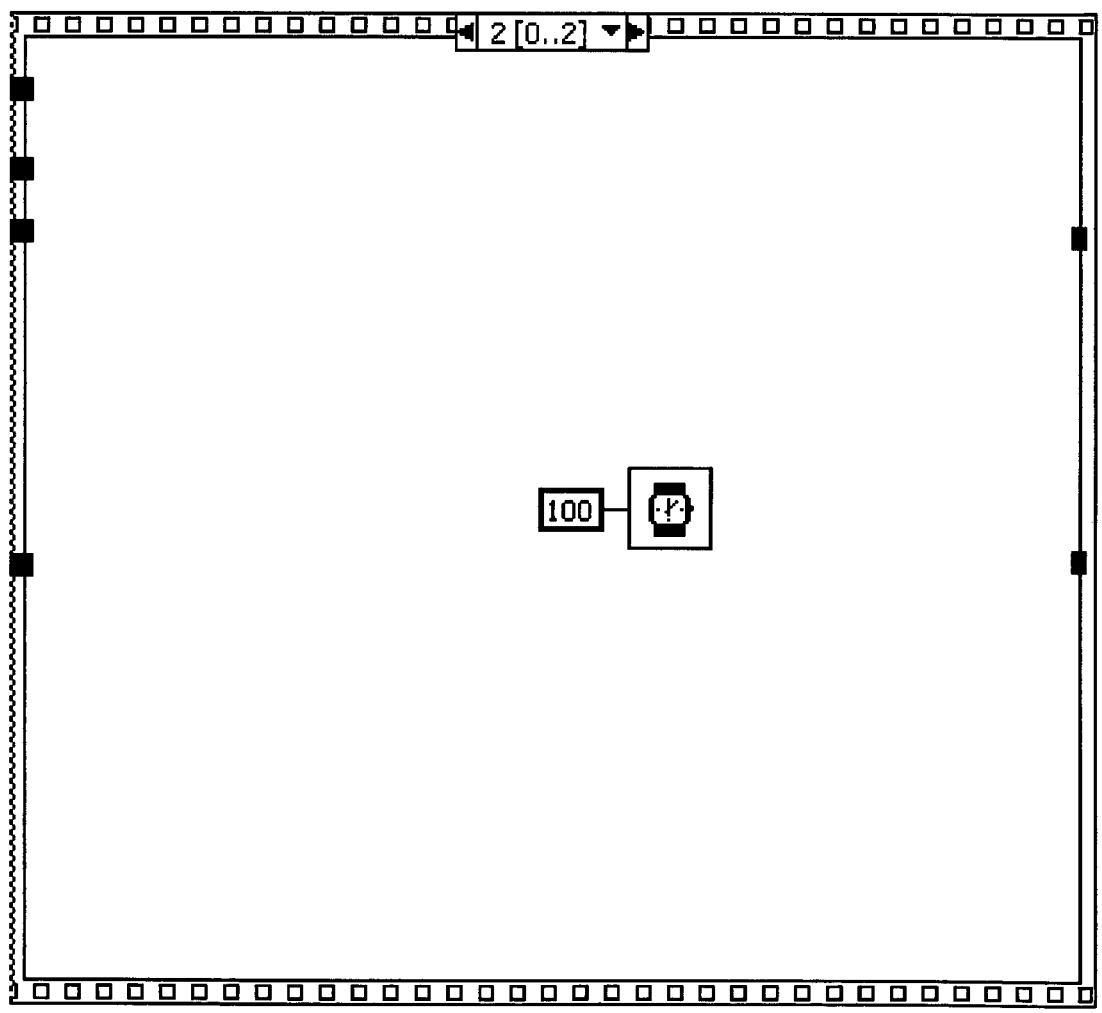
FIG.8'B

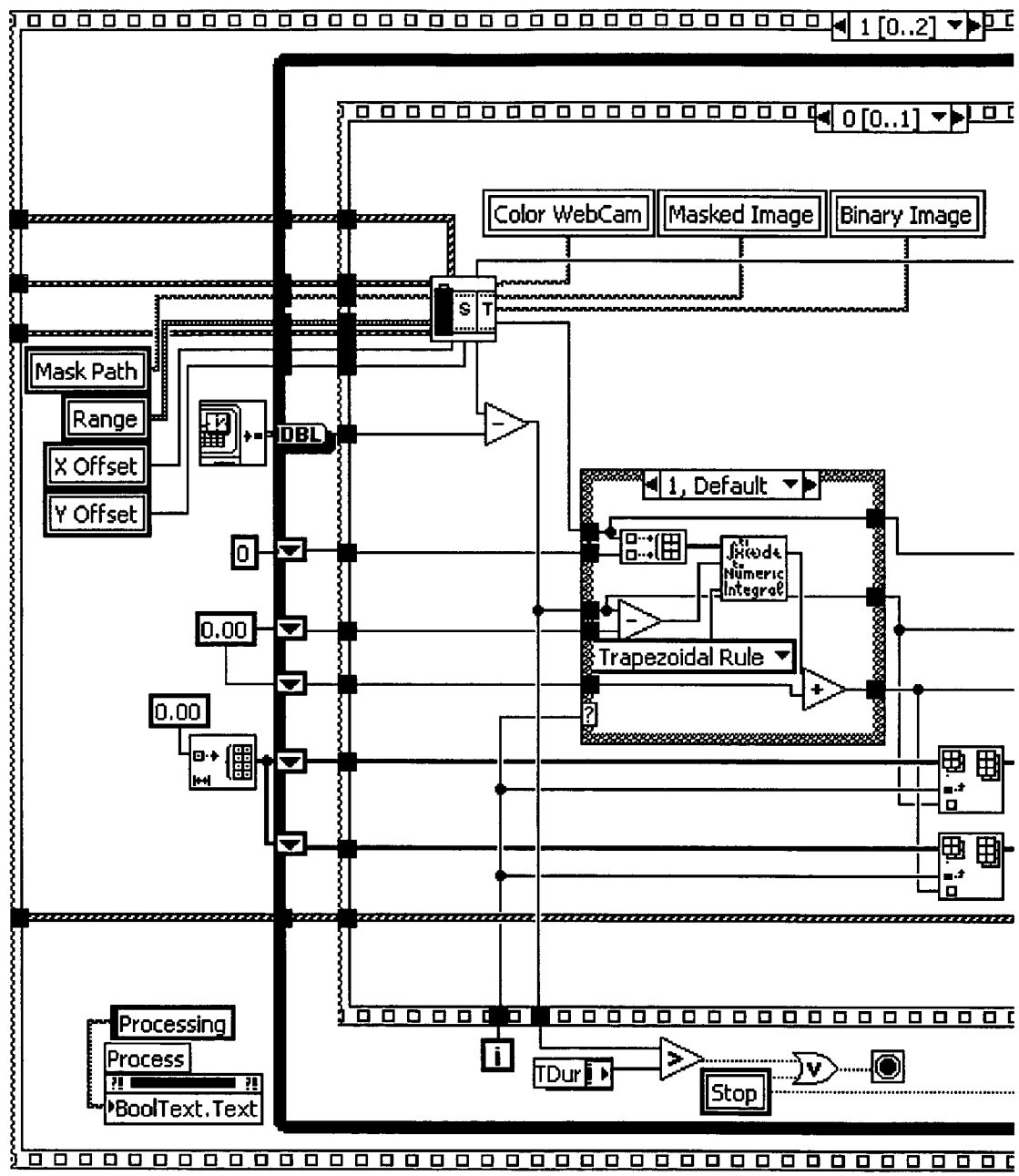
FIG.8'C

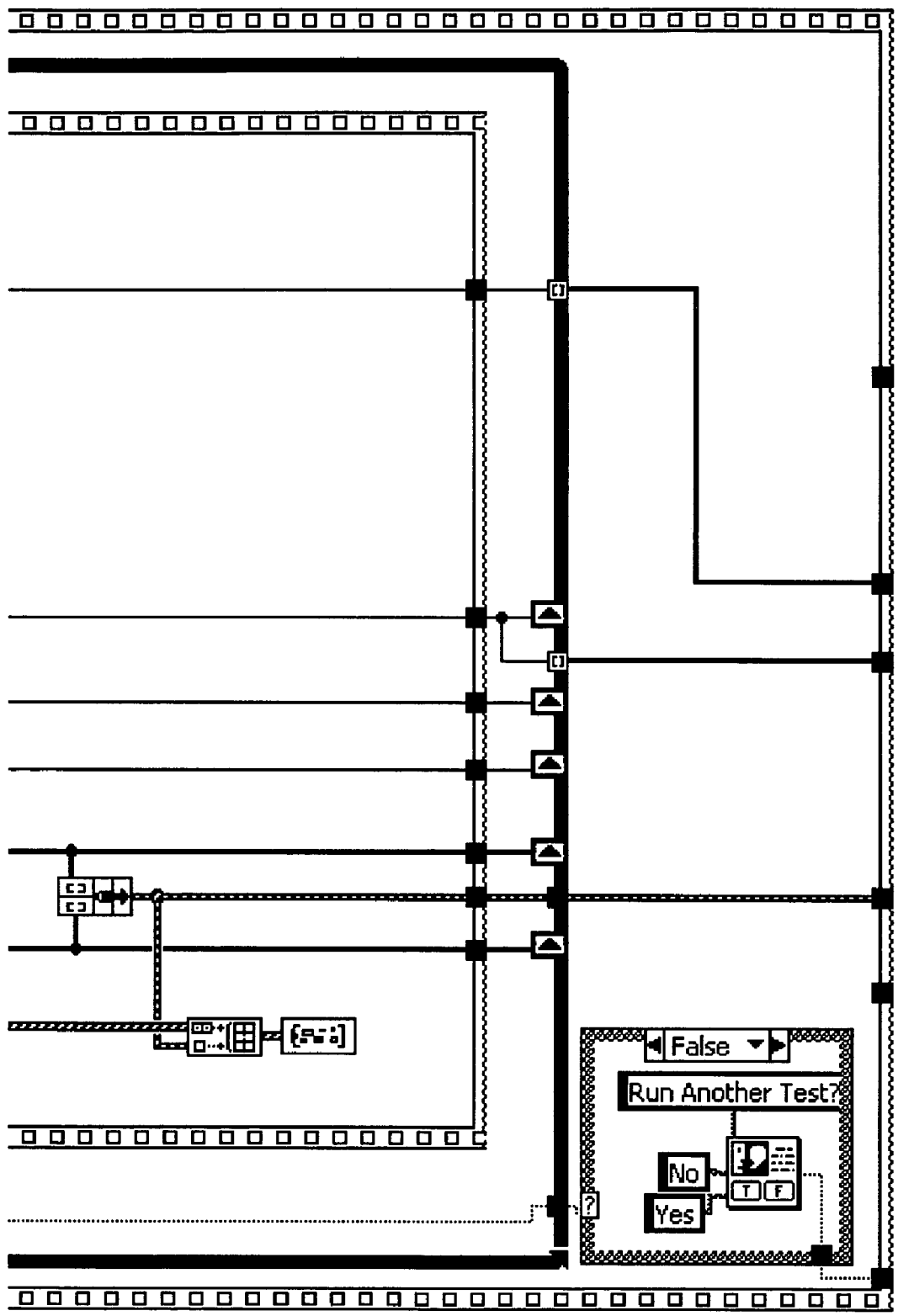
FIG.8'D

Appendix A-2: Capture-Stills.VI Flow Diagram

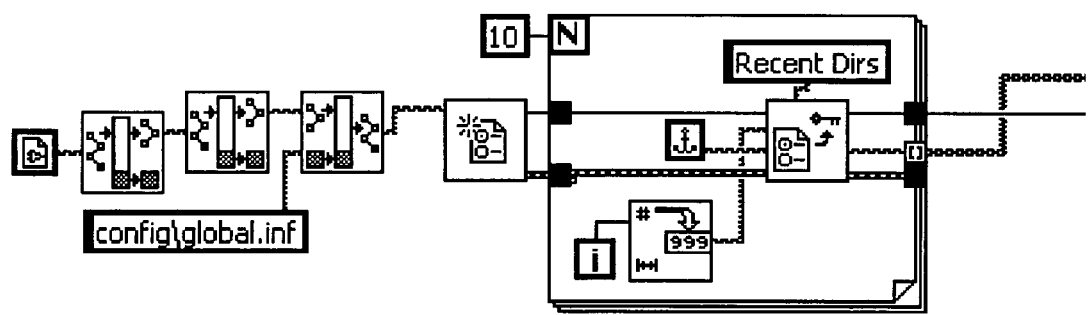
FIG.10A

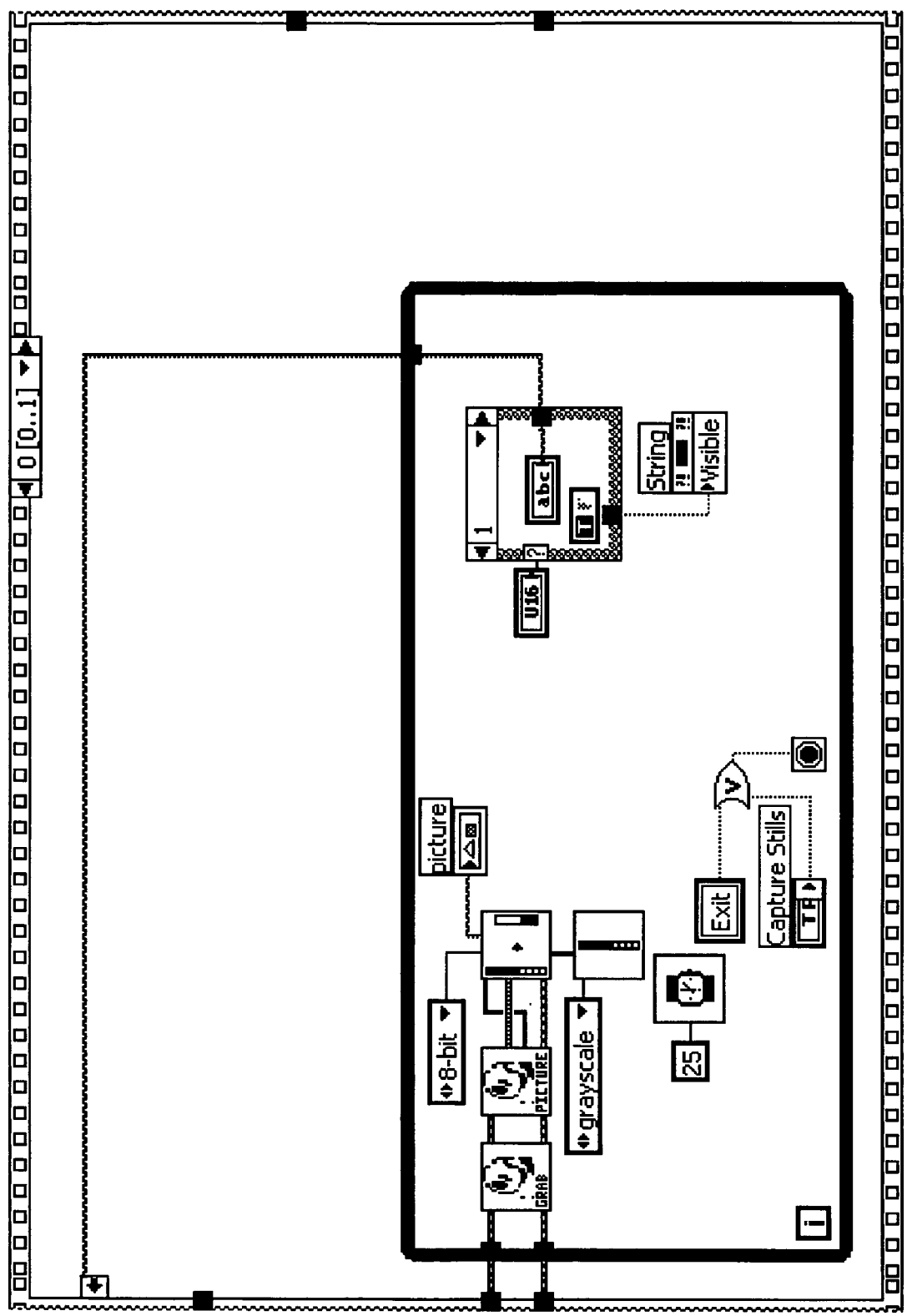
FIG. 10'A

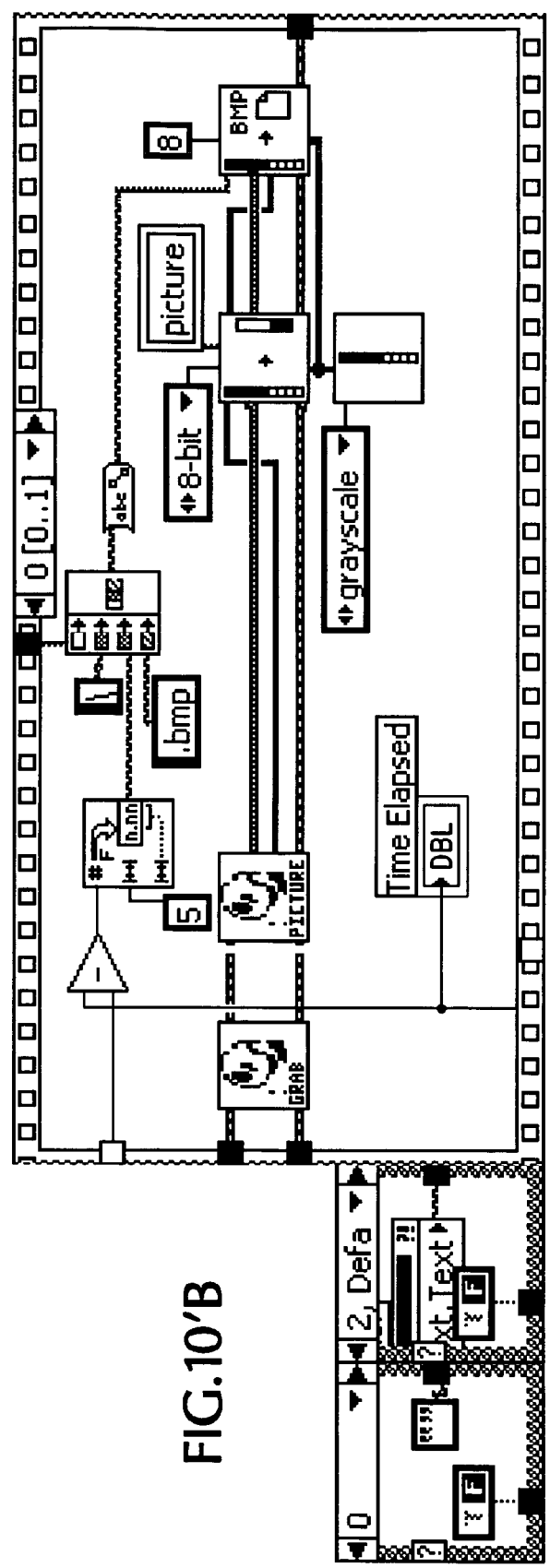
FIG.10'B

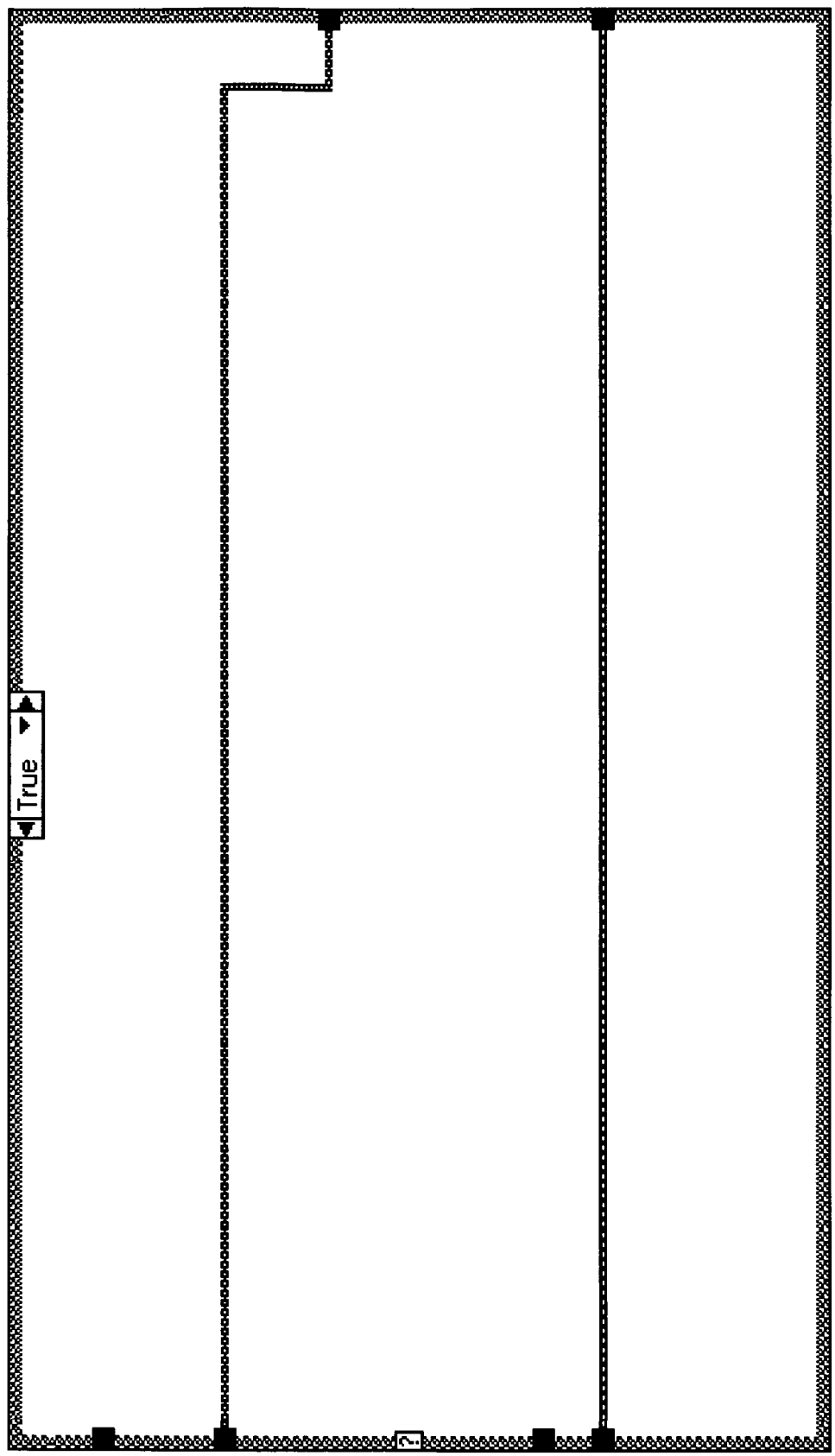
FIG.10'C

Appendix A-3: Process-Stills.VI Flow Diagram

HANDHELD INSTRUMENT FOR MONITORING AND/OR IDENTIFICATION OF CHEMICALS

REFERENCE TO RELATED APPLICATION

This application claims the benefit of U.S. Provisional Application No. 60/592,737, filed Jul. 30, 2004, which is incorporated herein by reference in its entirety.

BACKGROUND OF THE INVENTION

1. Field of the Invention

The present invention relates to a chemical detection system which uses computer vision technology for chemical monitoring and/or identification using invertebrates, especially insects. It also relates to methods for using the system to monitor and/or identify chemicals.

2. Description of the Related Art

Detector systems have played an integral and beneficial role in our culture for many years. Governmental institutions, medicine, agriculture, education, industry, and households rely on chemical and physical detectors for safety, quality control, research and communication. Gas chromatography and mass spectrometry have advanced the understanding of chemistry and the ecology and physiology of species (Olson et al., Physiol. Entomol., 1999, volume 25, 17-26, 2000; Pare et al., Plant Physiol., Volume 114, 1161-1167, 1997), and x-rays and laser imaging have provided a means for detecting pathologies (Boice et al., JAMA, Volume 265, 1290-1294, 1991; Graham-Rowe, New Scientist, Volume 159, 24, 1998), including the quality of foods (Price et al., Food Technology, Volume 44, 6, 1990). Radar sensors are used internationally for communication, navigation, and entertainment (Galatie et al., Iee Proceedings-RADAR, SONAR and Navigation, Volume 144, 156-162, 1997) and Doppler radar systems monitor global weather patterns (Condella, Earth, Volume 7, 56-58, 1998). Near-infrared detectors monitor general vegetation health in agricultural systems (Bosch, Precision Farming: 20-24, 1997), accelerometers are used in cars to detect crash and signal deployment of airbags, and detectors are installed in homes to indicate the presence of harmful radiation, chemicals, and smoke (Edgerton et al., Environ. Science & Technology, Volume 20, 803-807, 1986; Lamarine et al., J. Community Health, Volume 17, 291-401, 1992).

Many of our technological developments have already been adapted from nature, for example, sonar, gyroscopes, heating and air conditioning, aviation, polyester, etc. (Au, Bioacoustics, Volume 8, 137-162, 1997; Engels et al., Studies on Neotropical Fauna and Environment, Volume 30, 193-205, 1995; Sherman, Agricultural Research, Volume 37, 18, 1989). However, with the exception of capturing the bioluminescence of fireflies, beeswax from bees, and the use of domestic animals as detectors (Cherfas, New Scientist, Volume 122, 45, 1989; King et al., Nature, Volume 249, 778-781, 1990), reliance on nature as models for technological development has been generally lacking. Only recently are investigations in the areas of robotics and biomimetics (Goldner, R & D Magazine, Volume 35, 77, 1993; Shimozawa, Rob. Autom. Syst., Volume 18, 75-82, 1996; Srinivasan, Materials Science & Engineering C-biomimetic Materials Sensors and Systems, Volume 4, 19-26, 1996; Weibecker et al., Talanta, Volume 44, 2217-2224, 1997) discovering nature's potential as models for technological development.

Domesticated animals, particularly dogs, have been relied upon as detectors. Historically, humans and domesticated animals have had a close association and many of these species have an incredible ability to detect objects and scents. Humans have been able to harness these abilities largely through training because of their ability to learn. Dogs have been successfully trained to detect narcotics, accelerants used in arson, and explosives, including landmines, and to track game and missing persons in search and rescue operations. However, the learning process and human relationship with these domesticated animals to create the responses to trained stimuli has never been totally understood. It is known that these animals often traverse and operate as effective detectors in less natural arenas, possibly because their historic domesticity has allowed them many years of adaptation to these environments. This ability has provided us with a means to utilize these trained and reliable detectors for our benefit in many different environments.

The U.S. Army Center for Environmental Health and Research (USCEHR) has devised a method for using bluegill sunfish (*Lepomis macrochirus*) for monitoring a broad range of toxins in water (http://usacehr.detrick.army.mil/envsen2.html). The aquatic biomonitor uses mounted electrodes to monitor signals generated in the water by the movement of the fish. When six or more of the eight parameters are detected as abnormal, the system initiates an alert. The system responds within an hour to most chemicals at toxic levels. This aquatic biomonitor is currently being implemented in a New York City reservoir.

Research by APOPO at the Sokoine University of Agriculture in Tanzania has led to the development of a successful regiment for training African Giant Pouched Rats (*Cricetomys gambianus*) to non-destructively detect landmines and accurately detect tuberculosis (http://www.apopo.org). The rats are capable of residual explosive scent tracing (REST) and direct detection of buried mines. The rats can be brought samples for identification or taken out and led through suspected mine fields. For tuberculosis detection, the rats have shown success in discriminating between positive and negative sputum samples without the need for expensive test equipment.

Insentinel Ltd. (Hertforshire, UK) has successfully devised a system using honeybees (*Apis mellifera[Hymenoptera: Linnaeus]*) for trace vapor detection (http://www.inscentinel.com). Using image recognition software, Insentinel bees can be monitor for the activity of a response to the target odor. The systems electronic output can notify a user of the presence of a single target odor.

Detecting volatile chemicals is becoming a leading method of non-invasive searching. Historically, the detection of volatiles has been very important in tracking illegal substances and detecting explosives, but it also has been shown to be a viable means of detecting other organic materials (Rains et al., unpublished, 2003). With the advancing needs of precision agriculture and homeland security, efforts are being made to lower the costs and increase the efficiency of screening through the use of volatile detection. Traditional methods of detecting volatile chemicals include human olfaction, canine training, and electronic olfaction (Gardner and Bartlett, Electronic noses: Principles and Applications, Oxford University Press, Inc., New York, 1998). Of these, human and dogs are the most sensitive, however both can be subjective and costly (Garnder and Bartlett, 1998, supra). Many electronic devices have been developed in response to the cost and reliability associated with volatile detection and range in design from simple, such as a metal oxide doped transistor, to complex, such as an array of polymer-coated sensors analyzed using neural networks. The simple designs are relatively inexpensive but are normally very specific and sensitive to low concentrations, or they detect a wider range of volatiles but lack sensitivity (Gardner and Bartlett, 1998, supra; Dickinson, TIBTECH, Volume 16, 250-258, 1998; Börgesson et al., Cereal Chemistry, Volume 73 (4), 457-461, 1996). More elaborate electronic nose designs are inexpensive relative to training and maintaining a canine, but are about 100 times less sensitive than human olfaction (Raman and Gerhardt, Transactions of the ASAE, Volume 40 (6), 1699-1707, 1997; Sarig, J. Aric. Engng Res., Volume 77 (3), 239-258, 2000), and the user is left to interpret the complex output (Rains et al., ASAE Meeting Paper No. 01-1069, 2001).

Although existing chemical detectors are specific and reliable and have allowed major advances in our ability to monitor for target chemicals, there remains a need in the art for chemical detector-systems that have sensitivity, programmability, portability, and a cryptic nature that are needed for many current problems requiring detection and monitoring. The present invention provides a system and method of chemical detection which is different from prior art methods.

SUMMARY OF THE INVENTION

It is therefore an object of the present invention to provide a computer vision detection system containing at least one trained invertebrate organism for identification of target chemicals and a camera operatively connected to a computer.

Another object of the present invention is to provide a computer vision detection system that includes at least one detection chamber containing at least one trained invertebrate organism and an air delivery system.

A still further object of the present invention is to provide a method for recording at least one response of at least one trained organism to at least one target chemical using a computer vision detection system.

Another object of the present invention is to provide a method for detecting target chemicals which includes training an invertebrate organism to display a typical behavior in response to the smell of a target chemical, placing at least one trained organism in at least one detection chamber compartment containing a camera, bringing air from the suspected area through the detection chamber and recording images of the organisms behavior with the camera, and transmitting the images to a computer containing software for data analysis.

Further objects and advantages of the invention will become apparent from the following description.

BRIEF DESCRIPTION OF THE DRAWINGS

Figure 8G:
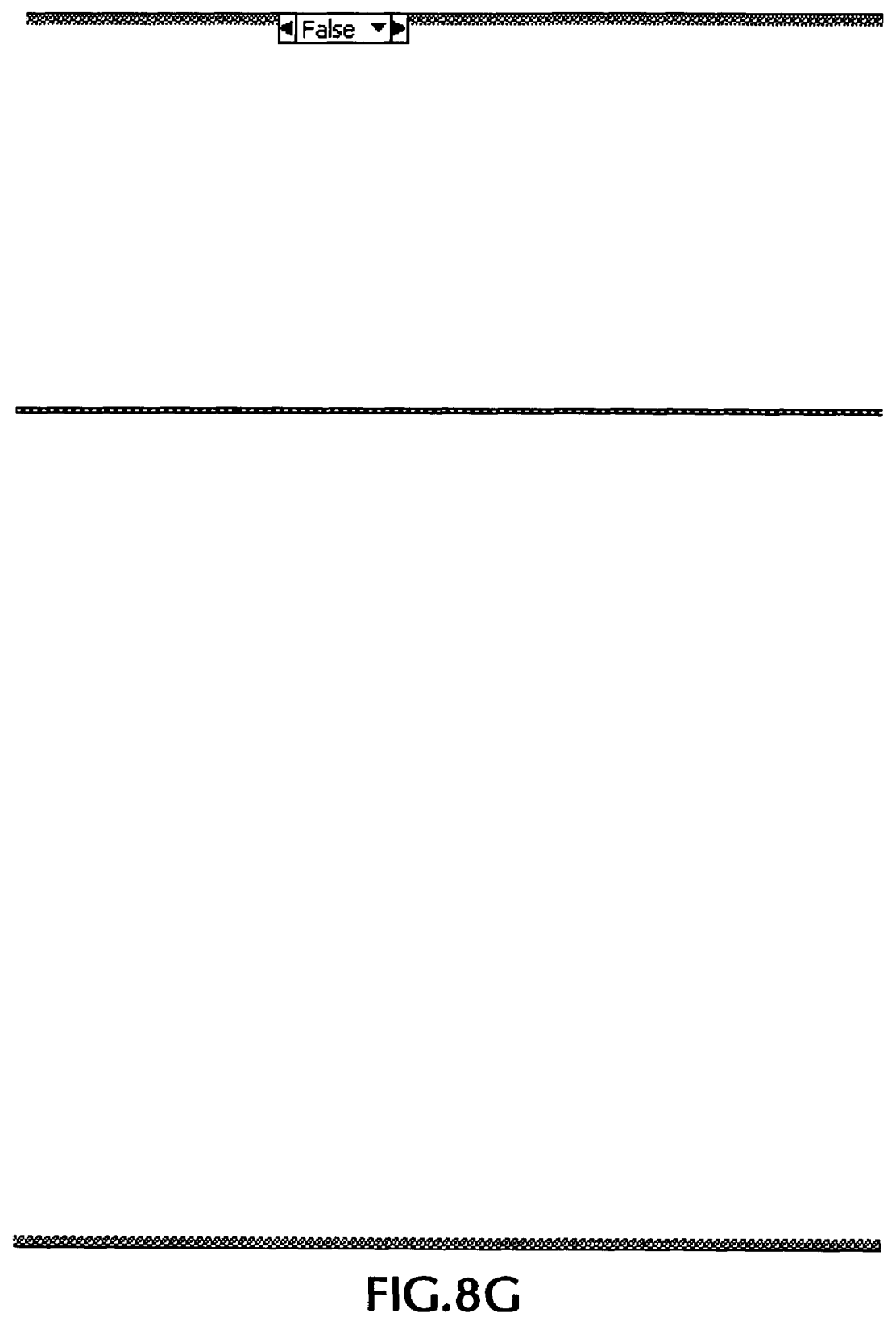

FIGS. 8 and 8A-8H are drawings showing the Real-Time.VI LabVIEW Block Diagram.

FIGS. 10 and 10A-10F are drawings showing the Capture-Stills.VI LabVIEW Block Diagram.

DETAILED DESCRIPTION OF THE INVENTION

Figure 1A:
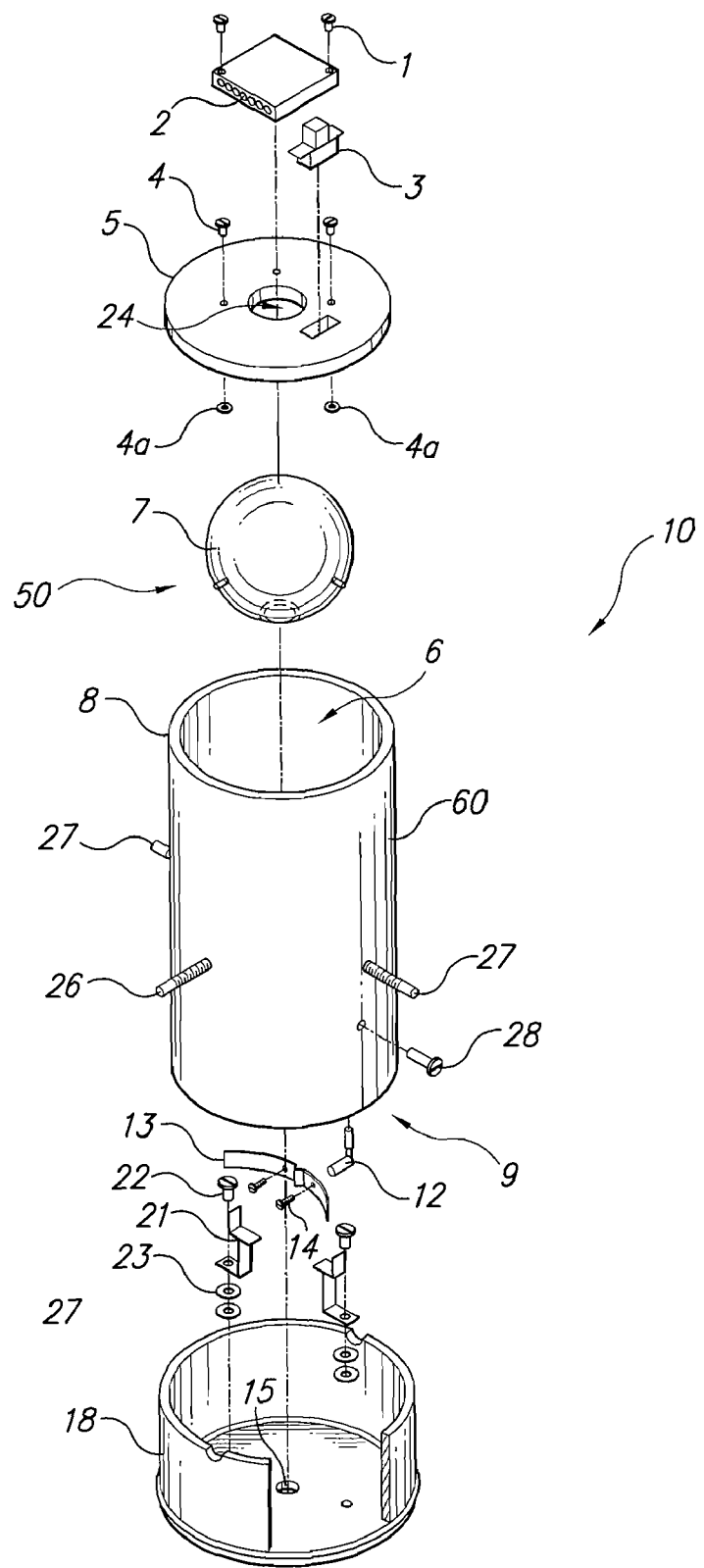
FIG. 1A is an exploded view of the device 10.
Figure 1B:
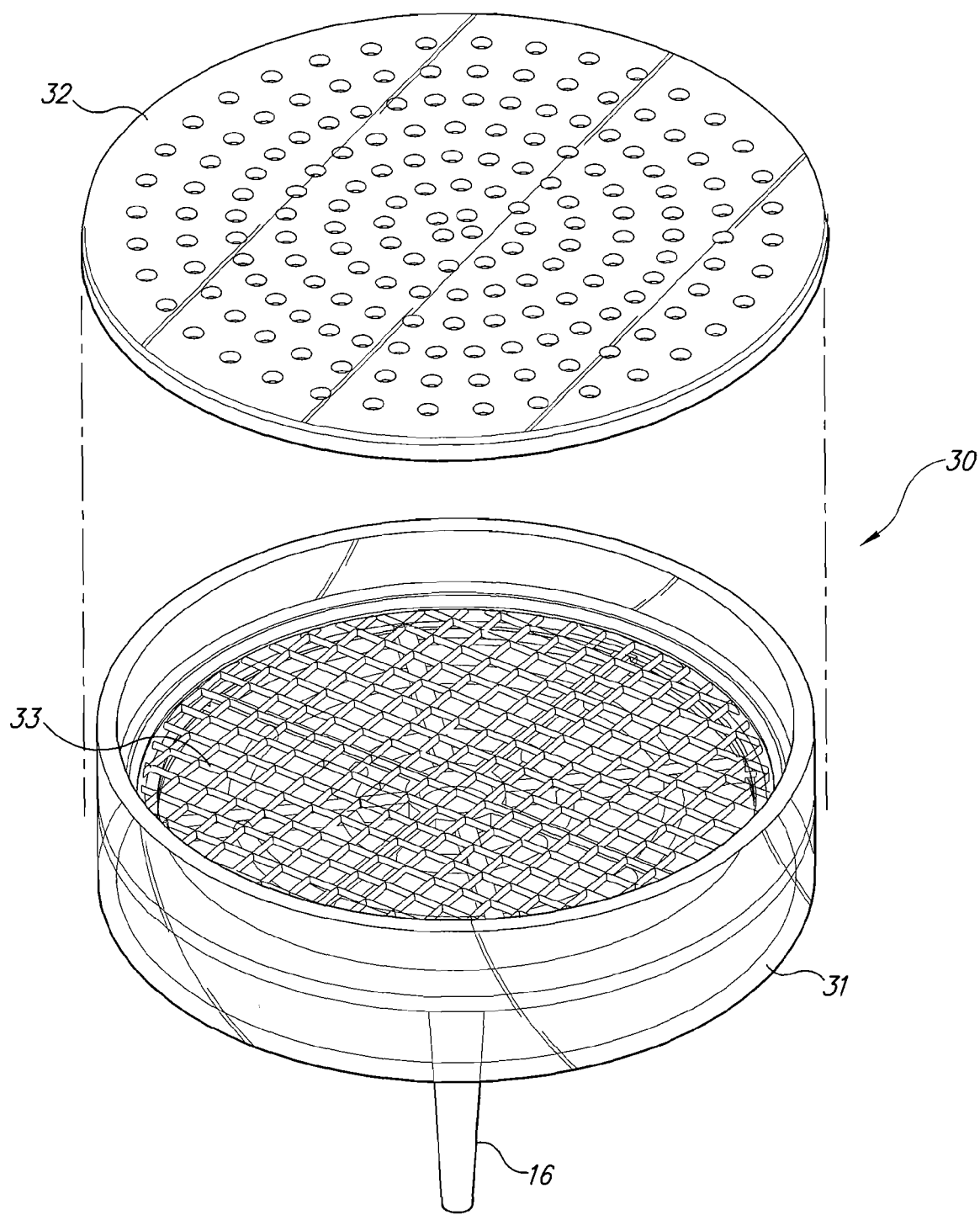
FIG. 1B is an exploded view of the compartment detection chamber 30.
Figure 1C:
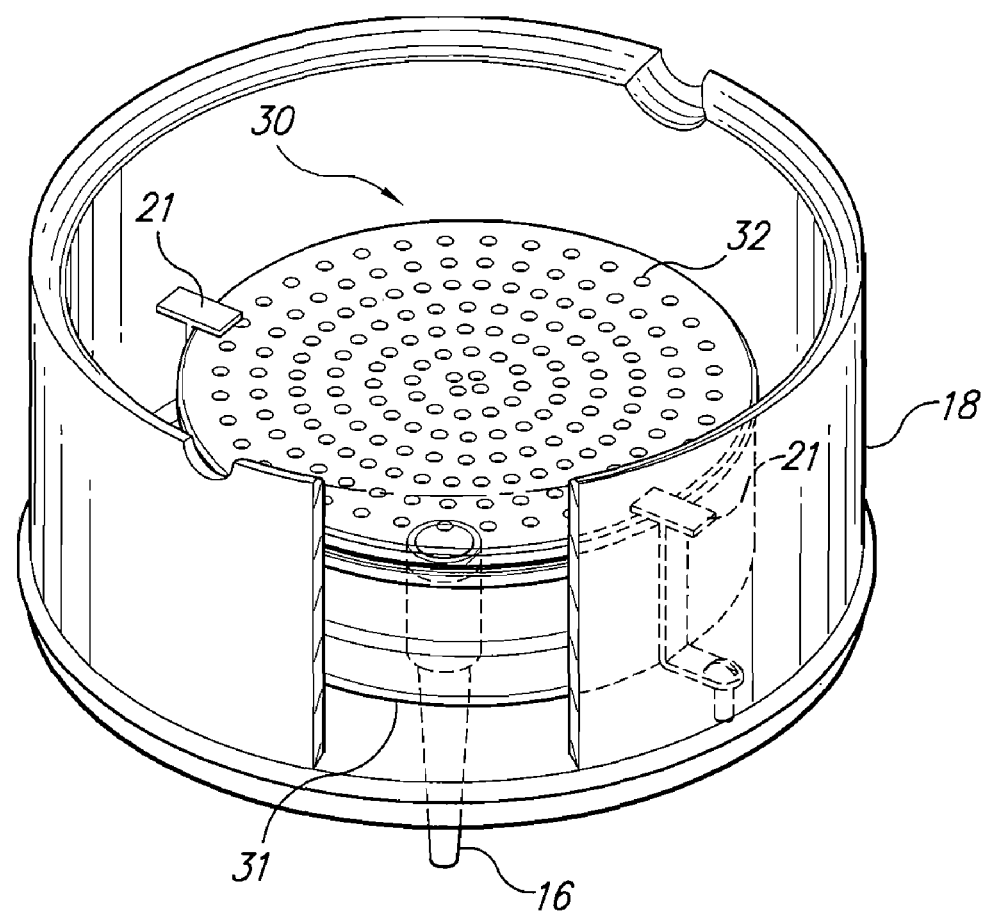
FIG. 1C is shows the detection chamber 30 secured in the base 18 of the device 10.
Figure 1D:
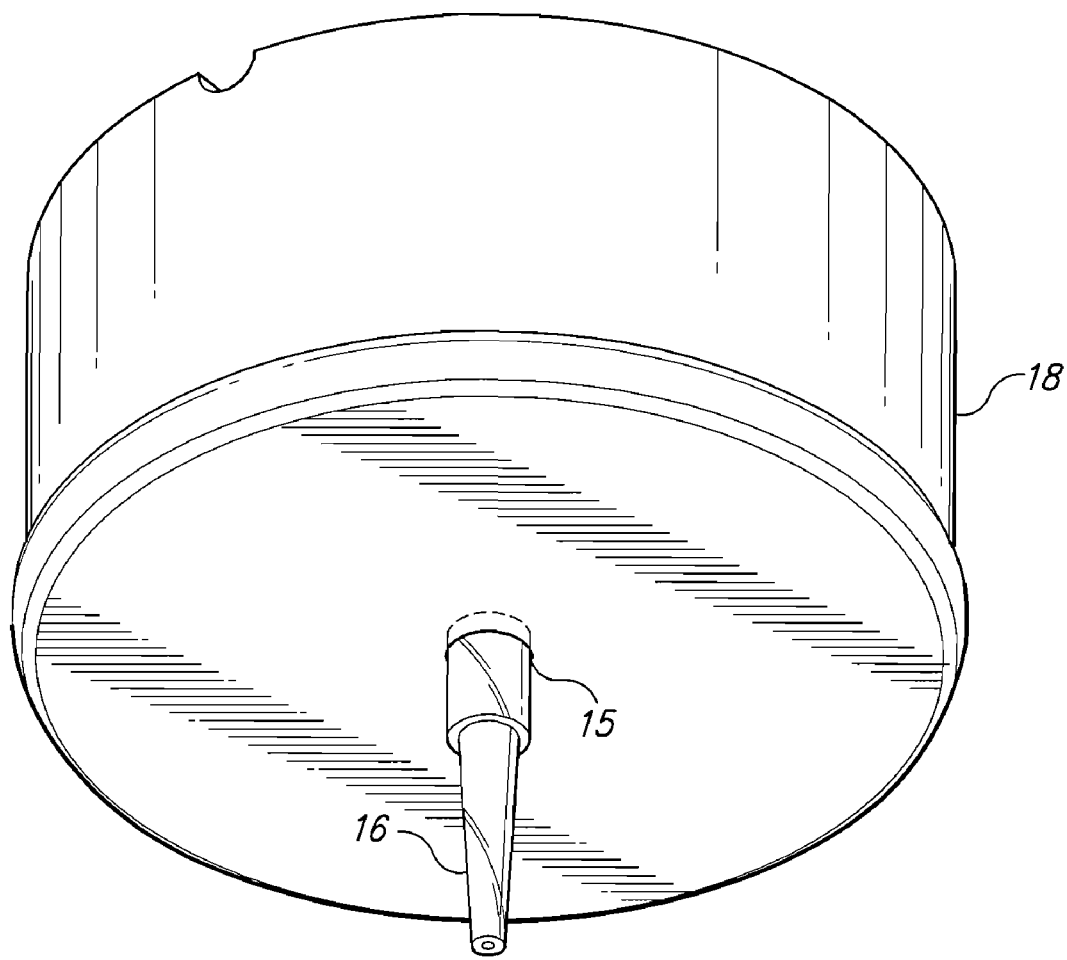
FIG. 1D shows the funnel-shaped inlet 16 of the detection chamber 30 extending from the base 18 of the device 10.

Invertebrate organisms can be used as highly flexible and sensitive detectors in a system for chemical monitoring and/or detection. The three major areas which benefit from a sensitive, portable, cryptic and reliable detection system include agriculture, national defense, and medicine.

There is a growing need for more sensitive, programmable, portable, and cryptic detector systems. A contained invertebrate organism, such as an insect, provides two means for retrieving information. First, the organism interprets and expresses behavior(s) in response to the presence of a chemical. The expressed behavior(s) is distinct, i.e. easily recognized, and is a reliable indicator of the presence of a chemical. The organism must remain focused and is not easily distracted. Second, the sensory apparatus, such as antennae, antennae lobe or brain for example, of the contained organism can be tapped into to obtain the response. Both avenues require that the organism be delivered to the source or the source be delivered to the organism and monitored by an individual or the processed information analyzed by a programmed computer. The present invention can be used in easily accessible areas, such as for example, airports, agricultural fields, hospitals, etc.

In agriculture, the detectors of the present invention will allow plant and soil health to be monitored as well as interaction of species which leads to early problem detection and intervention. Current technology, using remote sensing systems, cannot immediately detect specific nutrient levels or early stages of pest infestations, and large and expensive gas chromatography and optical and mass spectrometry equipment cannot be taken to the field, which limits diagnosis to a few transported samples. In addition, small, rugged, and inexpensive solid state chemosensors, like metal doped $SnO_2$-sensors, lack the sensitivity and selectivity that is necessary.

In the area of national defense for chemical and biological weapons detection, bio-weapons cannot be detected with radiation or x-ray, making them well concealed and easily transported for release into transit, water and food systems. Medical centers are not prepared for the delays inherent in recognizing that a bio-weapon has been released. There is a need for new technology for rapid and sensitive weapon detection, including the need for more cryptic means of detection in adversarial zones.

In medicine, there is a need for less invasive detection of pathogens and monitoring of human and animal health. Recent studies show that dogs can be trained to noninvasively detect screwworm infested animals and breath analysis can detect peptic ulcer disease, both procedures eliminating the need for painful endoscopic examinations.

The present invention separates a very specific behavior from its biological context for use as a reporting device, called a response behavior. This response behavior is defined for purposes of the present invention as any behavior the organism usually displays when in close proximity to a biological resource such as, for example, food, mate, prey, or host. This response behavior can be isolated from the organism's natural behavioral context and used with any chemical cue using the training method as set forth in U.S. patent application Ser. No. 09/826,146 ('146) herein incorporated by reference in its entirety. The method of the '146 application quickly programs the organisms in at least about 1 minute to about 4 hours and brings the organisms to report trained odors, especially odors not related to the biology of the organism, with high accuracy under a wide range of environmental conditions. The trained organisms can pick out a single chemical from a chemical blend after being trained to that chemical. Knowledge of the chemical nature of the programmed odors is not necessary.

This invention provides a portable computer vision system to utilize invertebrates, especially insects, trained to detect volatile chemical odors. Insects have experienced intense selection pressure for sensitive and effective ability to locate mates, food and hosts in nature. For example, *Microplitis croceipes* Cresson are endoparasitoids of the larvae of *Heliocoverpa zea* Boddie and are able to detect and respond to volatile chemicals from host plant sources in amounts as low as $4.5 \times 10^{-16}$ M. Such low detection thresholds are comparable to those of vertebrates (Smith et al., Annu. Rev. Entomol., Volume 39, 351-375, 1995; Stoddart, In: The Ecology of Vertebrate Olfaction, 58-62, 1980, Chapman and Hall, New York, N.Y.). Insects are able to learn which allows them to be programmable. Only recently the breadth of insects learning abilities has been discovered (Papaj et al., In. Insect Learning. Ecological and Evolutionary Perspectives. Chapman and Hall, 1993; Vet et al., In: Chemical Ecology of Insects 2, 65-101, 1995, Chapman and Hall, New York, N.Y.). Invertebrates have a very short generation time and they can be easily reared in large numbers. The great diversity of insects allow different species to be drawn upon for use in specific habitats or environments.

Any organism trained to detect a volatile odor can be used with device 10 of the present invention. Device 10 is a portable computer vision system which has a means for introducing a sample of air from a suspected area into at least one detection chamber 30 containing at least one trained organism (FIG. 1). Device 10 is a programmable, portable, and cryptic detector system for detecting at least one chemical such as for example those contained in explosives, those associated with microorganism contamination, those associated with parasitic contamination, those associated with various contraband, etc. Components of detector 10 include a laptop computer, web camera 7 and a data analysis system (not shown), a ventilated area 20b, a lighting source 12, and a detection chamber 30. The analysis of the information received from camera 7 is performed on a laptop computer with one computer serial port input line interfacing with camera 7. One of ordinary skill in the art could readily determine how to perform the information analysis using any type of hardware that is compatible with a software program capable of analyzing data received from camera 7 from the following detailed description.

Figure 2:
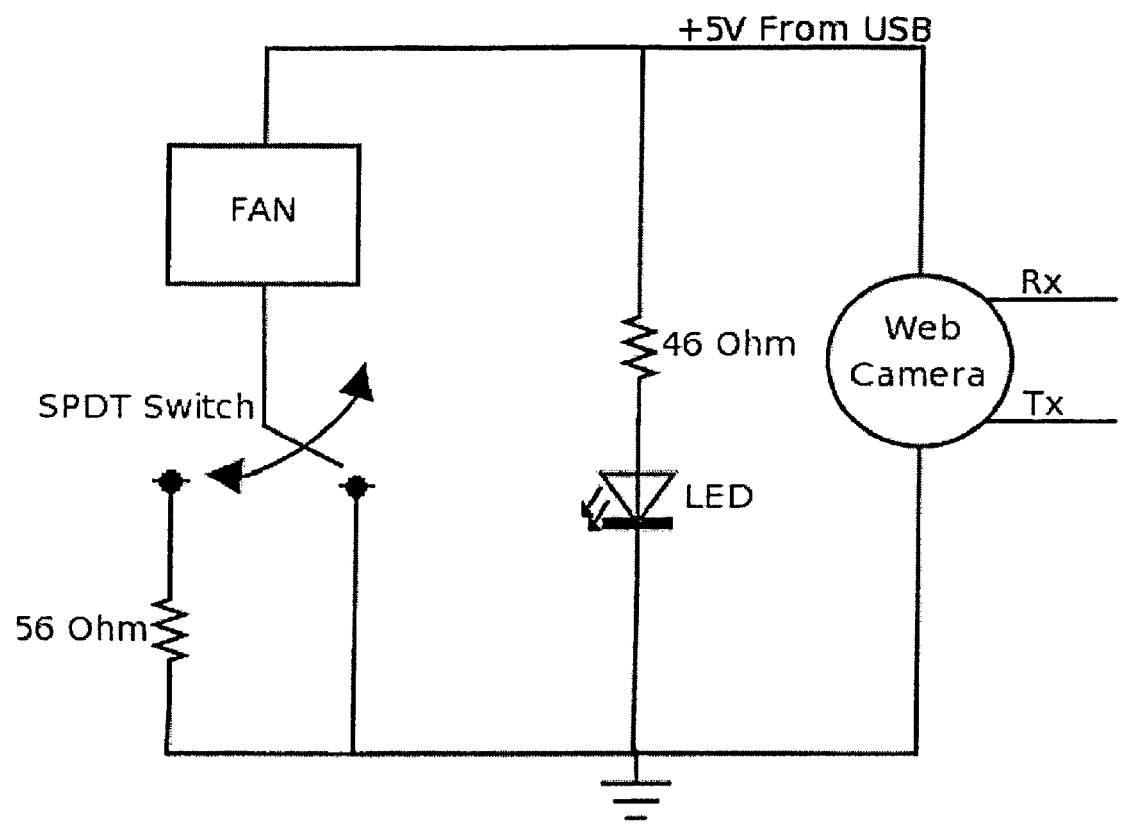
FIG. 2 is a drawing of device 10 electrical schematic.

Detector 10 has an air system 20 which slowly brings air from outside the system to be tested into the ventilated area 20b through an opening in the base of chamber 30 of device 10 and exhausts it. Air system 20 includes a ventilation fan 2 within body 8 and ventilated area 20b and includes the inside of body 8 and cap 18. Ventilation fan 2 can be any fan which draws less than 0.43 cubic feet per minute (CFM) in a range of about 0.1 to about 0.3 cubic feet per minute. Examples of ventilation fan 2 useful in the present invention include, for example, a flat unidirectional CPU fan (DigiKey, P11086-ND). One of ordinary skill in the art could readily determine what type of fan to use given the detailed description of the present invention. Fan 2 is attached to top 5 of device 10 using any fastening means 1, such as for example, any type of screw. Fan 2 speed is variable between about 12.18 milliliters/minute or about 0.43 cubic feet per minute to purge the system and less than 12.18 milliliters/minute under testing conditions. Speed is varied through the use of a single pole double throw (SPDT) switch 3 and about a 56 Ohm current limiting resistor (not shown). The resistor is soldered onto one of the leads of switch 3. One of ordinary skill in art could readily determine where to place the resistor following the circuit diagram (FIG. 2). Fan 2 allows the creation of an odor gradient inside cap 18 and body 8 by slowly drawing outside air through port 15 located in cap 18. A funnel-shaped inlet 16 frictionally attaches to port 18 on the outside bottom of cap 18 or in the base of chamber 30 and extends through cap 18 and allows air to be drawn into cap 18 and into detection chamber 21 where at least one trained organism 35 is located. The air exits through the top of chamber 21 and is subsequently drawn through body 8 and out ventilation fan 2.

A power source (not shown) is provided to device 10 through a universal serial bus (USB) connection (not shown). A USB cable is hard wired to camera 7, lighting source 12 and fan 2 in parallel and all are powered by the computer through the USB cable. Standard wire of about 31 to about 24 AWG and wire to wire connectors, such as Molex connectors for example, are used to make all electrical branchings from the USB cable (not shown).

Figure 15:
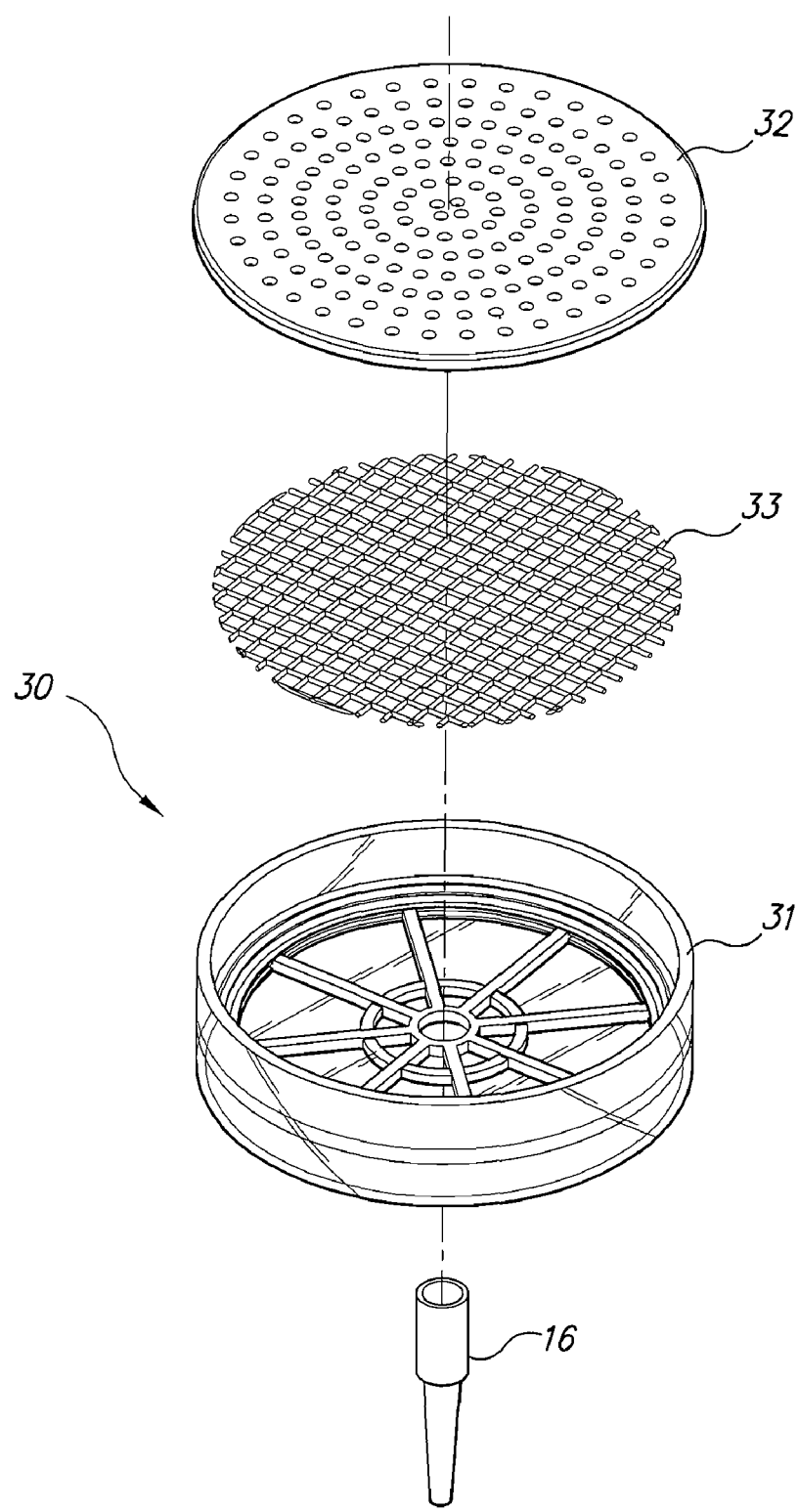
FIG. 15 is an exploded view of chamber 30 showing body 31, top 32, and mesh disc 33.
Figure 16:
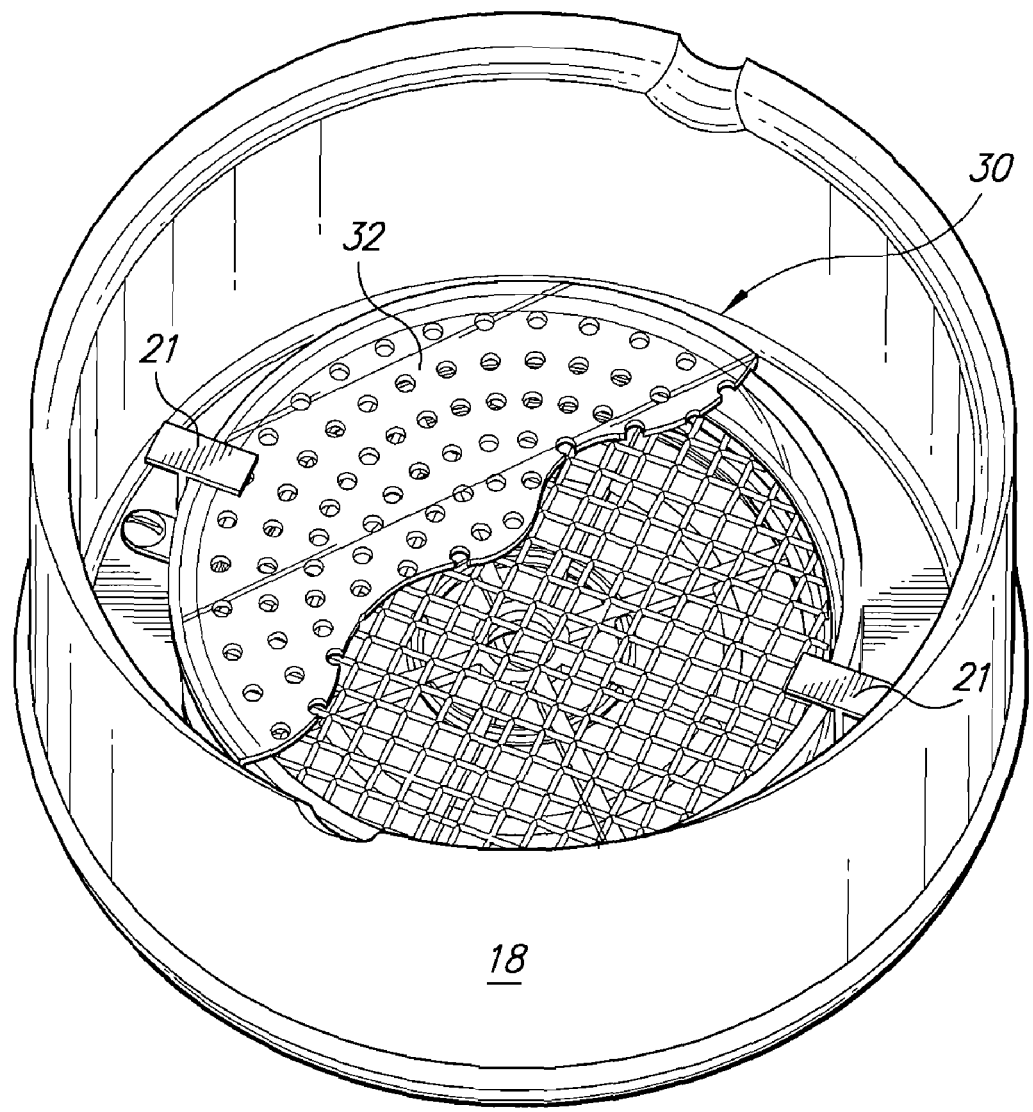
FIG. 16 is a top perspective view of chamber 30 positioned in the base 18 of the device 10. The top 32 is partially cut away to show the interior of the chamber 30.
Figure 17:
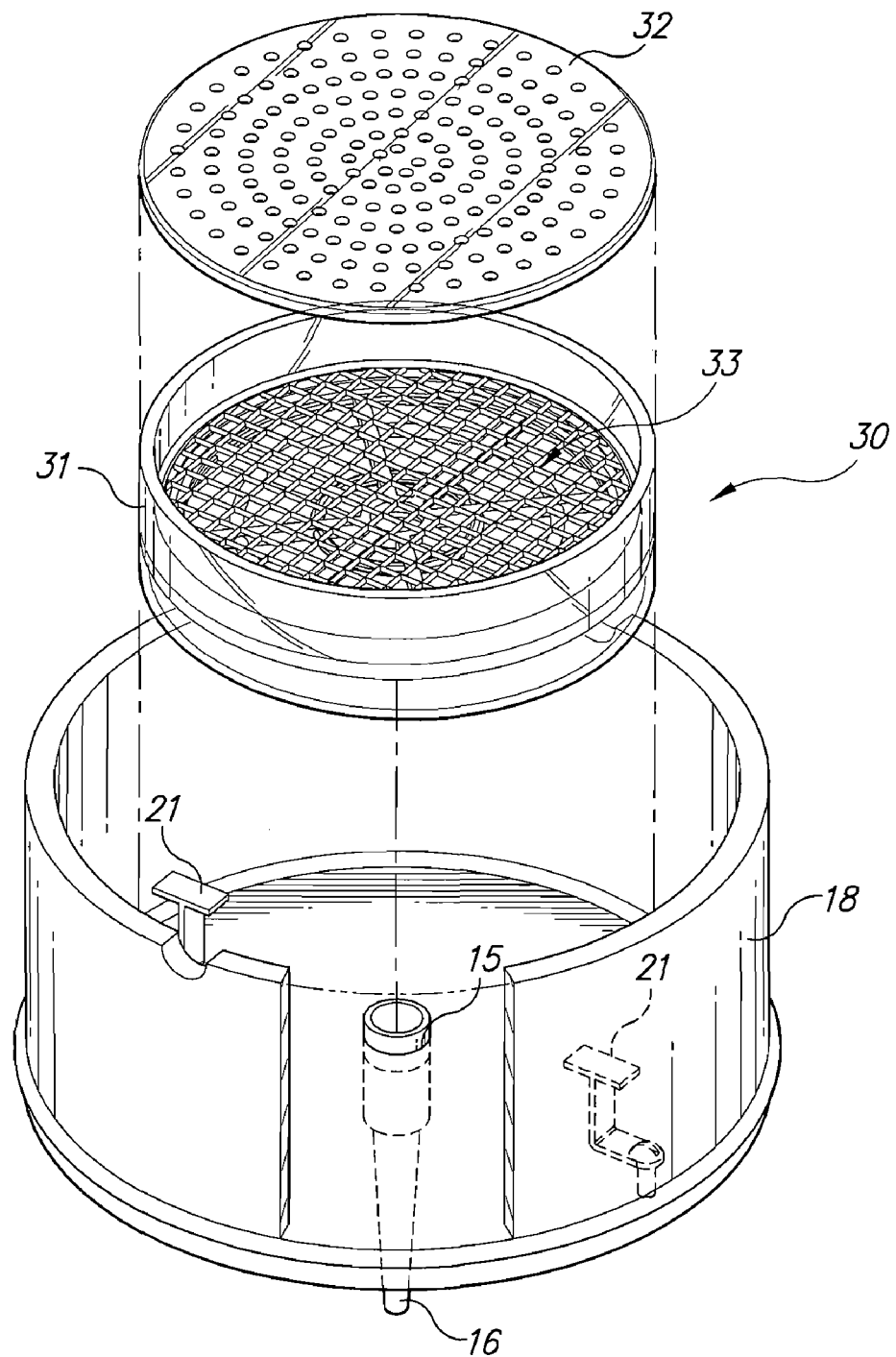
FIG. 17 is an exploded view of the chamber 30 in combination with the base 18 of the device 10.

As shown in FIGS. 1B-D and 15-17, detection chamber 30 provides a container for the trained invertebrate which is sized to allow sufficient movement of several trained invertebrates but not so large as to diminish their timely responsiveness (FIGS. 15-17). Chamber 30 has to be well ventilated and transparent in order to monitor and illuminate the interior. Detection chamber 30 is constructed of light weight transparent material which does not absorb odors. Examples include a plastic, glass, acrylic, etc., which allows viewing of trained organism 35. In the embodiment used in the example below, a Millipore Aerosol Analysis Monitor was used for body 31. Top 32 was a lid for a Millipore PetriSlide™ modified to fit the body and thoroughly perforated to allow for ventilation by fan 2 (FIG. 16). A wire mesh disc 33 was placed in the bottom of the body 31 to prevent the trained vertebrate from escaping through the inlet (FIGS. 1B-C and 15-17).

For purposes of the present invention, invertebrates include, for example, Arthropods, including but not limited to wasps, bees, moths, butterflies, beetles, true bugs (e.g. assassin bugs); and arachnids, for example, including but not limited to spiders, mites, ticks, and scorpions; Crustaceans, for example, including but not limited to crayfish, lobster, and crabs; and mollusks, for example, including but not limited to snails, slugs, squids, and clams.

Housing 60 of device 10 includes a top 5, a body 8, and a cap 18 which keeps all of the components positioned statically and allows for consistent uniform lighting from lighting source 12. Any component of housing 60 can be of any material which is compatible with the air being sampled and does not absorb odors. Examples include polyvinylchloride (PVC), Teflon, glass, etc. Determination of useful materials for housing 60 is well within the ordinary skill in the art.

Body 8 can be of any size or shape to house sensor means 50 which is camera 7. Typically, body 8 is cylindrical in shape with a top opening 6 and bottom opening 9 to form a ventilated area 11. Body 8 can be made of any material as discussed above for housing 60, such as, for example schedule 40 PVC pipe. The dimensions of body 8 used in the example below were about 15.72 cm length and about 7.62 cm width. Body 8 contains 3 through openings, into which are placed a middle alignment screw 26 and two side alignment screws 27, on three of its quadrants for supporting or suspending sensor means 50 inside body 8. Any means for supporting or suspending sensor means 50 is useful, the determination of which is within the ordinary skill in the art given the present detailed description. Examples of other means for supporting or suspending sensor means 50 include for example a non-odorous epoxy or glue. Two of through openings on opposing sides, holding side support screws 27, are located approximately 7.66 cm from the top of body 8 and the third through opening, which holds middle alignment screw 26, is located approximately 8.85 cm from the top of body 8. A fourth opening cap align screw 28, drilled halfway through the (inside or outside of the body wall) wall of body 8 is located about 3.81 cm from the top for a bolt to properly align top 5. Cap 18 frictionally attaches to body 8 to enclose bottom opening 9. Cap 18 can be of any size or shape that fits body 8, determination of which is well within the ordinary skill in the art. In example 3 below, cap 18 is an approximately 7.62 centimeter flat-bottomed PVC cap (Genova Plumbing Products, #70153), notched with notch 19 for consistent placement. The center of the inside of cap 18 was bored out to a depth of about 0.3175 cm and diameter of about 3.97 cm. An approximately 0.4 cm diameter cap through opening (not shown) was made in the center of the bore to allow air to be drawn into the ventilation area. Two detection chamber brackets 21 are located on each side of the bore and are used to hold test cartridge 30 in the bored out area. Brackets 21 are made of any soft metal and each are held in place by one screw 22 and two washers 23. Brackets 21 can be made of any material that has elasticity such as, for example, plastic, metal, rubber, etc. One of ordinary skill in the art could readily determine how to secure chamber 21 in cap 18. The top of body 8 is capped with top 5 which is a flat and circular in shape. Top 5 is approximately 0.635 cm thick. Top 5 is held in place by two screws 4. Washers 4a provide a spacing between top 5 and body 8 which controls the flow rate of the intake of inlet 16. An opening 24 is cut into top 5 to allow for mounting of ventilation fan 2. The size of the opening is determined by the size of the ventitilation fan which is within the ordinary skill in the art. In example 3, device 10 has a flat CPU fan 2 (DigiKey, P 11036-N) has an opening 24 which is approximately 2.3 cm. A rectangular-shaped opening 25 is placed about 2.06 cm from the center of top 5 to allow for mounting of switch 3. The size and shape of the opening is determined by the type of switch 3 used and is within the ordinary skill in the art. For a SPDT switch 3 and 56 Ohm resistor, opening 25 was approximately 0.79 cm×1.59 cm. Inside of body 8, lighting source bracket 13 can be made of any material and can be of any shape which will hold lighting source 12 against the inside of body 8. Bracket 13 is mounted using bracket screws 14 approximately 0.635 cm from the bottom of body 8 to hold a lighting source 12 in place. Lighting source 12 is mounted to the lower part of body 8 using a bracket 13 and screws 14. Lighting source 12 must provide consistent uniform lighting. One example of lighting source 12 is a white 2300 mcd LED (DigiKey, CMD333UWC) and a current limiting 46 Ohm resistor. One of ordinary skill in the art could readily determine the type of light source given the detailed description of the present invention.

Computer vision system 50, of the present invention, includes a camera 7, a laptop, and a software package. Computer vision is a vast field integrating the principles of electrical, computer, and optical engineering. Its application varies but the guiding principle behind computer vision is to allow for automated visual inspection. Much like the human visual system, a minimal computer vision system consists of a camera (eye) for acquiring images and an electronic or computer device (brain) for processing those images.

Each image acquired must be captured in or converted to a digital format before it can be processed in the computer. An image is digitally represented by small sections called pixels. The amount of pixels used to represent a single image is dependent upon the camera's detector or frame grabber. Each pixel has an intensity value associated with it. For example, a pixel within an image of 8 bit resolution can take on a value from about 0 to about 255 ($2^8-1$). In a 8 bit grayscale image, 0 is black, 255 is white, and everything in between is a shade of gray. Each picture is digitized by turning it into a two-dimensional array (x,y coordinates) of values.

Figure 3:
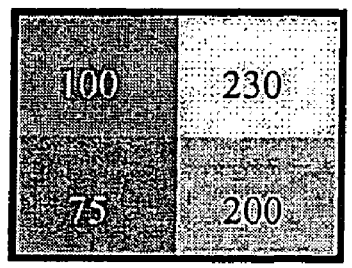
FIG. 3 is a drawing showing a 4 pixels image with 8 bit resolution.

Some images taken do not make use of the full resolution available. For example, an 8 bit image with no pixels that takes on the value of 0 and/or 255 does not take advantage of the full scale resolution offered by the 8 bits. By normalizing the pixel values, the full image resolution can be taken advantage of allowing for greater contrast. Take for example, an 8 bit image containing 4 pixels with values of 100, 230, 75, and 200 (FIG. 3). There is a clear edge within this image that separates it into right (large values) and left (small values) side. The contrast between the two halves of the image can be increased by normalizing the pixel values using the following equation:

$$P'(x,y)=(2^N-1)*[(P(x,y)-P_{min})/(P_{max}-P_{min})]$$

Figure 4:
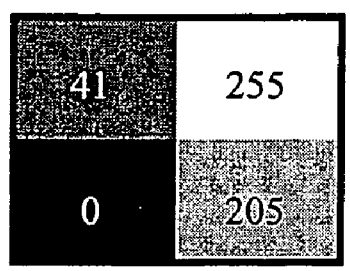
FIG. 4 is a drawing showing a normalized 4 pixel drawing.

Here P'(x,y) is the normalized pixel value calculated for location (x,y) using image resolution (N), the current pixel value at location (x,y), and the maximum and minimum pixel value within the image. The normalized pixel values are 41, 255, 0, and 205 with 41 at top left, 0 bottom left, 255 top right, and 205 bottom right (FIG. 4). There is now more contrast between the right and left side, allowing for easier processing.

A larger image contrast allows for easier edge detection and object identification through segmentation. For example, a grayscale image can be converted to a binary image through binary segmentation with a user-defined threshold. All pixels of value lower than that of the threshold are forced to zero (black); all pixels of value higher than the threshold are forced to 1 (white). This binary image can be used to quickly classify each pixel as being a member of one or two classes such as background or objects of interest.

Figure 5:
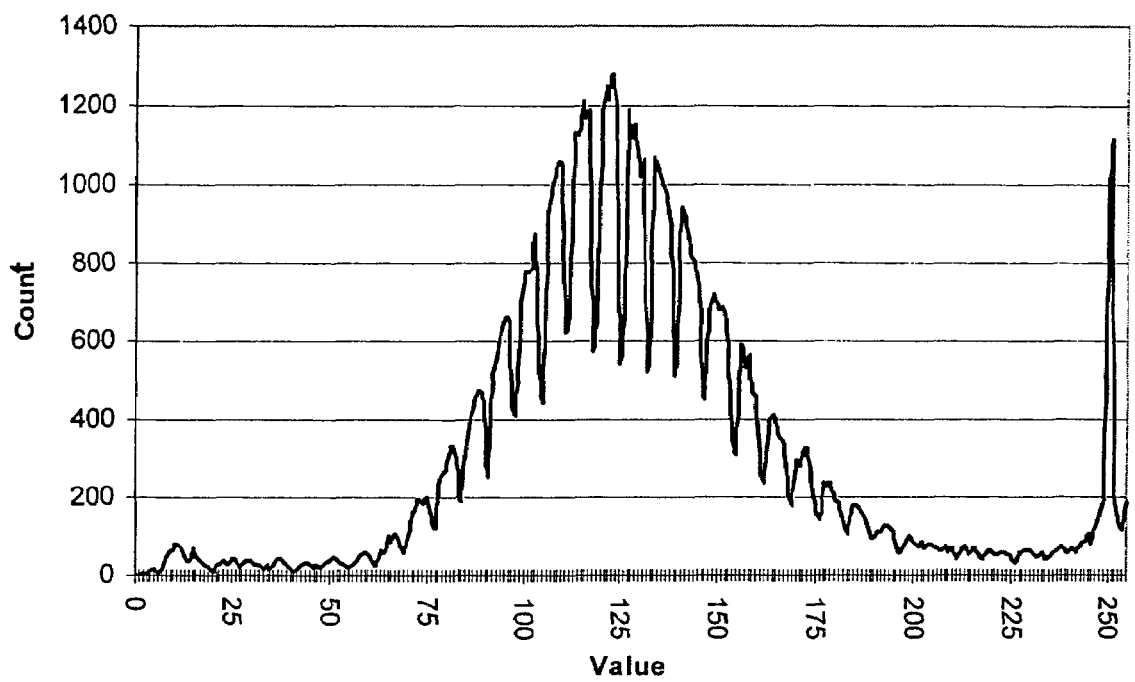
FIG. 5 a graph showing histogram data showing the frequency at which each pixel value occurs. Segmentation thresholds are generally selected where the frequency count dips drastically (i.e., about 70 and about 192).

Grayscale value frequency data provided by histograms offers valuable information when selecting segmentation thresholds. Thresholds for creating good binary images are often selected within values of the frequency data. Additionally, histograms inherently offer total and member class pixel counts (FIG. 5).

If any of these processing techniques are to be applied only to a select region of interest (ROI), a mask must be applied to the image. Like a stencil, a mask covers any part of an image to be ignored and exposes the area to be viewed, studied, modified, etc. Mask application allows for focusing the processing time and efforts only of the region of interest.

National Instruments' LabVIEW is a development suite based on the G programming language for easily creating software for signal, data, and image acquisition and processing (LabVIEW User Manual, 2004). Through a drag and drop process users are able to quickly create their own graphical user interfaces (GUIs) and code. Each file created is known as a Virtual Instrument (VI) and a VI embedded inside another VI is called a subVI. The creation of subVIs is crucial to creating easily scalable and readable code.

Every VI is comprised of two parts, the front panel and the Block Diagram. The Front Panel is where the user interface is created. Knobs, gauges, sliders, graphs, etc. are created by simply dragging, dropping, and resizing them on the Front Panel. For each control and indicator created on the Front Panel, a node is automatically created for it in the block diagram. The Block Diagram contains the code for the VI. Like the Front Panel, each function is placed within the Block Diagram through a drag and drop process. It is possible to create nodes which contain text based code.

A wide variety of extra functionalities can be added to the base LabVIEW installation through add-ons. Some add-on packages can include analysis, connectivity, motion control, control design, personal digital assistant (PDA), and application building toolkits. Additionally, National Instruments offers a Vision Development Module for image processing tasks (currently not ported for PDA's). The Visional Development Module allows a user to easily incorporate masking, normalizing, segmentation, and image histograms into a VI.

The software created using LabVIEW 6.1 and Peter Parente's LabVIEW WebCam Library gives a user the power to perform several tasks related to observing and analyzing insect crowding behavior including: taking single snapshots, capturing time stamped pictures, extracting time variant information from still pictures using image processing, and capturing and analyzing insect behavior in real-time.

Figure 6:
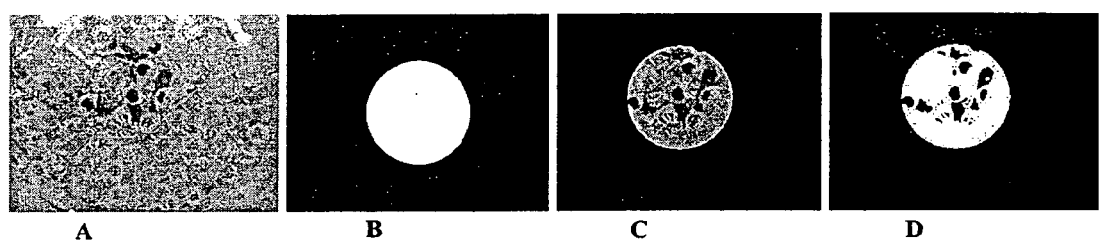
FIG. 6 is a sequence of photographs showing an image processing sequence. The portion of FIG. 6 designated "A" is the original image which is then masked with a 320×240 pixel mask of the users choice shown in the portion of FIG. 6 designated "B". The mask is given an offset to select a region of interest for processing as shown in the portion of FIG. 6 designated "C". The value of the pixels within the region of interest is normalized and then processed using binary segmentation as shown in the portion of FIG. 6 designated "D".
Figure 7:
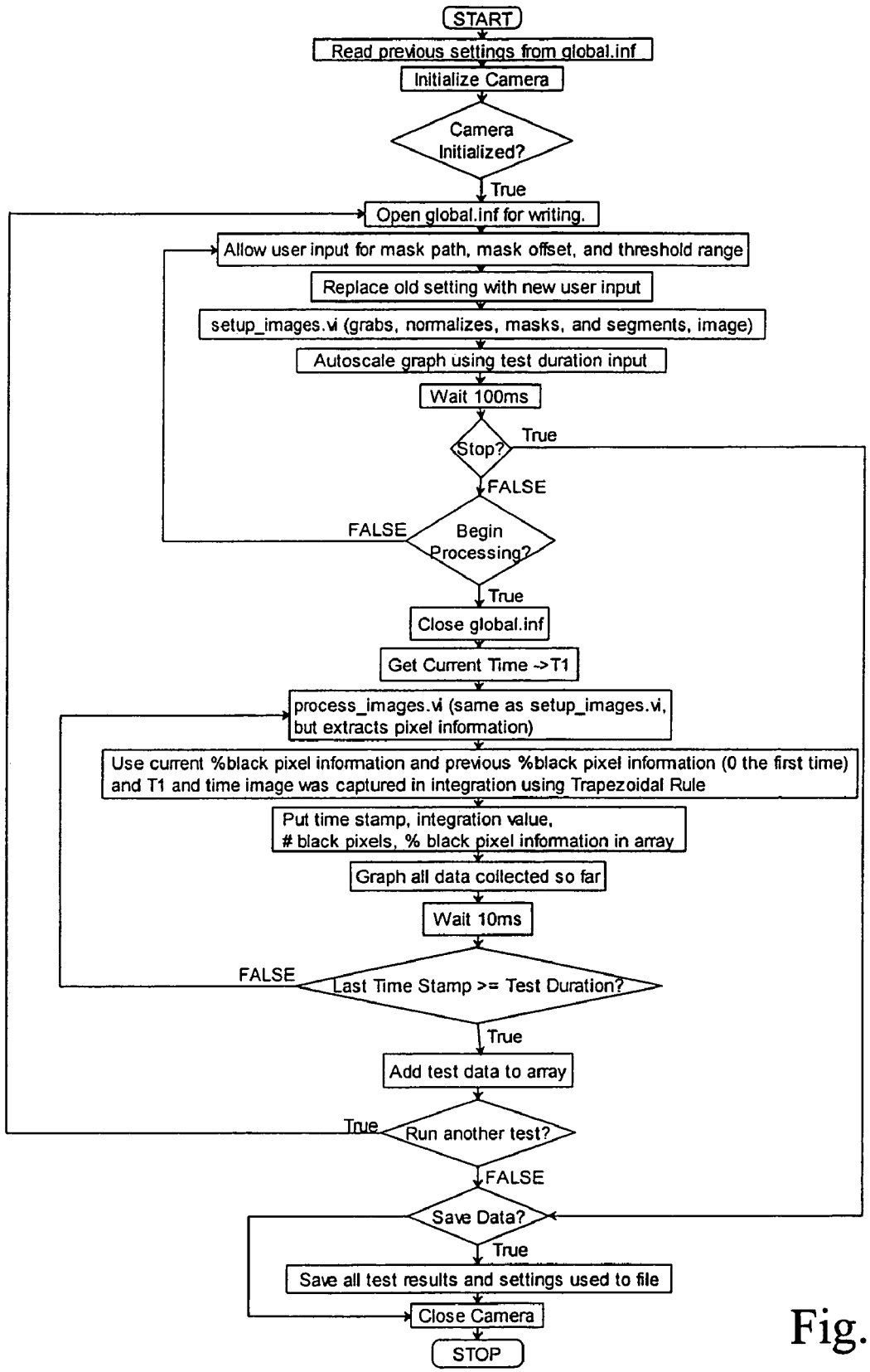
FIG. 7 is a flow diagram of the Real-Time.VI.
Figure 8A:
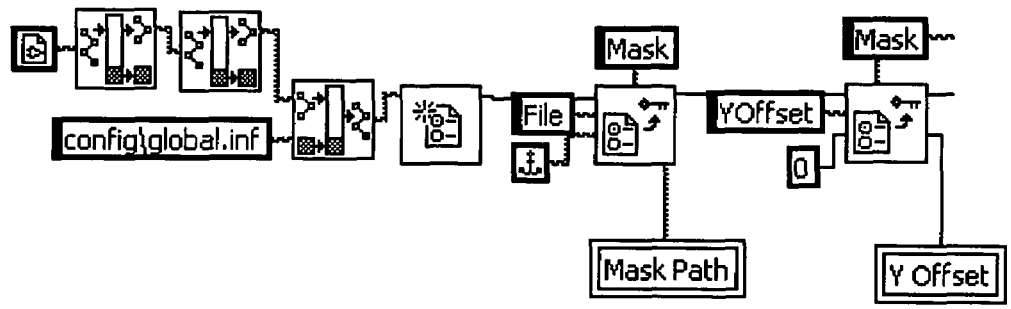
Figure 8:
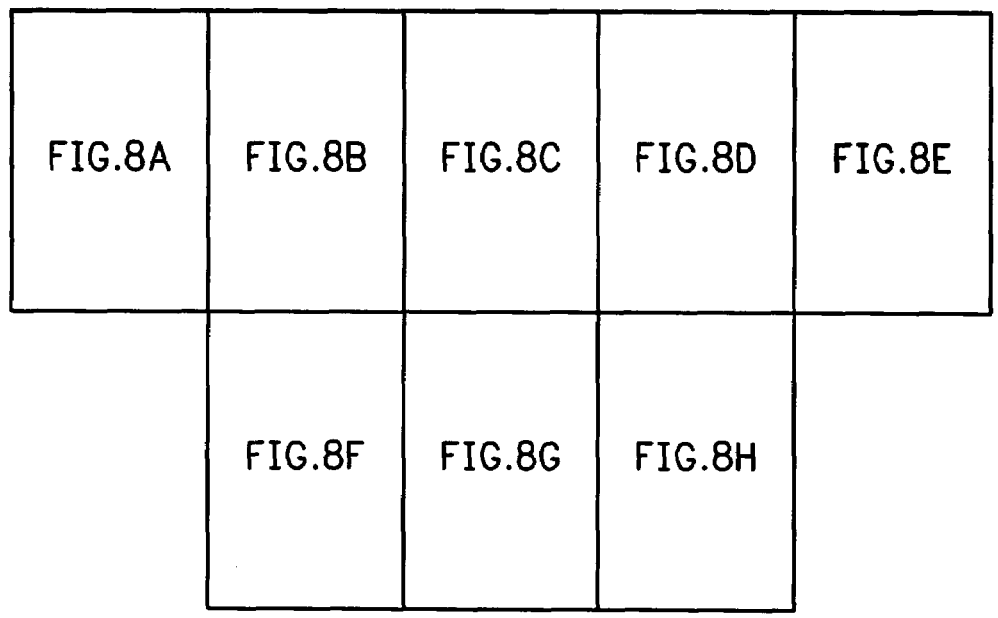
Figure 8C:
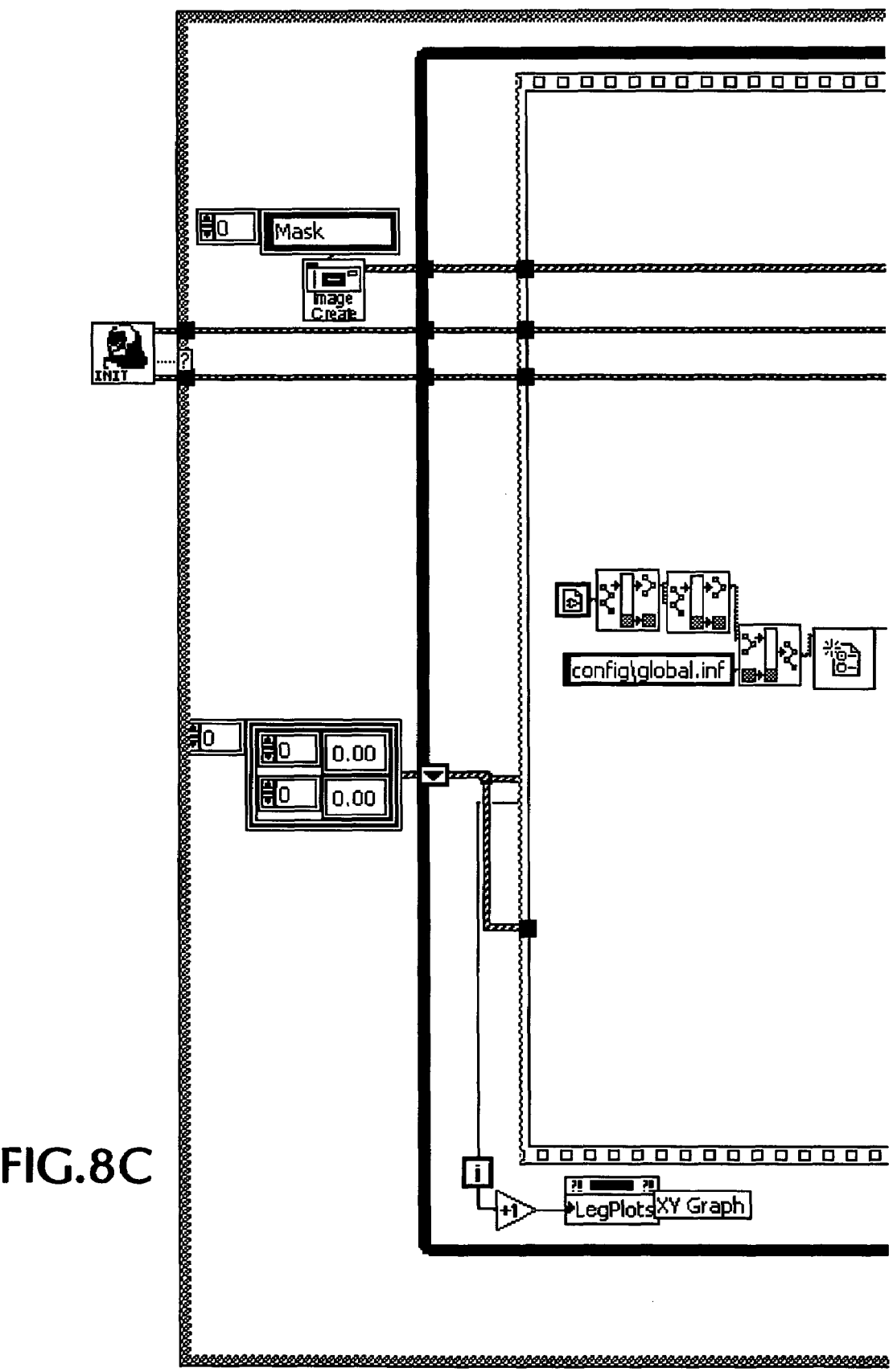
Figure 8D:
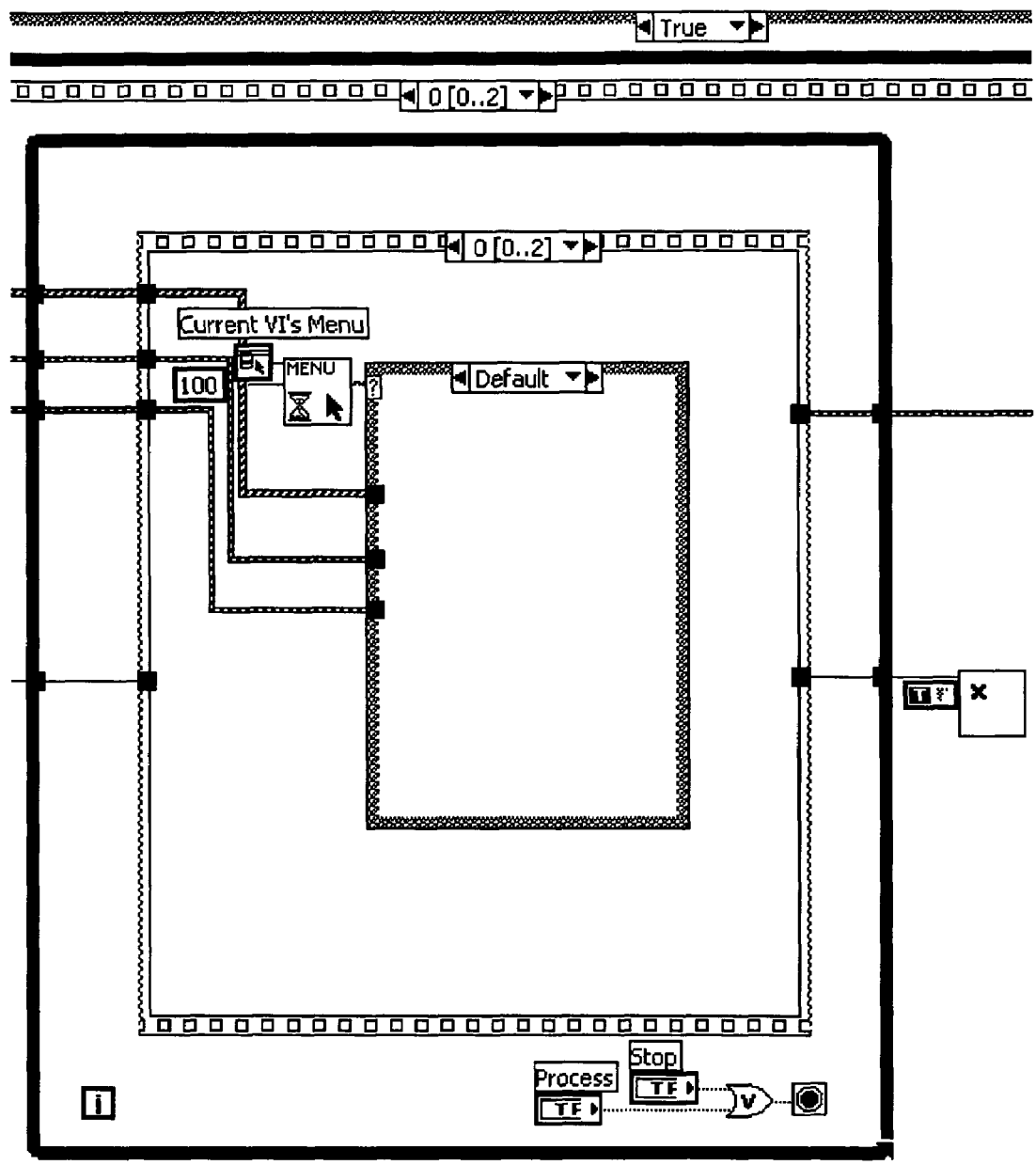
Figure 8E:
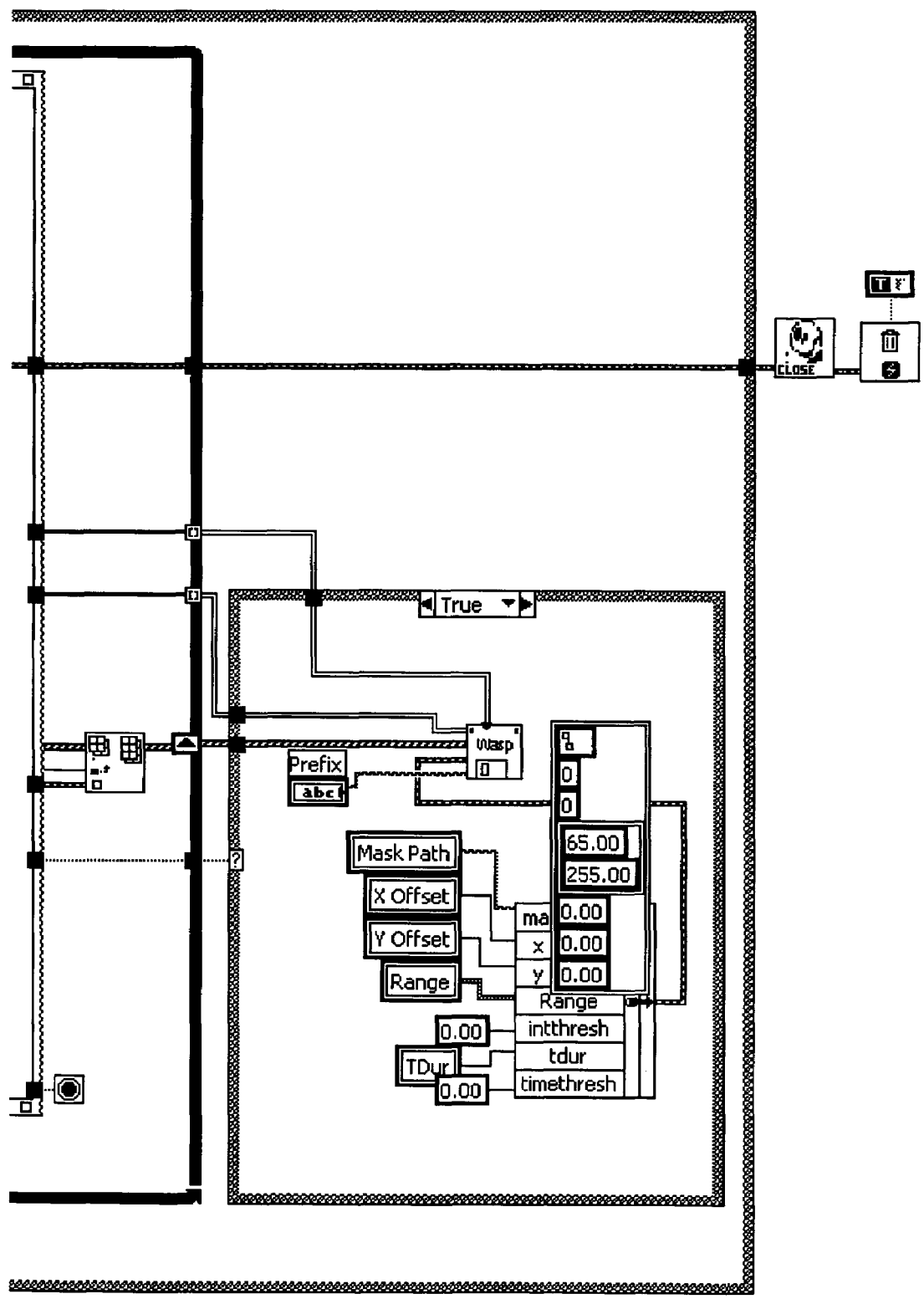
Figure 8F:
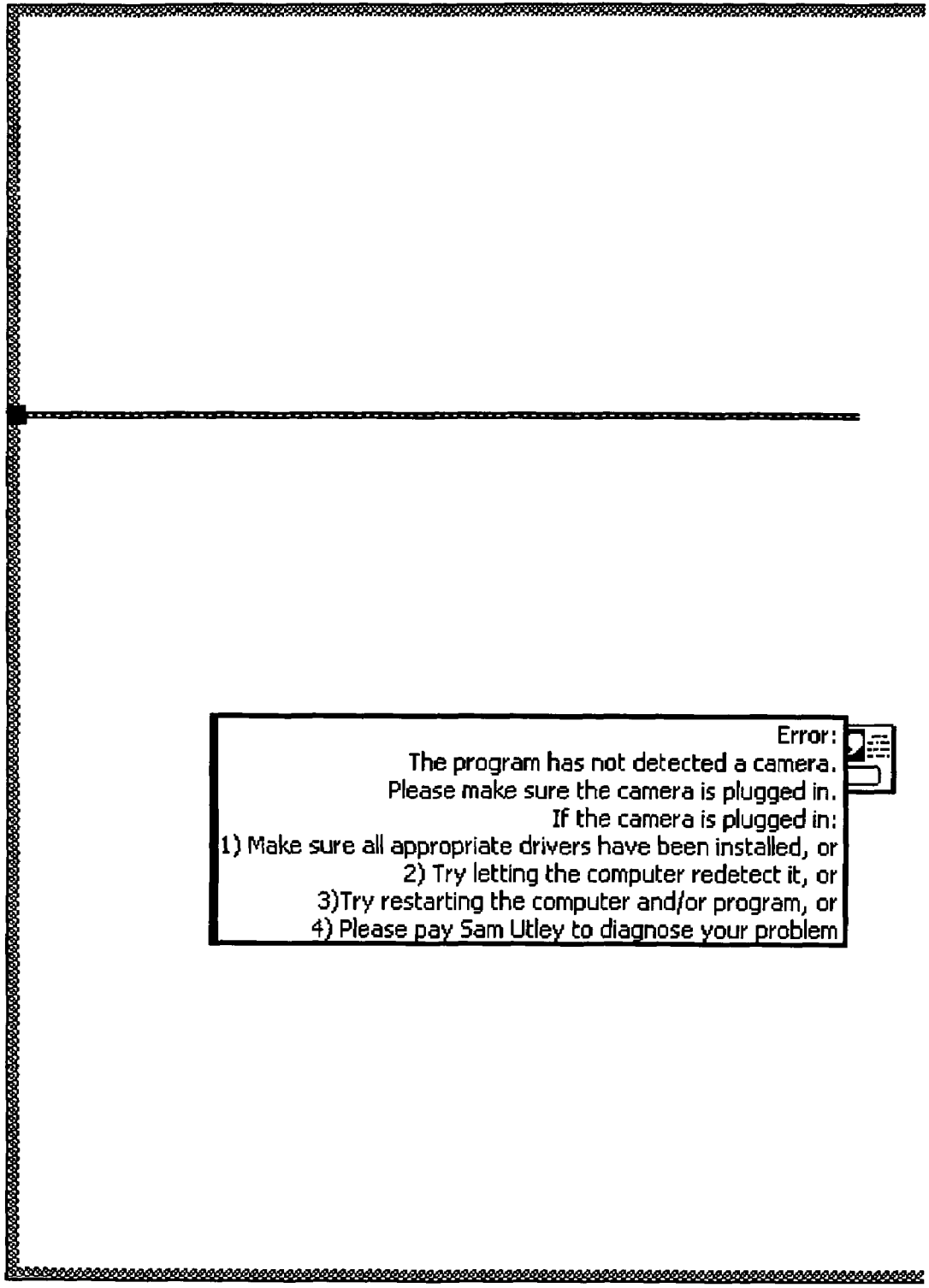
Figure 8H:
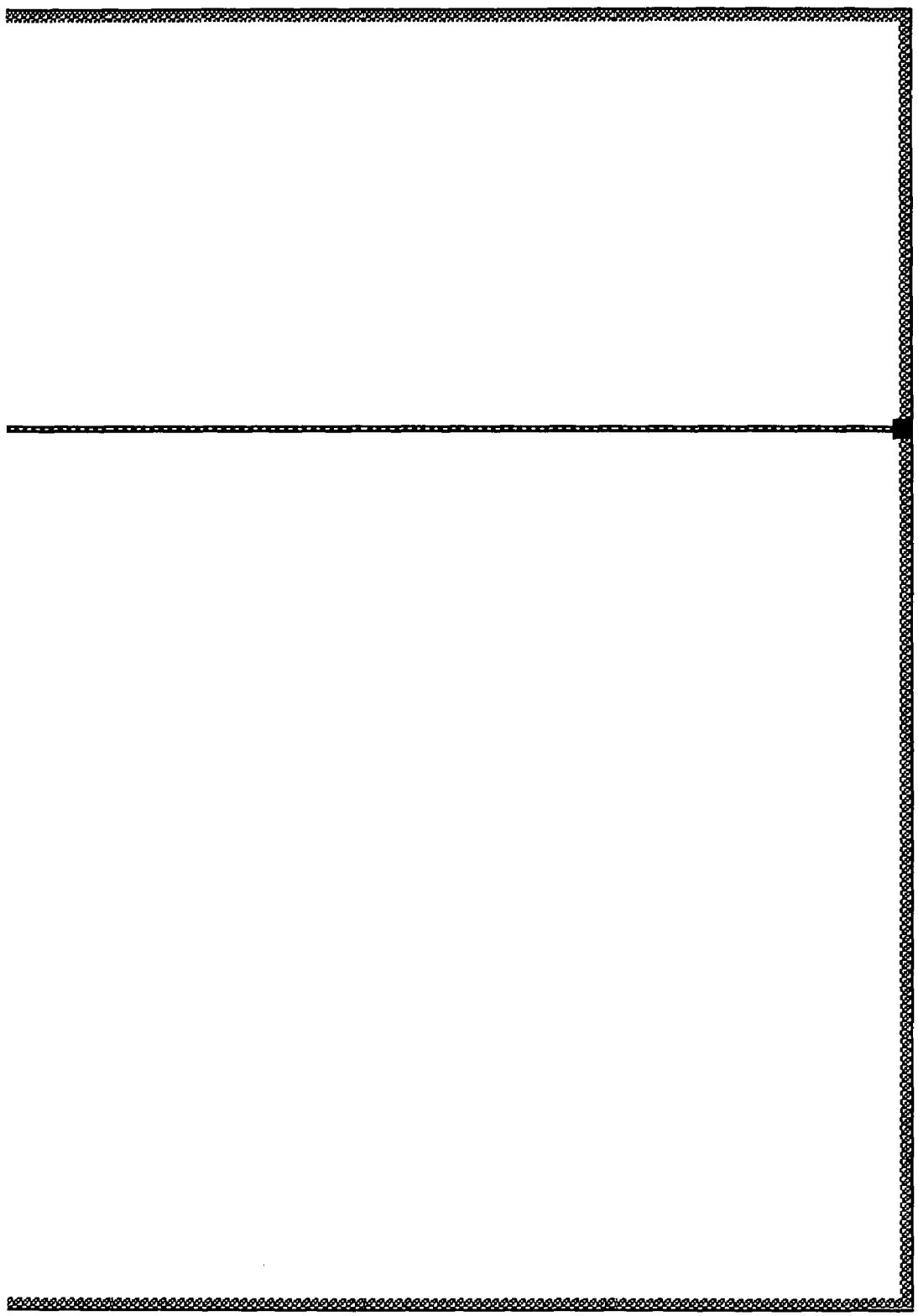
Figure 9A:
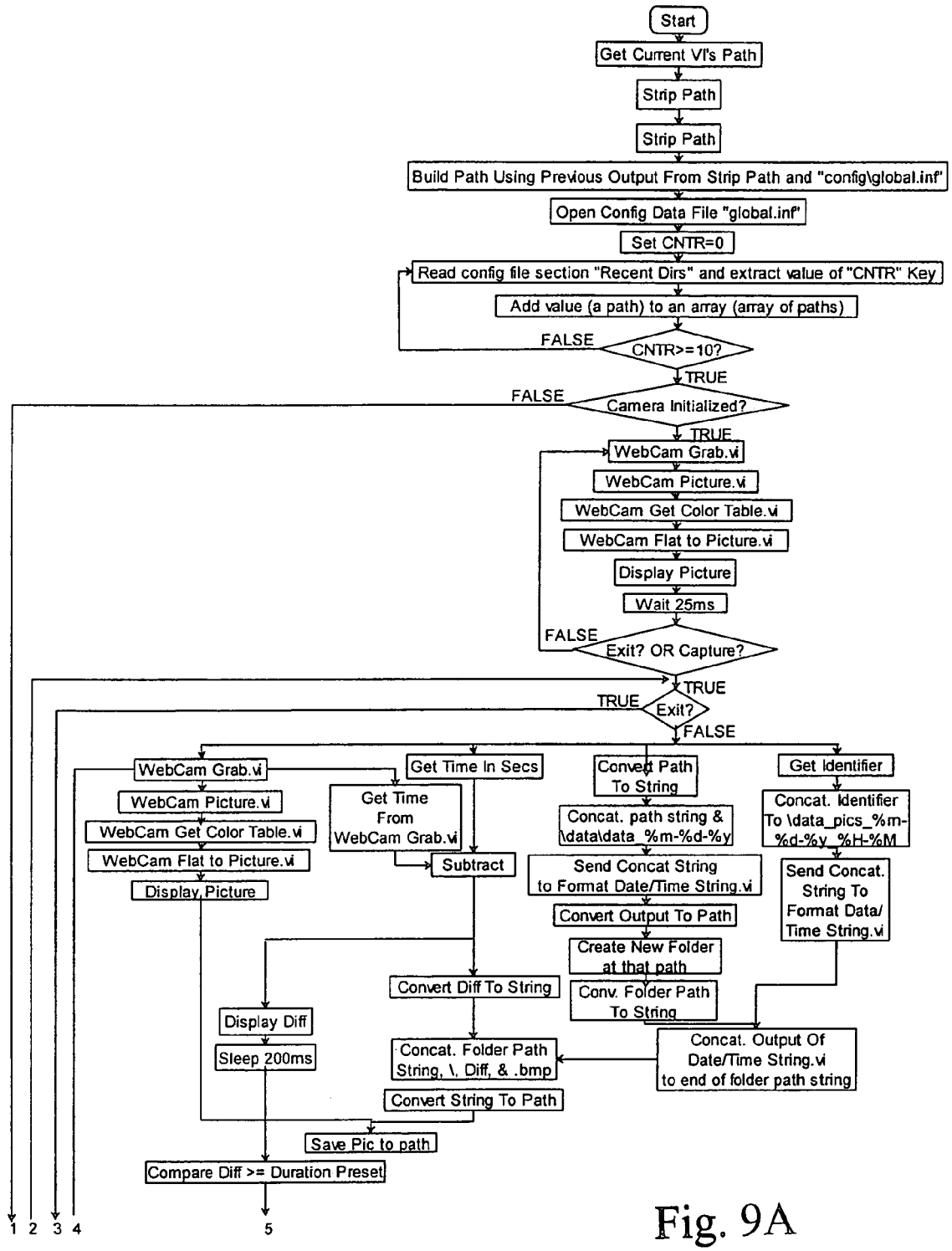
FIGS. 9A-9B is a drawing showing the Capture-Stills.VI Flow diagram.
Figure 9B:
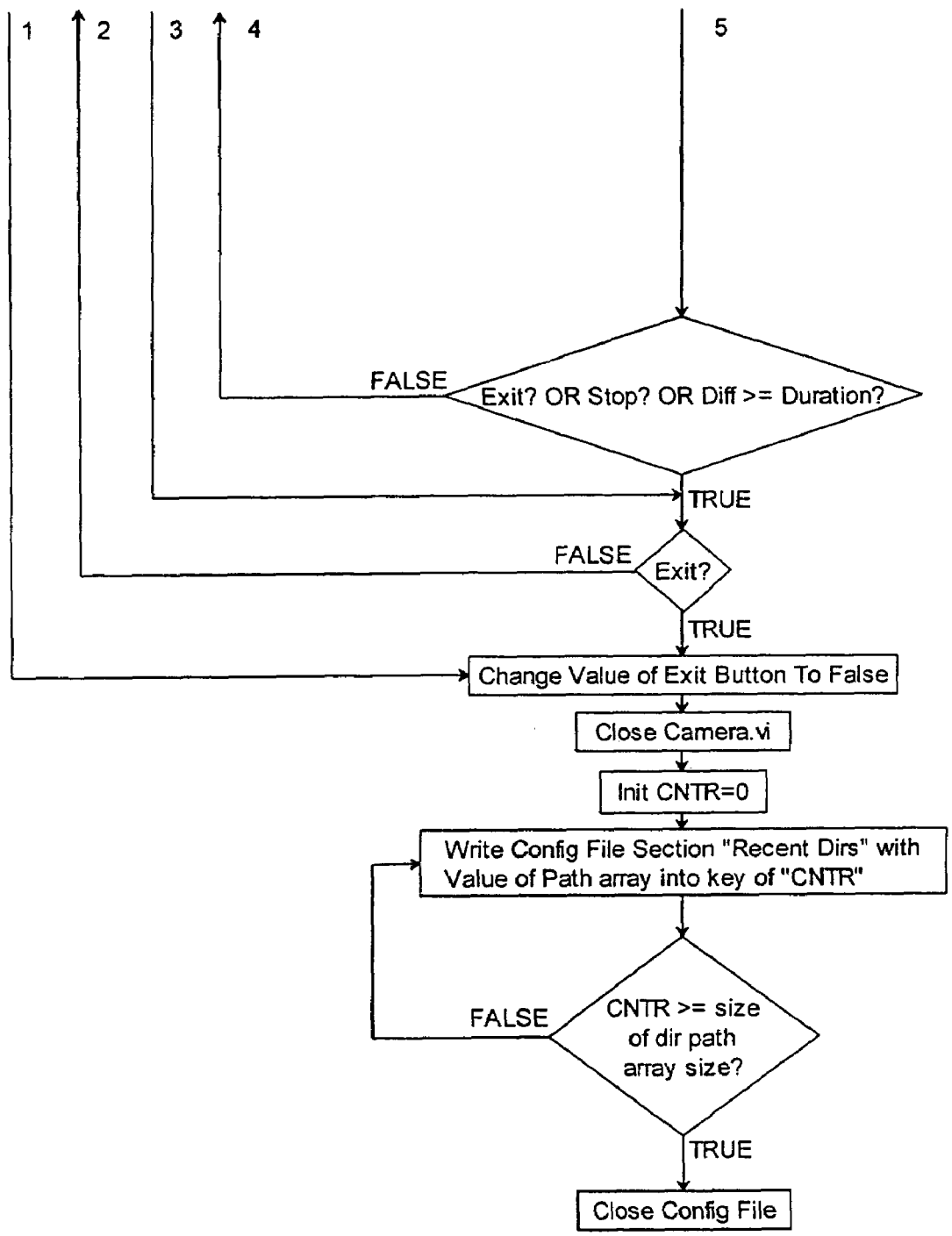
Figure 10:
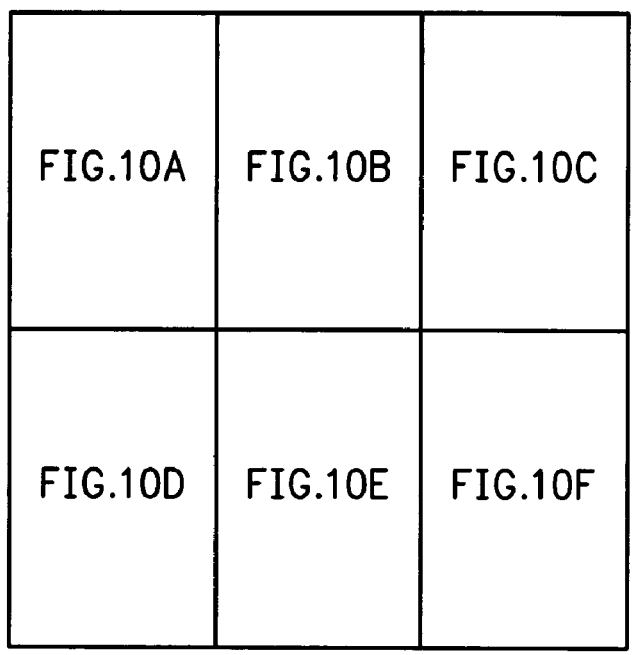
Figure 10B:
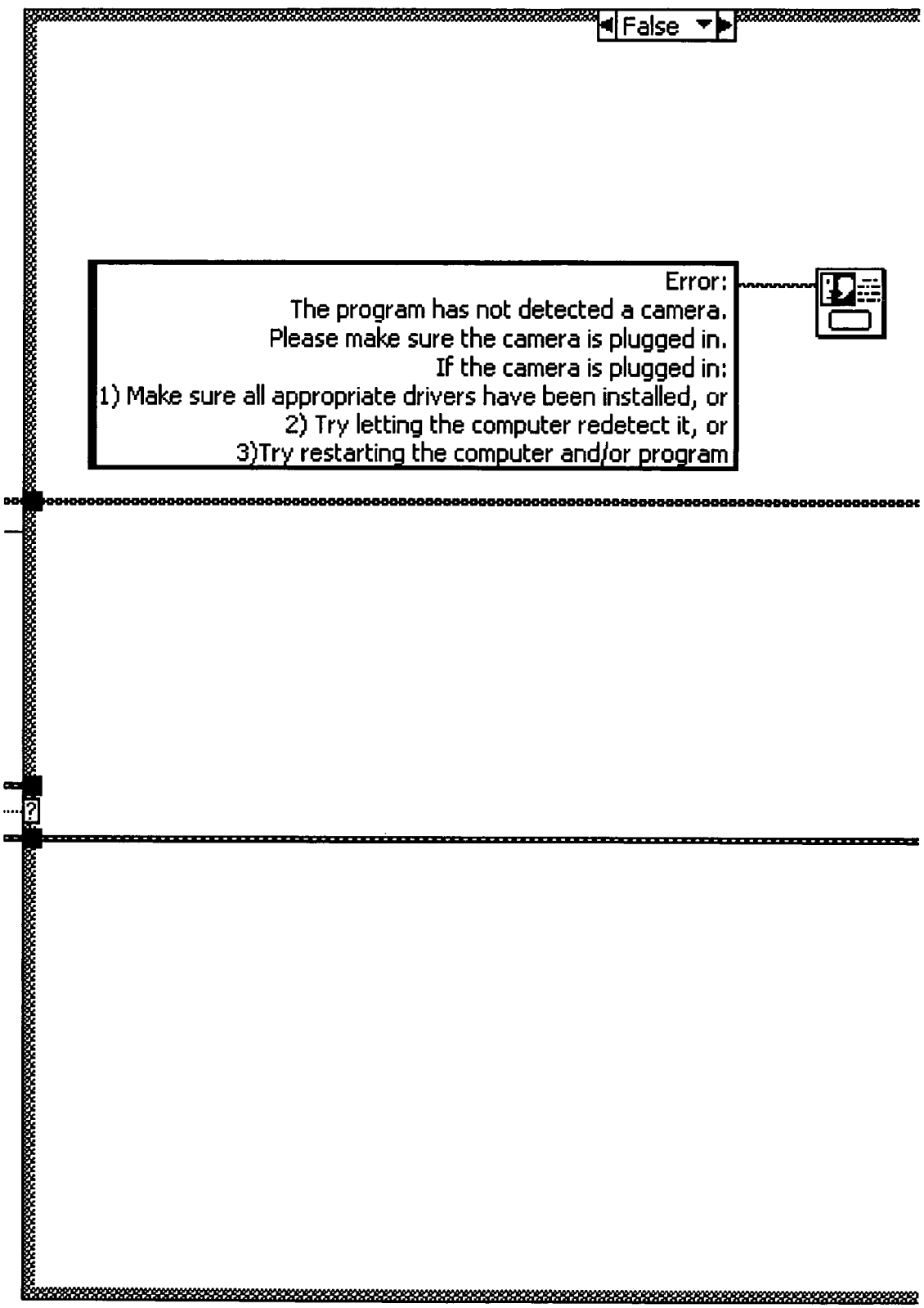
Figure 10C:
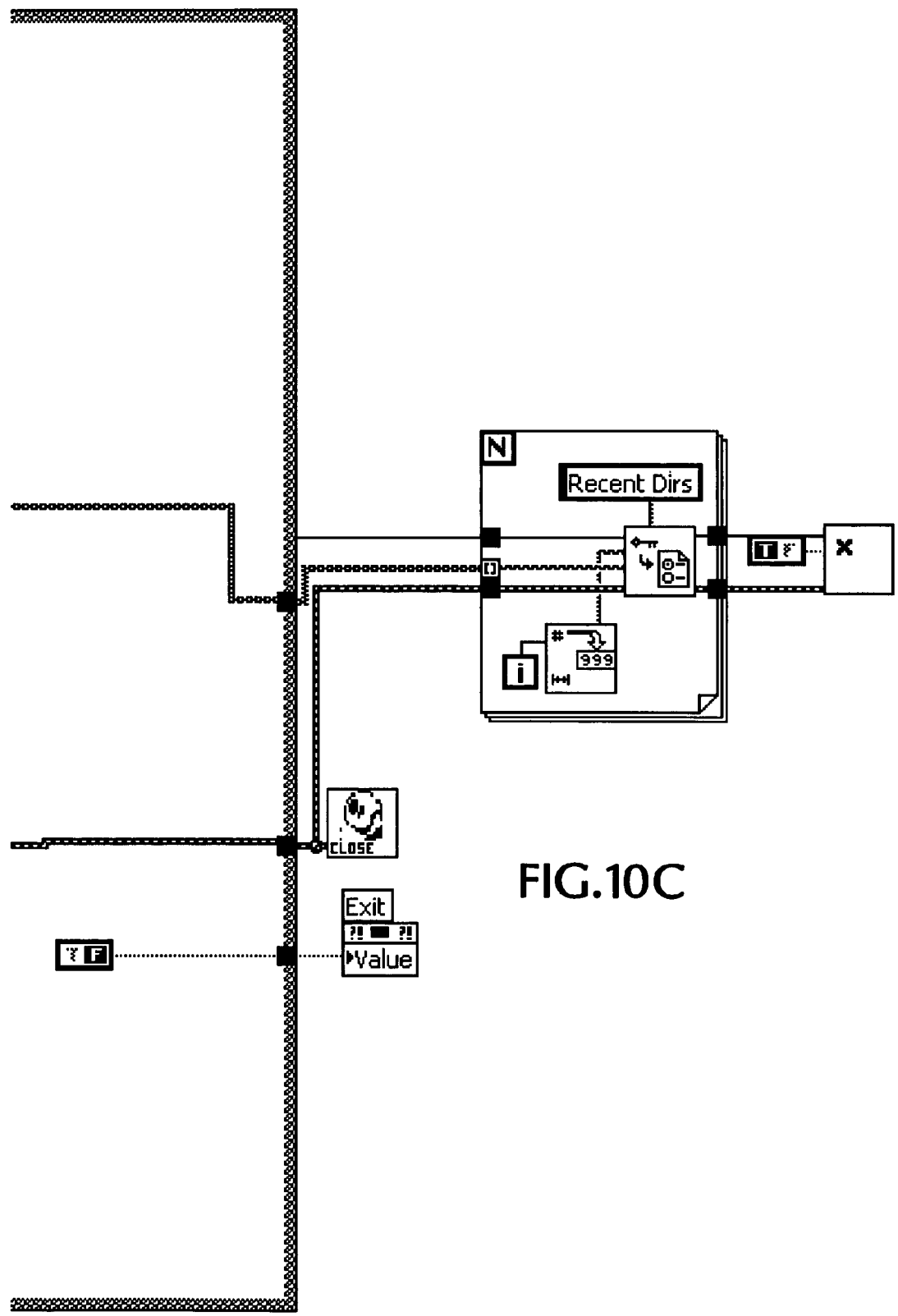
Figure 10D:
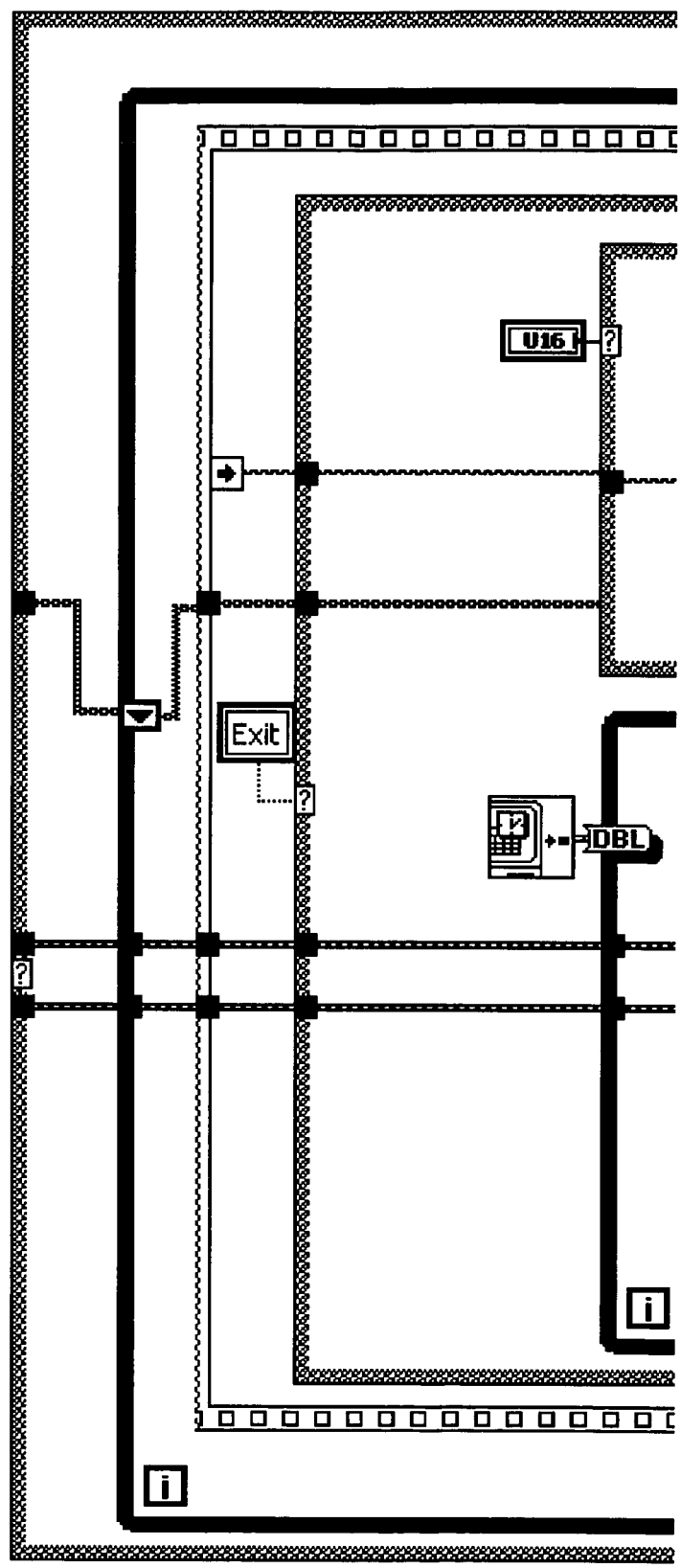
Figure 10E:
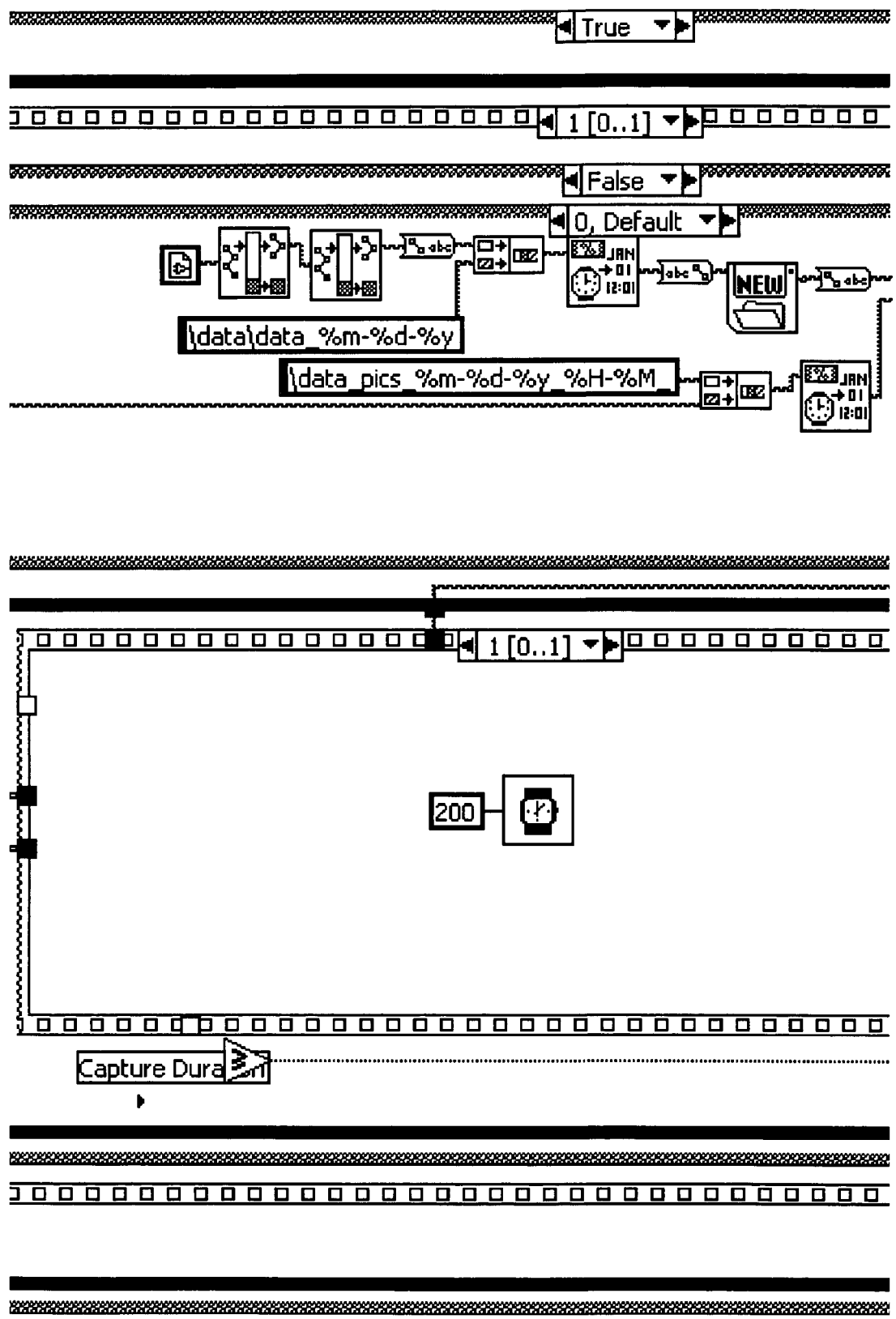
Figure 10F:
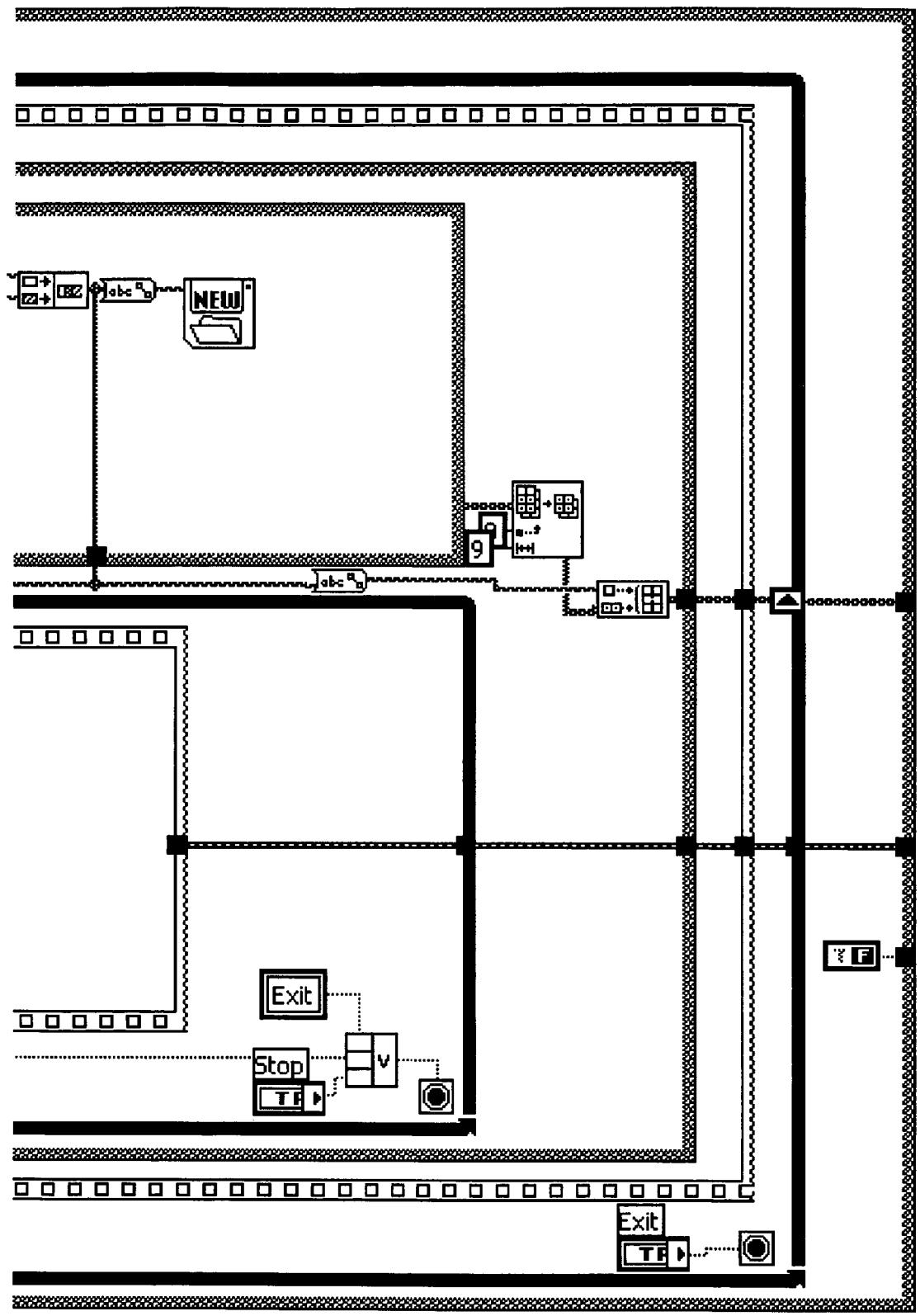
Figure 10:
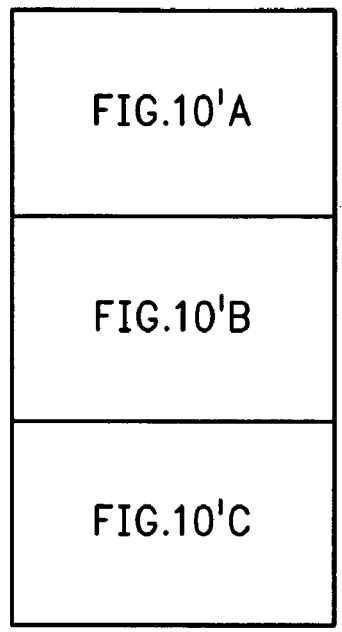
Figure 11A:
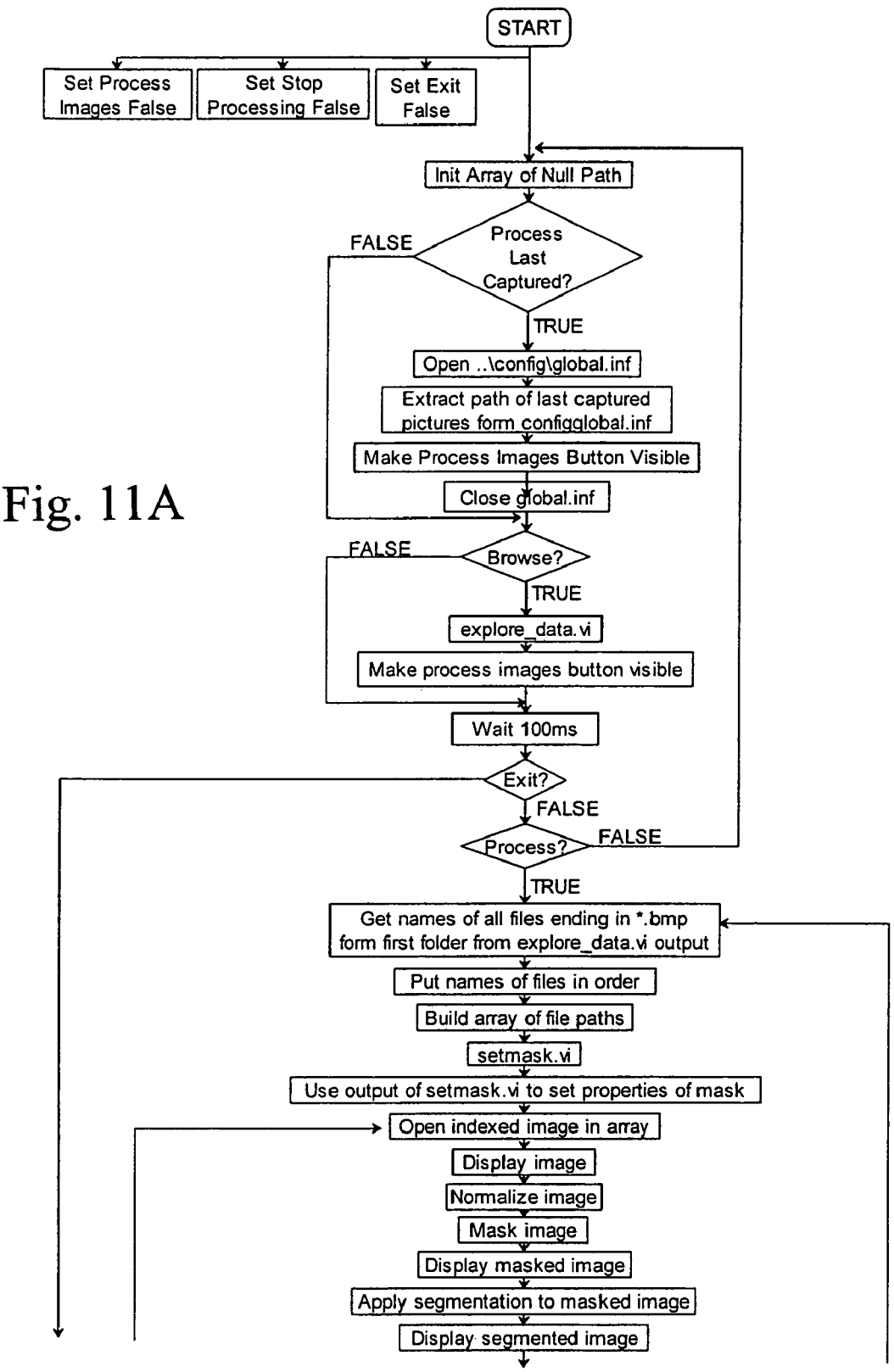
FIGS. 11A-11B is a drawing showing the Process-Still.VI Flow Diagram.
Figure 11B:
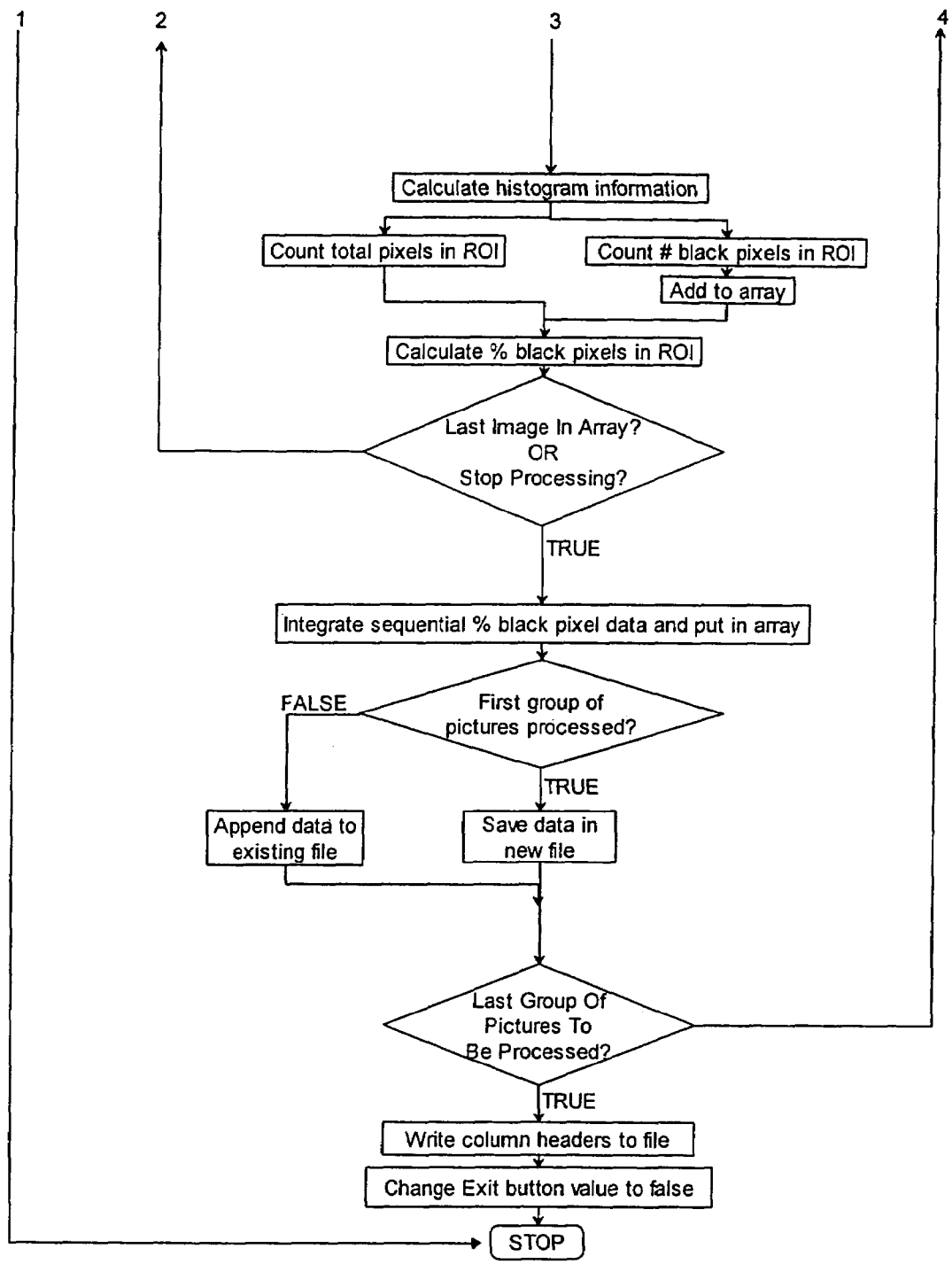
Figure 12A:
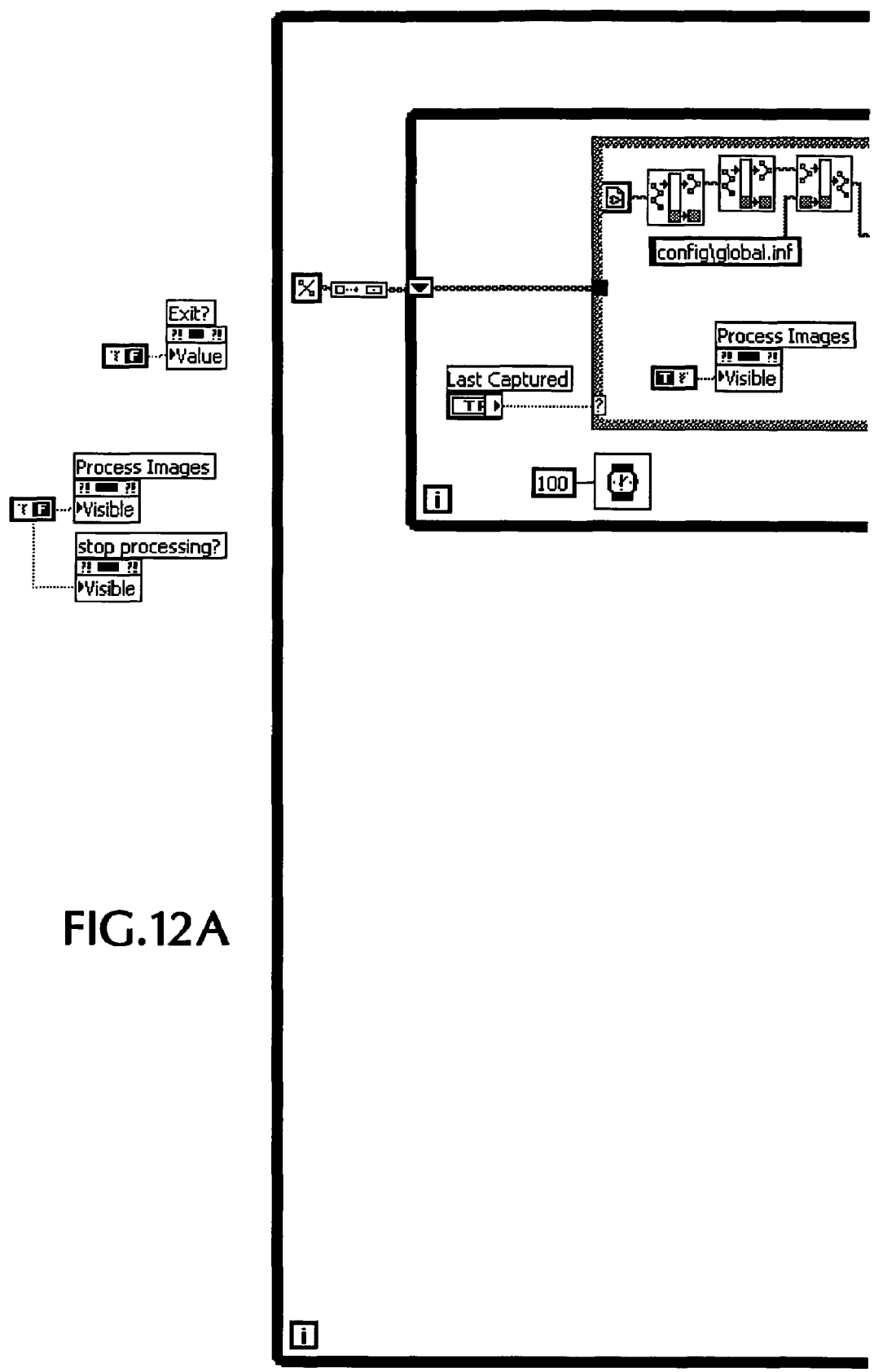
FIGS. 12 and 12A-12P are drawings is a drawing showing the Process-Stills.VI LabVIEW Block Diagram.
Figure 12B:
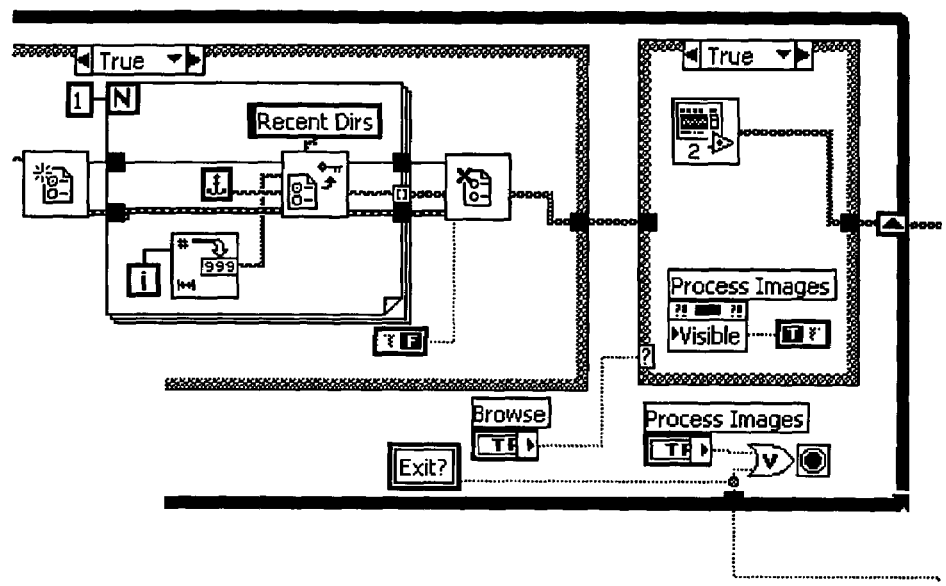
Figure 12C:
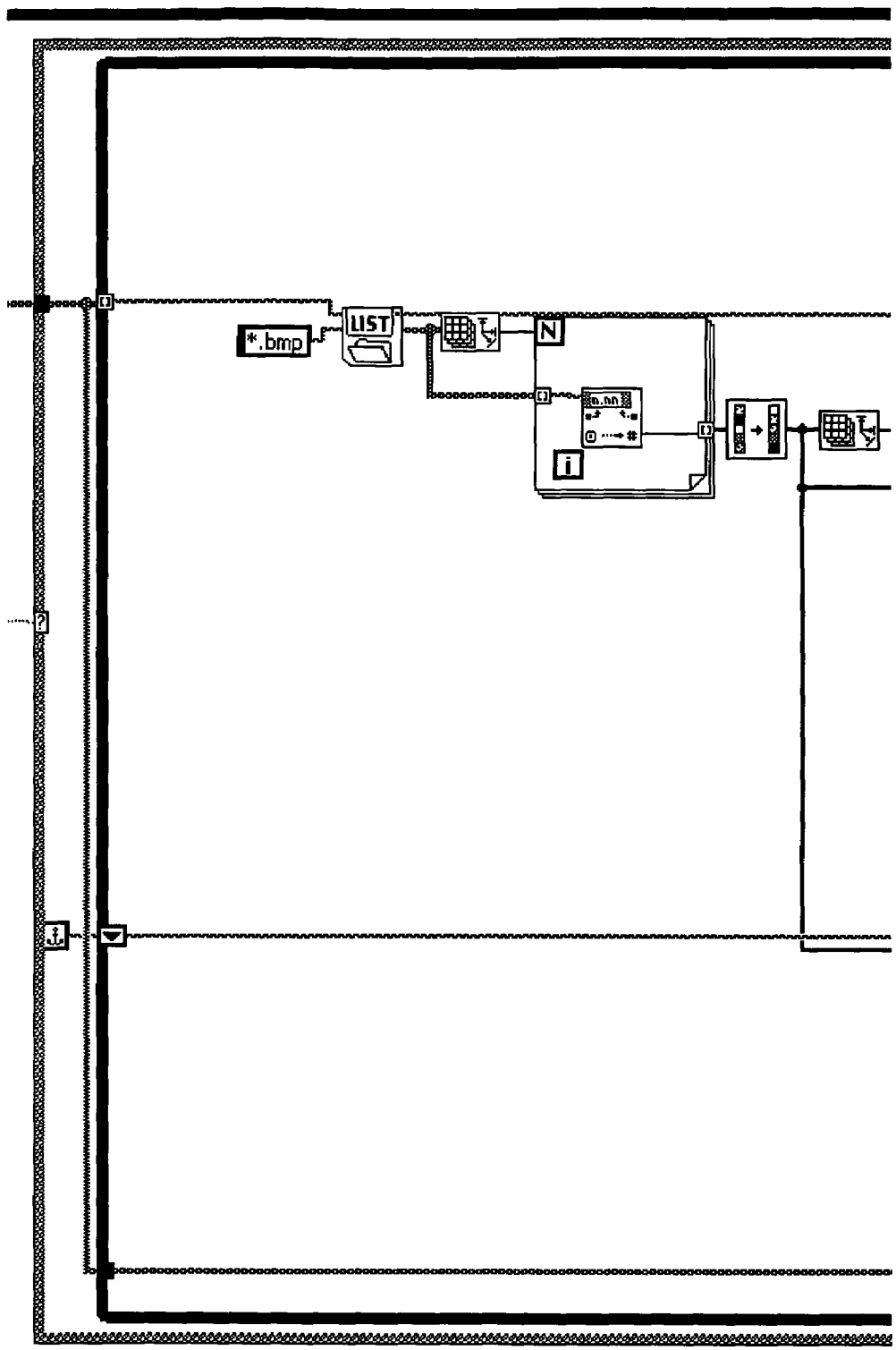
Figure 12D:
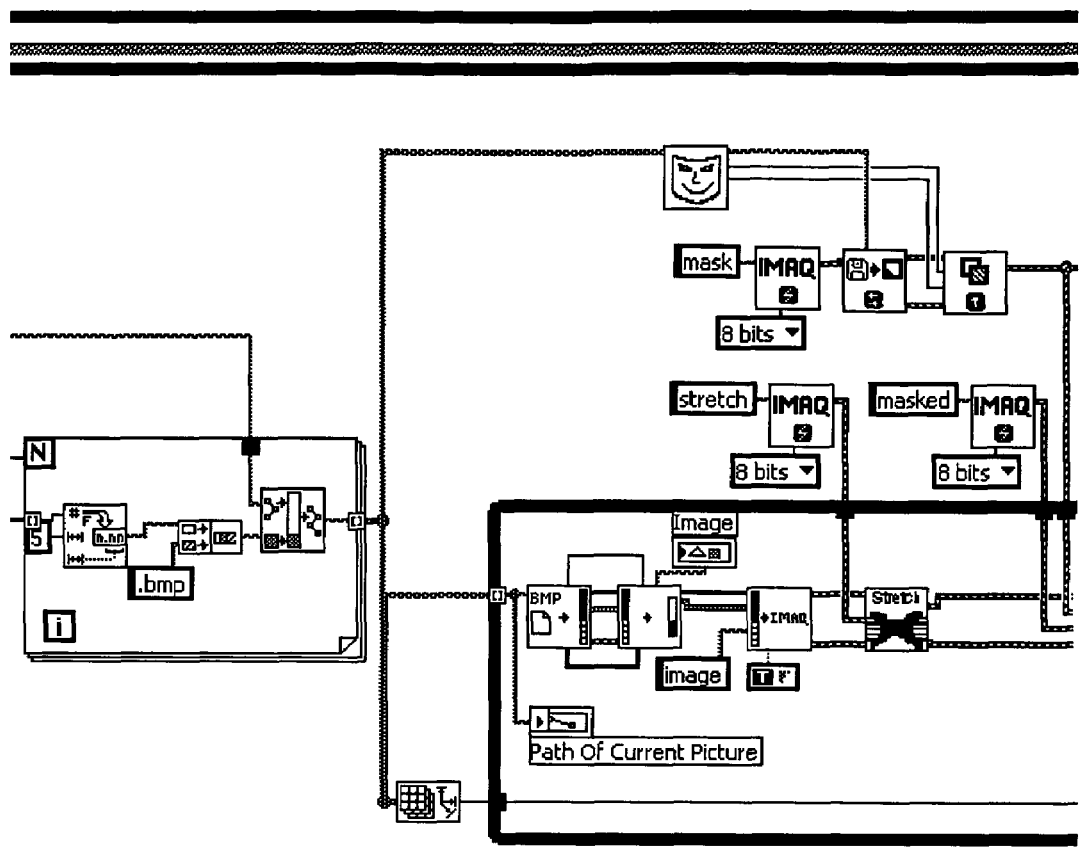
Figure 12E:
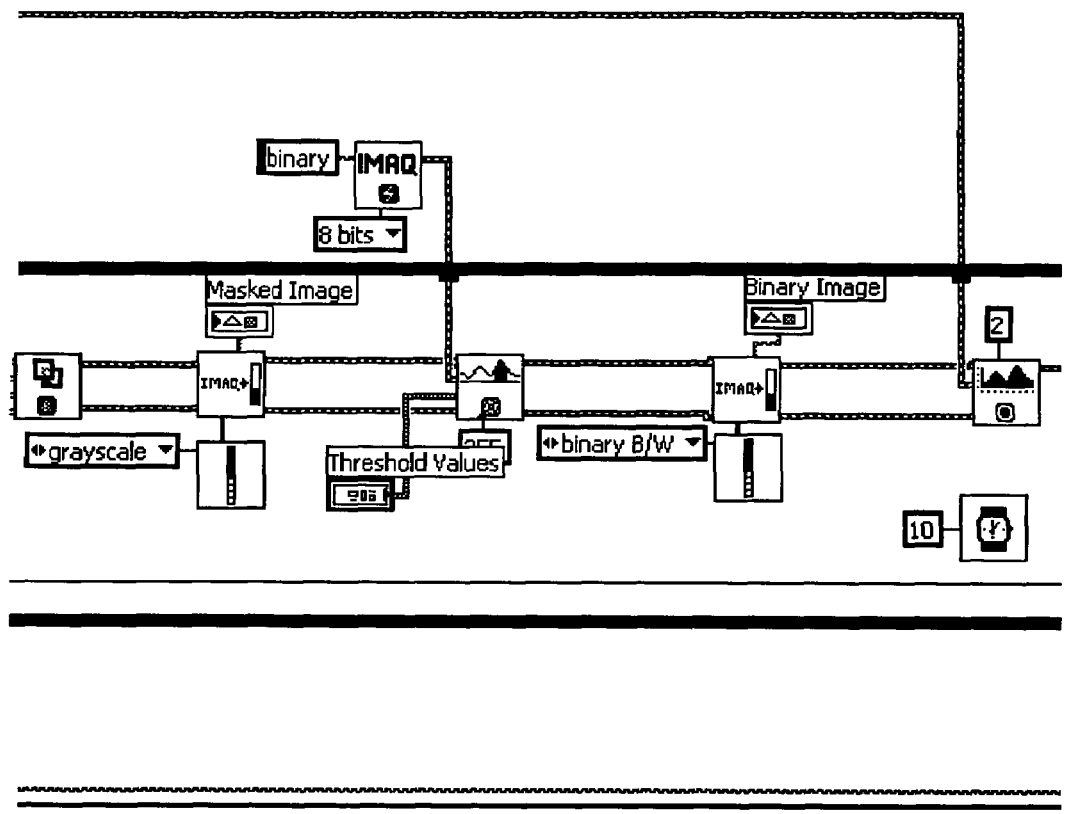
Figure 12F:
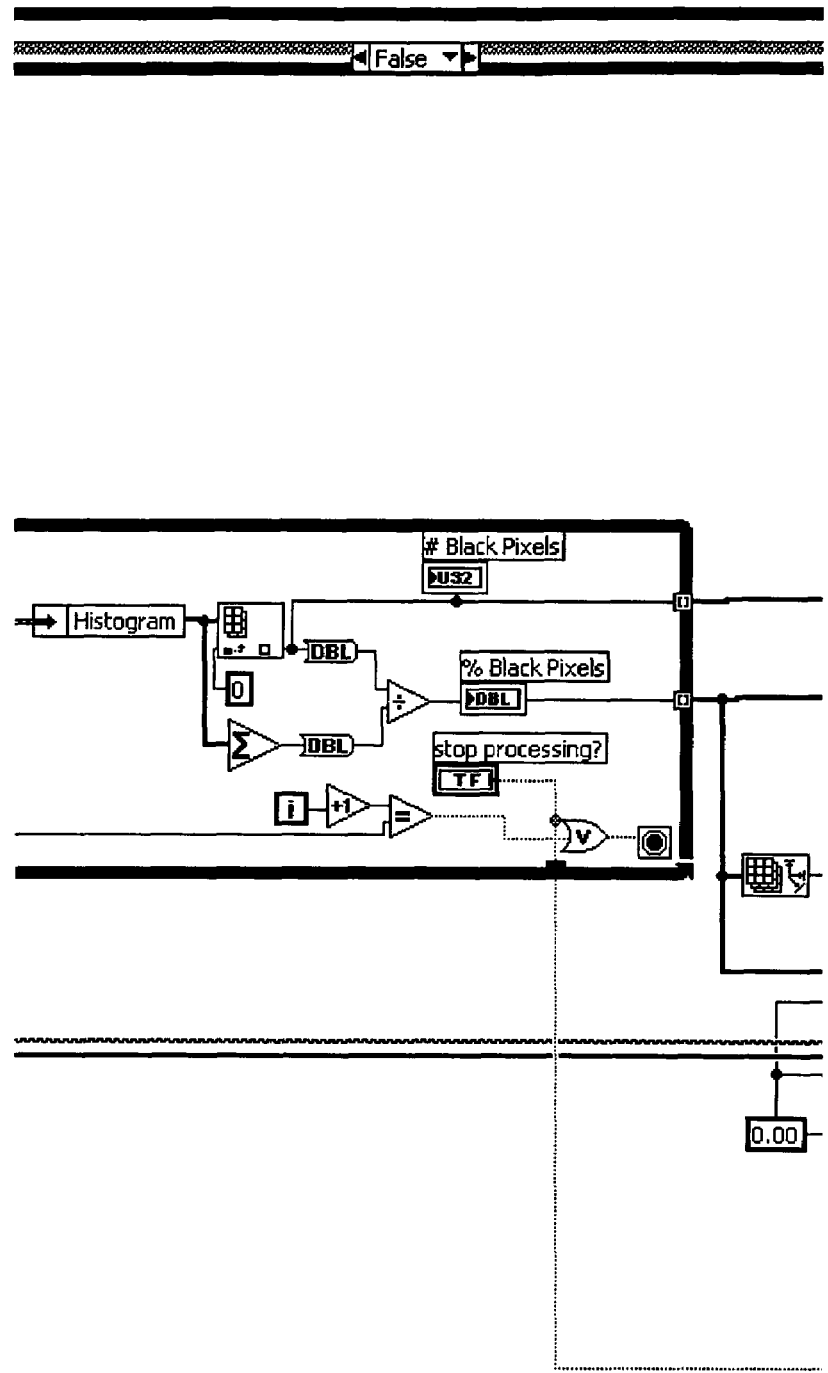
Figure 12G:
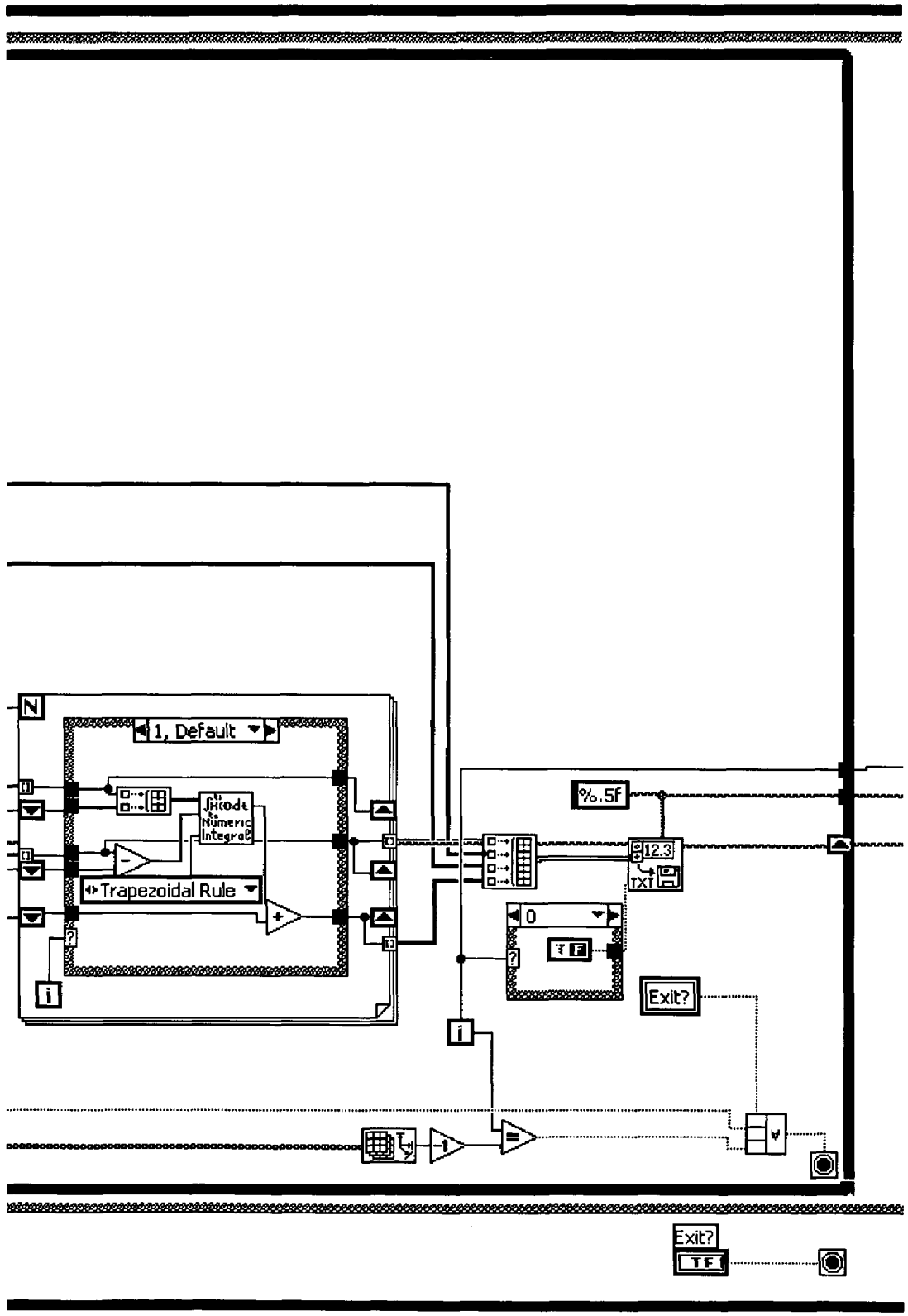
Figure 12H:
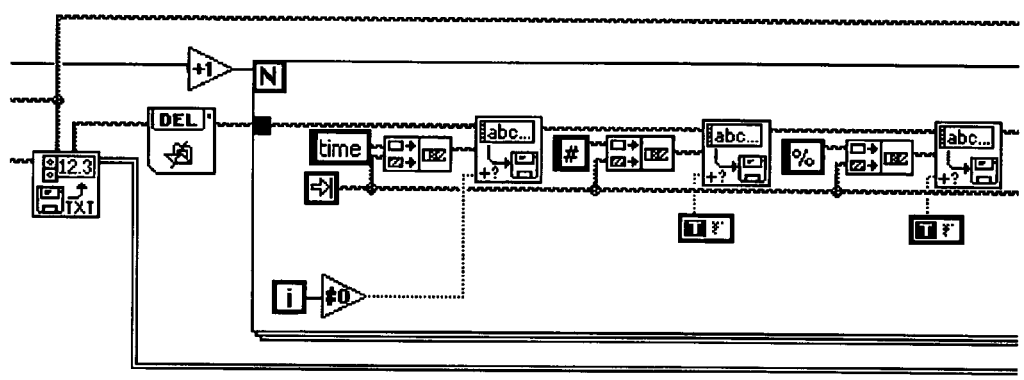
Figure 12I:
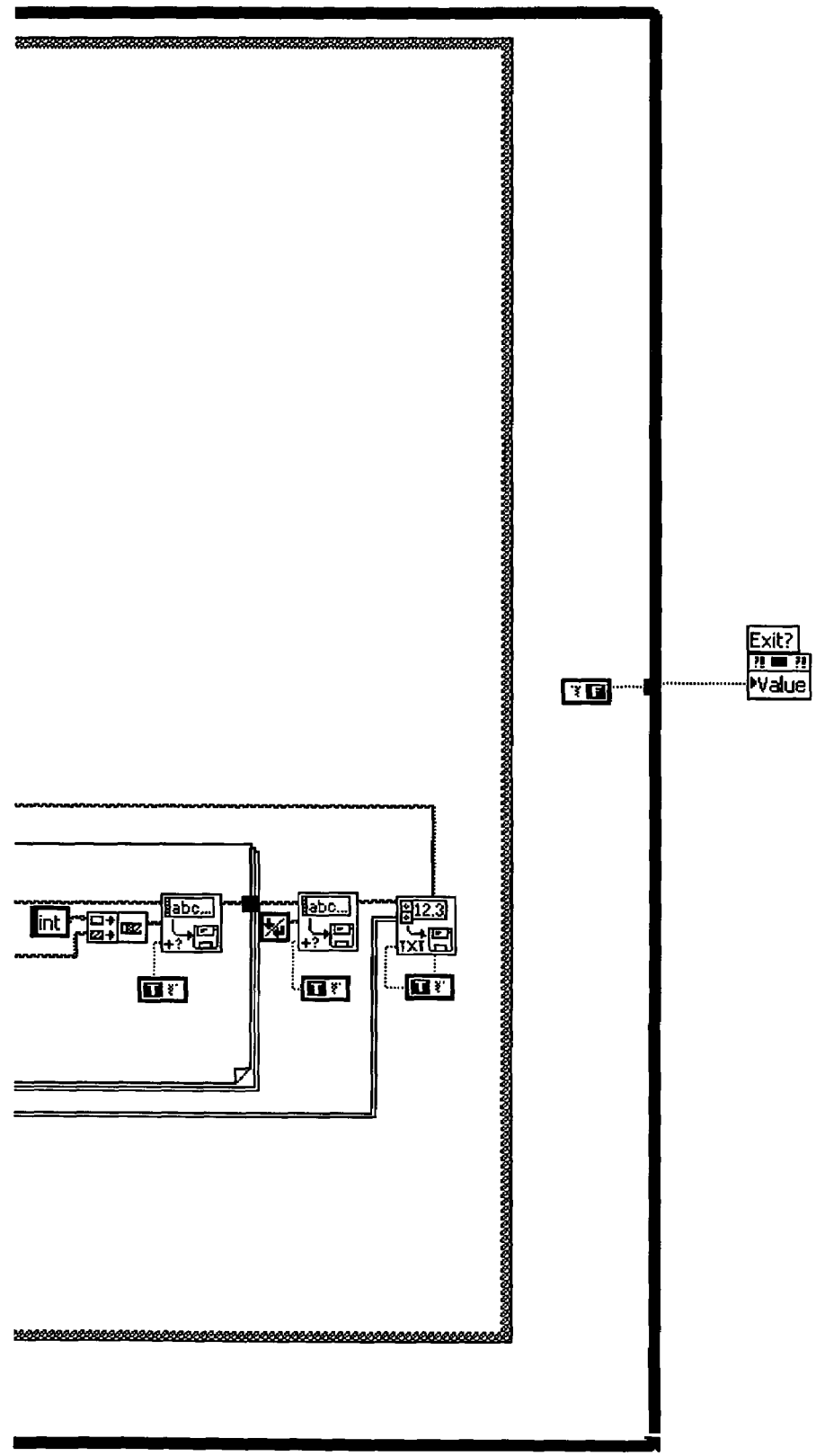
Figure 12J:
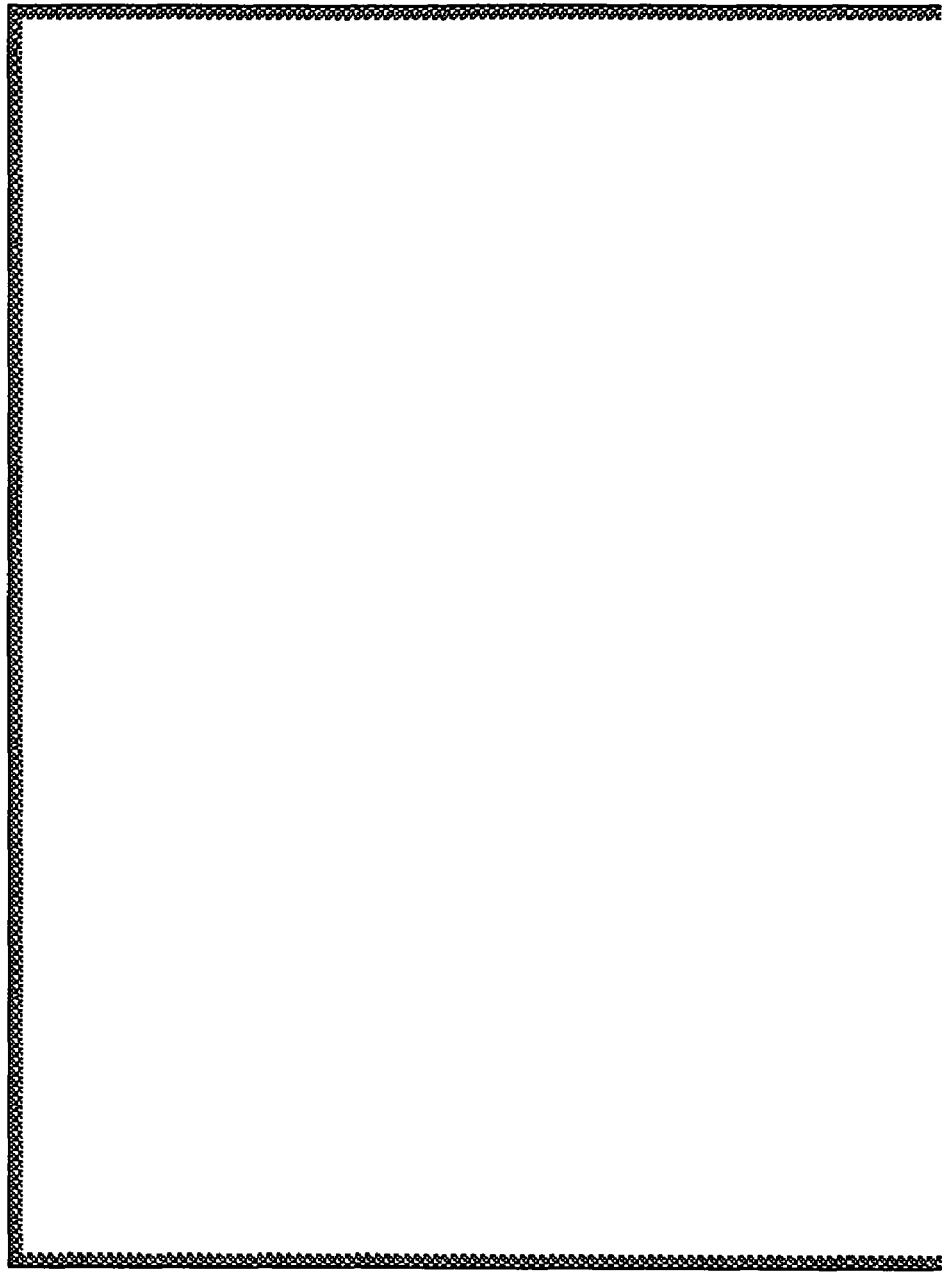
Figure 12P:

There are several basic image manipulation and analysis techniques forming the core process that allows the software to analyze the crowding behavior of insects. These techniques include masking, normalizing, creating histograms, and binary segmentation as discussed above. The core process is utilized in both time stamped and real-time image processing features. The captured image is first masked using a 320×240 pixel mask of the user's choice in order to select the region of interest (FIG. 6). The pixel data within the region of interest is normalized and segmented resulting in a binary image. The amount of black pixels within the region of interest are counted and divided by the total number of pixels within the region of interest. The time variant percent black pixel data is integrated using the Trapezoidal Rule (Equation 2) to produce time variant integration curves.

$$I_1 = I_0 + \frac{h}{2}(y_0 + y_1)$$

$I_1$=Current Integration Value
$I_0$=Previous Integration Value
h=Current time ($t_1$)–previous time ($t_0$)
$y_1$=% Black pixel value for $t_1$
$y_0$=% Black pixel value for $t_0$ The integration filters the data allowing for easier interpretation of the image analysis results.

For immediate results, a user utilizes the real-time image analysis sub-VI. This sub-VI allows a user to capture and process images in real-time. The activity is quantified and displayed graphically on screen. At this point, the user is left to manually input positive response conditions; however incorporation of a calibration routine to automatically determine those conditions can be added. When a positive response is recognized, the user is alerted (See FIGS. 7 and 8a-8c).

To record the organism behavior and analyze it later, there is a sub-VI for capturing time-stamped still shots of the organisms every about 250 milliseconds (some variation is present in the capture interval lengths due to computer latency). The directory of images are recorded and saved in a global.inf file. The last 10 directories are recorded (FIGS. 9a-9b and 10a-10b).

To analyze the captured time stamped still shots, a sub-VI has been created to process them. This sub-VI allows a user to browse a data disk for recorded images and set masking and threshold parameters. Additionally, it records the number and percentages of black pixels within the region of interest, and the resulting cumulative integration for the time variant stills to a file of the users choice (FIGS. 11a-11b and 12a-12c).

Global parameters are set using a settings sub-VI accessible from the main menu of the software. The settings sub-VI allows for modification of camera, masking, and threshold parameters contained in the global.inf file. The global.inf file allows for the easy loading of parameters into all of the other sub-VIs.

Figure 13:
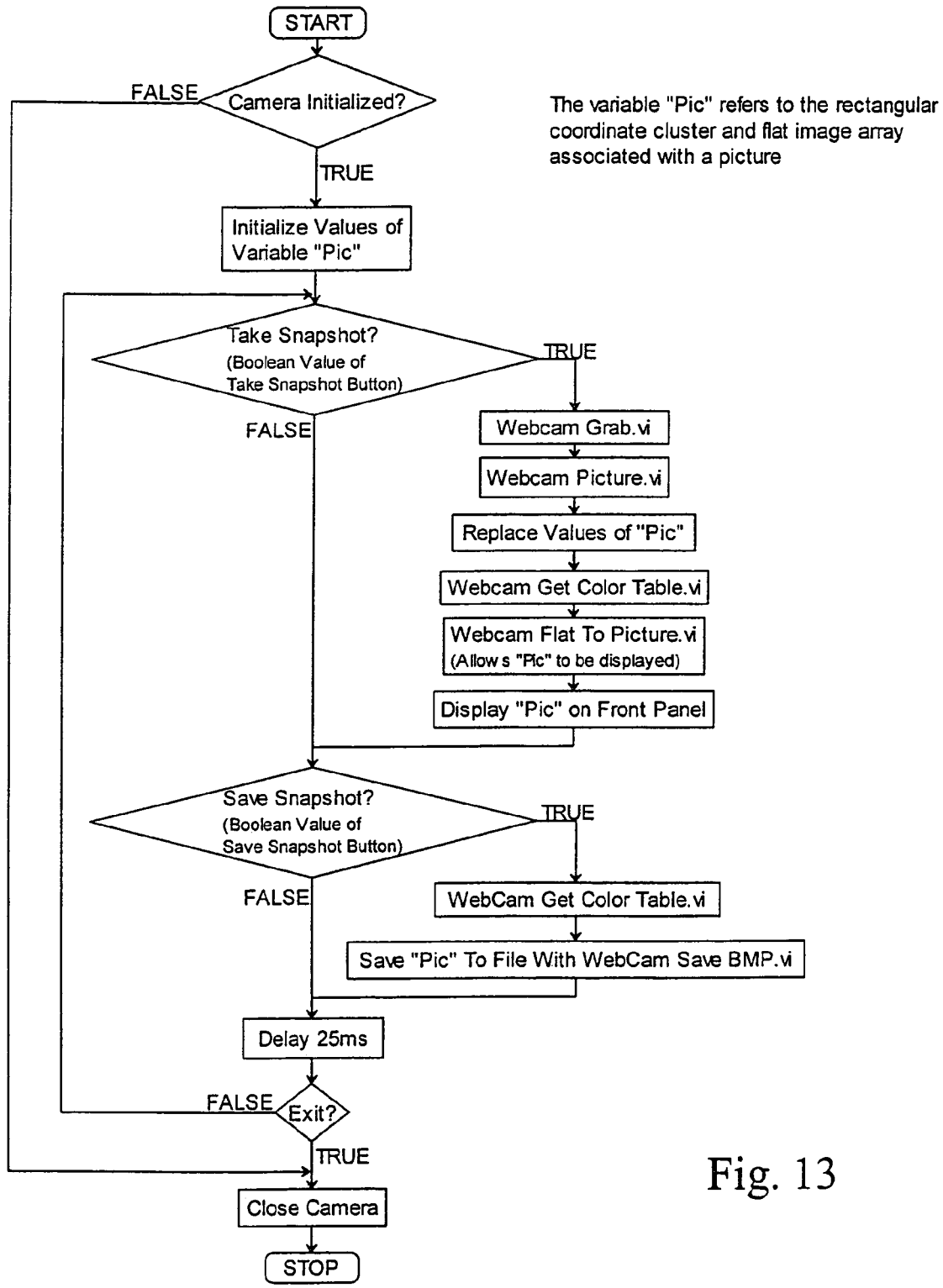
FIG. 13 is a drawing showing the Snapshot.VI Flow Diagram.
Figure 14:
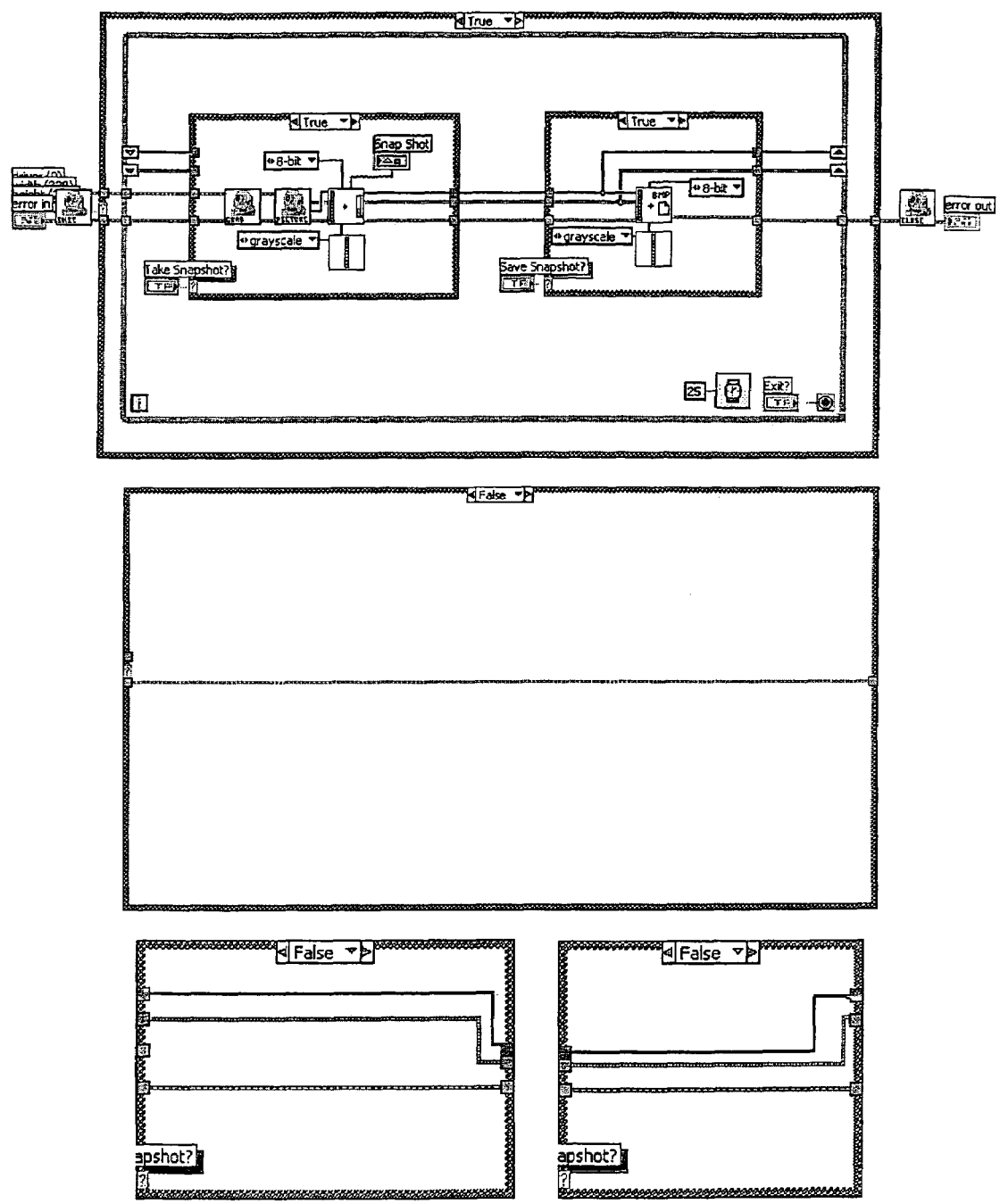
FIG. 14 is a drawing showing the Snapshot.VI LabVIEW Block Diagram.

For users who would like to take a single picture, a sub-VI has been created to save single snapshots from the camera (FIGS. 13 and 14).

Camera 7 can be any camera which can send digital images to a computer. One example of camera 7 is a webcamera. Camera 7 is connected to computer having a data analysis system with one computer USB input line interfacing with each sensor.

In operation, ventilation fan 2 pulls air to be sampled into housing 60 and into detection chamber 30. Air flow is controlled by fan 2 speed and the spacing between top 5 and body 8 created by washers 4a which should be from about 0.1 to about 0.3 cfm. As the air enters chamber 30 through an opening in the base of chamber 30, it passes at least one trained organism 35. If the sampled air contains the chemical or chemicals to which organism 35 is trained, organism 35 will exhibit area restricted searching behavior within the region of interest surrounding chamber 30 inlet.

Device 10 with at least one trained organism 35 is then placed in an area suspected of containing at least one target chemical. Air is drawn in from the air suspected of having the at least one target chemical into the system using ventilation fan 2 and into detection chamber 30 past the at least one organism. If response behavior is displayed, the software will alert the user with sound and visually with a blinking screen within about 25 seconds. The system is then purged with clean air by increasing fan speed. The at least one trained organism 35 will remain trained for about 48 hours before retraining or replacement.

The parasitic wasp, *Microplitis croceipes*, is used as a model organism, to show trained organisms in a system for chemical detection. *Microplitis croceipes* (Cresson) (*Hymenoptera:Braconidae*) is a solitary larval parasitoid of *Heliothis* and *Helicoverpa* species (*Hymenoptera:Noctuidae*). Adult females forage for food and hosts according to their physiological needs and females may use learned odors to locate both resources. Thus, females with experience on a plant-host complex or on host frass (faeces) are attracted to the odor of the plant-host complex and to host frass odor. Naive females antennating frass link it with an odor with a nonvolatile recognition kairomone found in frass that reinforces associative learning. In a similar fashion, naive females that are feeding on nectar or sugar water link the associated odor to the food resource. In this manner, wasps learn odors associated with the presence of hosts or food and subsequently use these odors as cues while foraging for more host or adult food. Wasps are readily conditioned to fly, coil, head-stick or antennate in response to odors associated with a host or food source. In the following examples, the number of wasps crowding around the chamber 30 inlet, where odor is emitted (region of interest), is recorded. This response is called the crowding behavioral response.

The following examples illustrate the use of a chemical detection system using *Microplitis croceipes* as a test model.

The examples are intended to further illustrate the invention and are not intended to limit the scope of the invention defined by the claims.

Example 1

The insects used in the following examples were laboratory reared at about 28° C. and about 50-70% relative humidity, with a 16:8 light cycle. Larvae of *Heliothis zea* were reared on pinto bean artificial diet according to the method described by Burton (U.S.D.A. Tech. Bull. ARS SER. 33/134, 1969; herein incorporated by reference). *Microplitis croceipes* were reared on *H. zea* as described by Lewis and Burton (Ann. Entomol. Soc. Amer., Volume 64, 471-473, 1970; herein incorporated by reference). Adult wasps were held in Plexiglas cages provided with water and honey. In all experiments females wasps were about 2-6 days old and host larvae were about $2^{nd}$ and $3^{rd}$ instar. Each experiment was completed over about 2 to 5 days with females from different cohorts each day. Each day, the same number of wasps was used for all treatments within an experiment.

Example 2

Female *M. croceipes*, about 2-4 days old were starved (provided water only) for about 26 to 30 hours at the time of the bioassays described below. The wasps were trained to detect 3-octanone, a ketone used in perfume and flavoring, as described in U.S. patent application Ser. No. 09/826,146, which is herein incorporated by reference.

Three corn sample preparations were used for testing.

The preparations were blank, control and test. The mouth of a mason jar was covered with a 12×12 cm piece of aluminum foil and shaken for about 15 seconds, subsequently creating small dimpling in the foil covering. Blank corn samples consisted of a 240 ml Mason jar with about 150 ml (120 grams) of whole kernel feed corn. Control samples were created from existing blank samples. The foil covering of the blank sample was removed and a Whatman filter disc was placed on top of the corn using a pair of forceps; the filter disc was pushed to the bottom of the corn using a separate pair of forceps before recovering the jar. After shaking, the sample was set aside to allow the head space over the corn to build for about 5 minutes. Test samples were created from control samples. A Whatman filter disc was loaded with an aliquot of 3-octane/dichloromethane solution on a glass dish and allowed to dry for about 1 minute. The foil covering of the control sample was removed, and the glass dish was used to drop the disc onto the top of the corn. A separate pair of forceps was used to push the odorous filter disc to the bottom of the corn before recovering the jar. After shaking, the sample was set aside to allow the head space over the corn to build for about 5 minutes.

Detection chamber 30 was observed while empty and while containing five *M. croceipes*. Chamber 30 containing 5 wasps placed over a control sample of corn was defined as a control treatment. Chamber 30 containing 5 wasps placed over a test corn sample was defined as a test treatment.

Chamber 30 was composed of three parts. Body 31 of chamber 30 was part of a Millipore Aerosol Analysis Monitor (FIG. 15). Top 32 was a lid for a Millipore PetriSlide™ modified to fit the body and thoroughly perforated with small holes to allow for sufficient ventilation (FIG. 16). A wire mesh disc 33 was placed in the bottom of the body to prevent the wasp from escaping out through the inlet (FIG. 17).

Before using, each chamber 30 was thoroughly cleaned with soap and water and dried. After drying, cleaning was continued by sweeping a 10L/min air stream for approximately 15 seconds over all surfaces of each chamber 30. Wasps were placed individually into chamber 30. Chamber 30 was placed upside down in a clean area under a fume hood.

The software described above was used for comparing the behavior of the wasps when presented with the air from the head space of the prepared corn samples. Data was taken for three different concentrations of 3-octanone masked with a background odor of whole kernel corn. The quantities of 3-octanone/dichloromethane solutions used to impregnate the filter disc were: about 10 μL of a 1:16 solution or about 0.5 mg 3-octanone which is about 5.5 ppm, about 2 μL of a 1:16 solution or about 0.1 mg of 3-octanone which is about 1.1 ppm, and about 10 μL of 1:842 solution or about 0.01 mg of 3-octanone which is about 111 ppt. For each concentration, 5 replications of blank, control, and test treatments were recorded. A blank was defined as a chamber 30 with no wasp over a blank corn sample. A control was defined as a chamber 30 containing 5 wasps over a control sample of corn, and a test was defined as a chamber 30 containing 5 wasps over a test corn sample.

Testing was performed in a fume hood and the laptop, camera 7, and samples were all placed under the fume hood. The laptop was placed in the front corner of the fume hood with the camera mount positioned approximately 15 cm to the left of the keyboard. During testing, all light sources within the room except the overhead fluorescence room lights were turned off or covered up resulting in an average light intensity of about 295 lux at the top of chamber 30. Logitech QuickCam 7 was placed so that the tip of the camera was approximately 2.54 cm (about 1 inch) above the top of the chamber 30 (1.4 cm=125 pixels).

Figure 18:
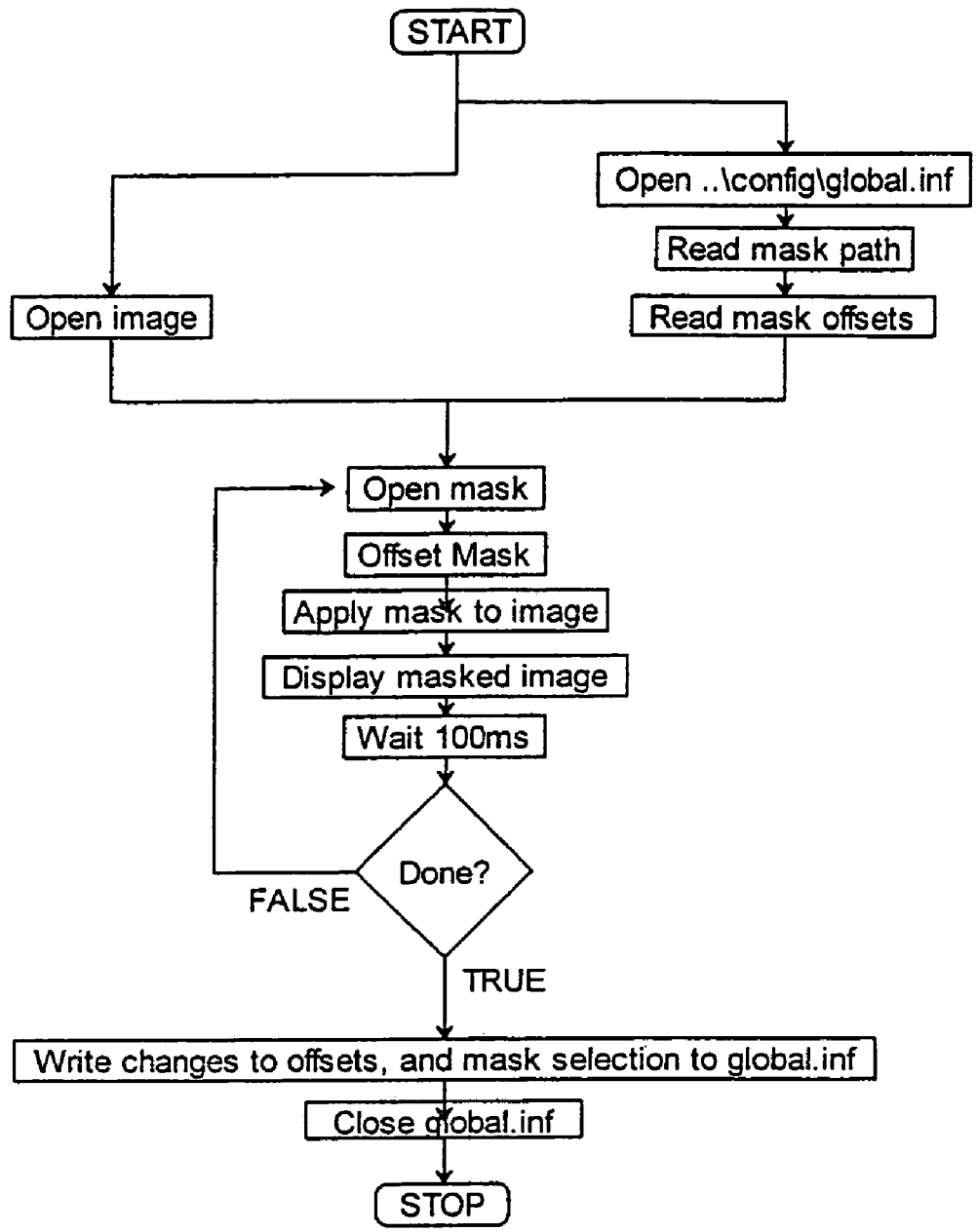
FIG. 18 is a drawing showing the Setmask.VI Flow Diagram.
Figure 19:
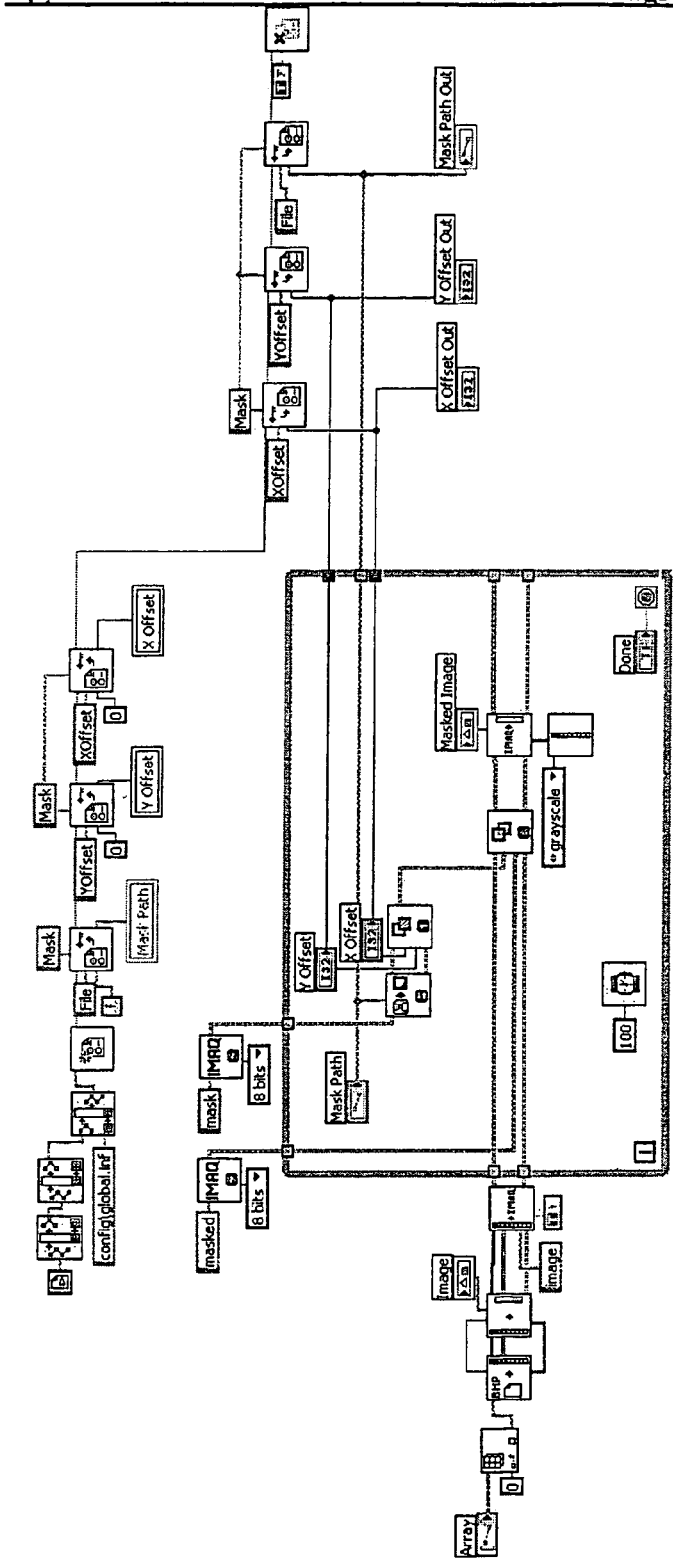
FIG. 19 is a drawing showing the Setmask.VI LabVIEW Block Diagram.

All pictures collected were analyzed with the software process stills function (FIGS. 11a-11b and 12a-12b). For each set of pictures, a black 320×240 pixel TIF image containing a centered 125 pixel diameter white circle was used as a mask. The image was given an X and a Y offset to center the mask's white circular area over the inlet of chamber 30 using setmask.vi (See FIGS. 18 and 19) accessible within process-stills.vi. The region of interest set by the mask corresponded to about a 1.4 cm diameter circular region. A lower threshold of 70 was used for binary segmentation (pixels value <70 forced to 0 and >70 forced to 1). The software provided data describing the amount of black pixels within the region of interest. The number of pixels, the percent total pixels, and the integration of the time variant percent of total pixels that were black within the region of interest for each set of pictures.

Initial analysis reveal large variations between the 15 blank treatments suggesting that some response curves may be inherently offset more than others due to significantly larger numbers of black pixels within the region of interest not representing wasp body mass, i.e., background noise. To remove the effects of these variances, the control and test treatment data was calibrated. From each set of images corresponding to single tests, one image was selected in which the wasps contained with chamber 30 were not searching within the region of interest. This image was used to measure the amount of black pixel noise not representing wasp body mass which is present within the region of interest throughout the 60 second test period. The image was masked, normalized, and segmented like all the other images processed during this study. The percent of the total black pixels within the region of interest was recorded for each image selected and analyzed and then used to create calibration curves for each treatment. Since the lighting within the test area and chamber 30 positioning would not have changed during the 60 second testing period, it was assumed that the same amount of black pixels within the region of interest not contributing to the measurement of the crowding behavior response would have remained constant throughout all images for that single treatment. The time values recorded for each test were copied to a spreadsheet and the percent black pixel values extracted from their corresponding calibration images were copied next to them, repeating the value for each time. The data was then integrated using the Trapezoidal rule function (above) with LabVIEW to create 20 new time-variant integration value curves to be used for calibration. The newly created calibration curves were then subtracted from their corresponding treatment response curves.

Microsoft's Excel was used to compile, average, and graph the approximately 256 (some variation existed due to computer latency) integration values and their corresponding stamps for the five replications per treatment within each concentration. The standard deviation was calculated for the integration values whose corresponding time stamps averaged out to approximately a multiple of five seconds (excluding zero). Confidence intervals were calculated using the resultant standard deviation values, an (=0.05 m and n=5.

An ANOVA statistical analysis of the data was performed using a general linear model (SAS). There were three dosage levels (0.5 mg, 0.1 mg, 0.01 mg), 3 treatments (blank, control, test) 5 replications of each dosage/treatment pair (15 total), and 12 observations from each replication (time stamps close to multiples of about 5 seconds) to create a total of 540 observations analyzed with the general linear model (GLM). The 15 blank treatment replications (180 observations) were analyzed to determine if each was statistically the same. The remaining 30 calibrated replications (15 controls, 15 tests) were analyzed by dosage and next by treatment to determine if either had significant effect on the mean response.

A total of 45 replications yielding 540 observations were collected and analyzed (Table 1).

TABLE 1

Treatment layout. Blank (no odor, no wasps), control (no odor, 5 wasps), and test (3-octanone, 5 wasps) treatments were each replicated five times for the 0.5 mg, 0.1 mg, and 0.01 mg dosage levels. Twelve observations occurring at multiples of about 5 seconds were extracted from each replication.

| Dosage | Blank | Control | Test | Σ |
|---|---|---|---|---|
| 0.5 | 5 Reps | 5 Reps | 5 Reps | 15 Reps |
|  | 12 obs/Rep | 12 Obs/Rep | 12 Obs/Rep |  |
|  | 60 Total Obs | 60 Total Obs | 60 Total Obs | 180 Obs |
| 0.1 | 5 Reps | 5 Reps | 5 Reps | 15 Reps |
|  | 12 Obs/Rep | 12 Obs/Rep | 12 Obs/Rep |  |
|  | 60 Total Obs | 60 Total Obs | 60 Total Obs | 180 Obs |
| 0.01 | 5 Reps | 5 Reps | 5 Reps | 15 Reps |
|  | 12 Obs/Rep | 12 Obs/Rep | 12 Obs/Rep |  |
|  | 60 Total Obs | 60 Total Obs | 60 Total Obs | 180 Obs |
| Σ | 15 Reps | 15 Reps | 15 Reps | 45 Reps |
|  | 180 Obs | 180 Obs | 180 Obs | 540 Reps |

There were significant differences between 15 blank replications (d.f.=1.4, n=180, P<0.0001). These results indicate the amount of black pixels measured within the region of interest of the empty chambers 30 varied significantly, suggesting that the physical properties of chamber 30 and/or lighting were variable.

Variability may have been caused by several factors including: dimpling in the aluminum foil covering and non-uniformity of chamber 30 tops, mesh bottoms, and lighting. Corn samples were shaken for about 15 seconds after being covered, and the corn striking the covering caused dimpling in the foil. This dimpling created diffuse reflection that may not have been uniform between corn samples. Chamber 30 tops, made from Millipore PetriSlide™ coverings, were modified by drilling holes in them and removing excess material from their edges. This was done by hand and non-uniformity in their construction is certain. Many of the edges of the drilled holes blocked the camera's 7 view of chamber 30 bottom; therefore variability in their placement would have caused non-uniform blocking of camera's 7 view. Additionally, the mesh discs placed in the bottom of chamber 30 body were metal and discolored some through repeated washings. Discoloration was caused by small amounts of oxidation. Discoloration may have been substantial enough to cause some of the pixels representing mesh in the images acquired to have a value lower than the segmentation threshold (LT=70 in present study). During testing all sources of lighting, excluding the overhead room lights, were covered. The overhead lights did not change location and it is assumed that their output was consistent over the test period. It is doubtful that the lighting conditions caused the large variability in the blank replications.

In mass production, a reproducible manufacturing method of chamber 30 would reduce the physical differences between chambers 30 since the metal mesh would not be needed to prevent the organisms from escaping chamber 30. A fixed lighting source reduces the possible variability in lighting and shadows.

Figure 20:
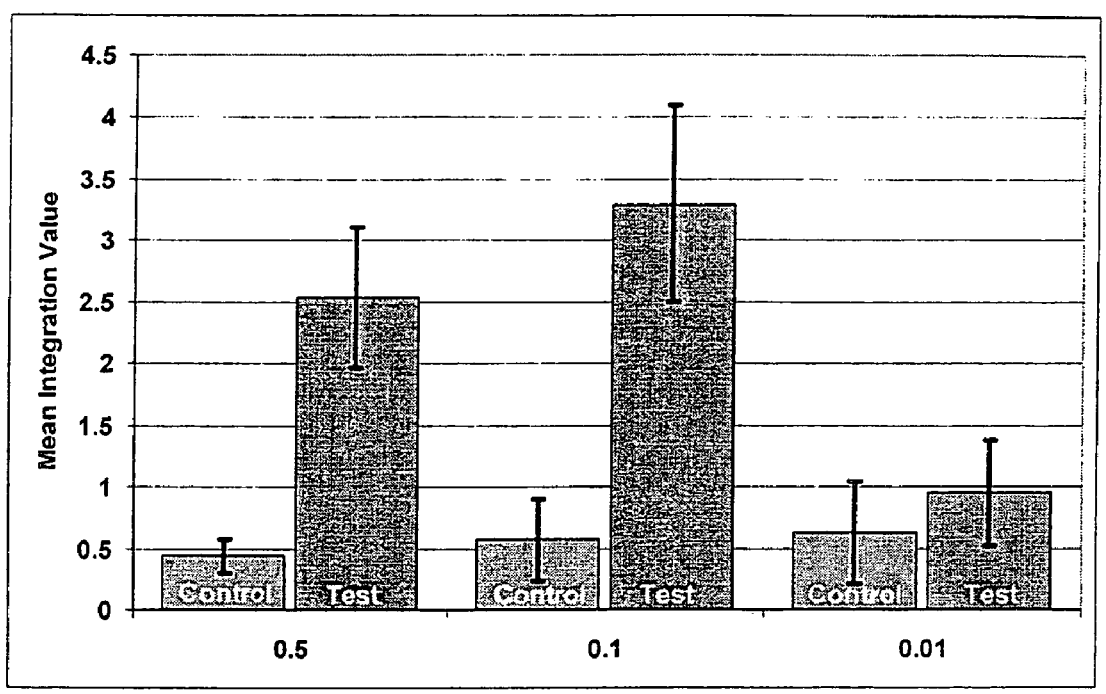
FIG. 20 is a graph showing the mean response for each treatment per dosage level and 95% confidence intervals. The means for the controls are not significantly different from each other or the test treatment at 0.01 mg (about 111ppt). The means of the test treatments at 0.5 and 0.1 mg, 5.5 and 1.1 ppm respectively, are not significantly different from each other but are different from the control treatments and the test treatment at 0.01 mg.
Figure 21:
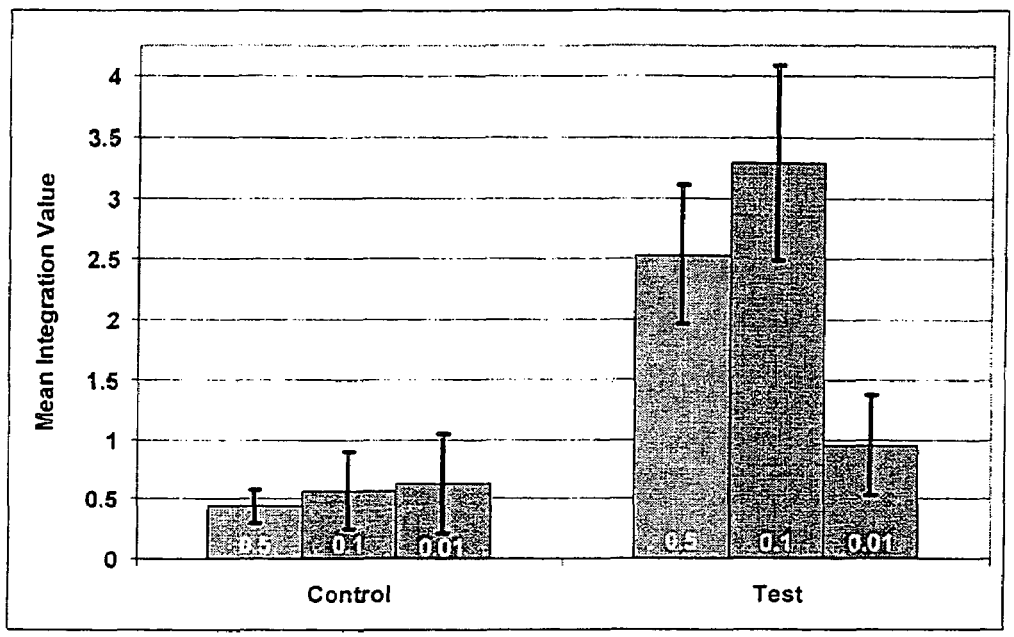
FIG. 21 is a graph showing the mean response for each dosage per treatment and 95% confidence intervals. The means of the controls are not significantly different from each other or the test treatment at 0.01 mg (11ppt). The means of the test treatments at 0.5 (5.5 ppm) and 0.1 mg (1.1 ppm) are not significantly different from each other but are different from the control treatments and the test treatment at 0.01 mg.
Figure 22:
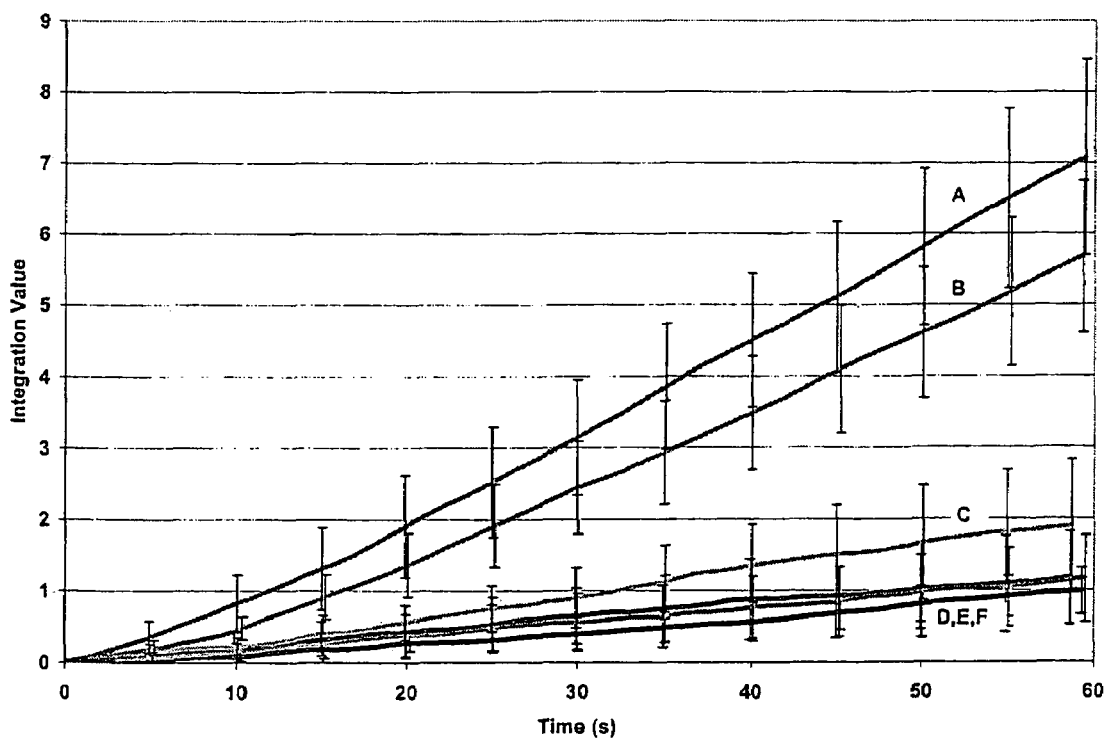
FIG. 22 is a graph showing means and 95% confidence intervals for all treatments at all dosage levels. Both the 0.1 mg (1.1 ppm) (A) and 0.5 mg (5.5 ppm) (B) test treatments were measured as significantly different from the 0.01 mg (111ppt) test (c) and all of the controls (D, E, F) after 20 seconds.

The control and test treatments (180 observations) were calibrated and analyzed to determine the effects of treatment and dosage on the mean response (average integration values over 60 second test period) (FIGS. 20, 21, and 22). FIG. 20 shows the control and test treatment mean responses grouped by dosage. The error bars were calculated using n=5 and α=0.05 for each treatment per dosage. FIG. 21 shows a different grouping of the same data in FIG. 20; dosage responses are grouped by treatment and error bars were calculated using n=5 and α=0.05 for each dosage per treatment. The response of the *M. croceipes* groups over the about 60 second test period can be seen in FIG. 22. The controls for all dosages were tightly grouped and were similar to the test treatment at the 0.01 mg dosage. The test treatments at the 0.5 mg and 0.1 mg dosages were both significantly different from all other treatment/dosage pairs after, at most, about 20 seconds. Errors were calculated using n=5 and α=0.05 for each treatment per dosage.

Figure 23:
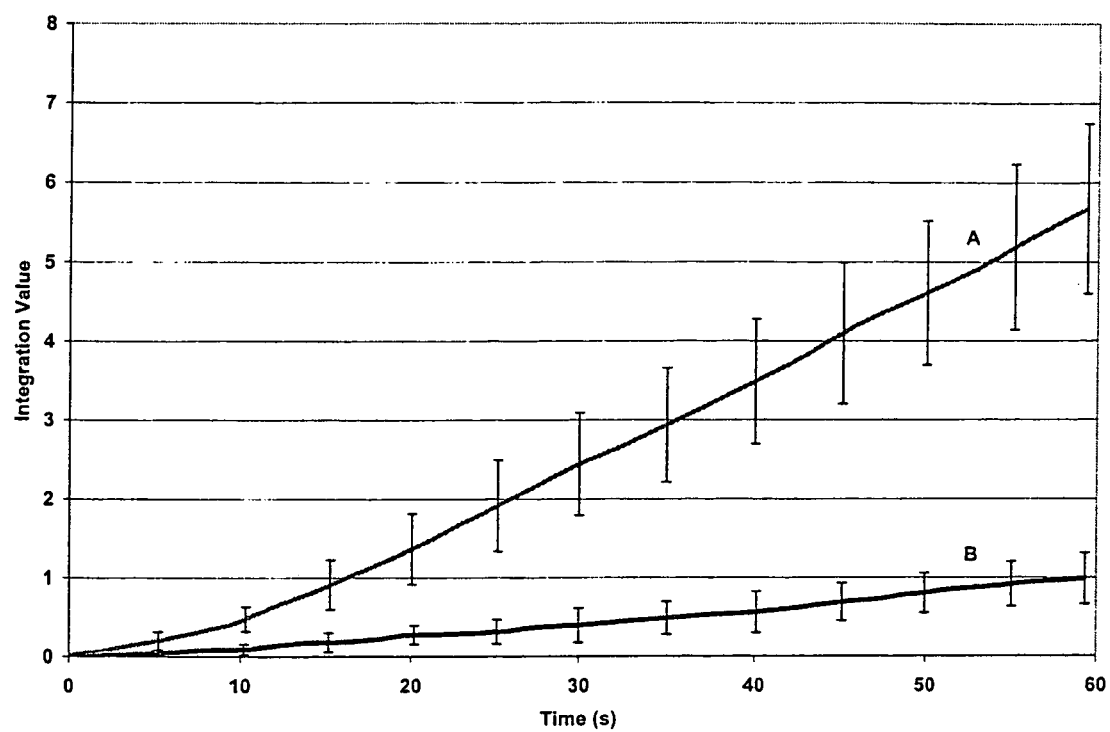
FIG. 23 is a graph showing the means and 95% confidence intervals for calibrated control (B) and test (A) treatments at the 0.5 mg of 3-octanone dosage level. There was significant difference between treatments after about 10 seconds.

Five groups of *M. croceipes* (5 individuals per group) received both control and test treatments using 0.5 mg of 3-octanone. The behavioral response of *M. croceipes* at the 0.5 mg dosage level was significant across treatments (d.f.=1, n=120, P<0.0001). The mean response of the test treatment (2.7638) was significantly higher than that of the control treatment (0.4763). The time (d.f.=11, n=120, P<0.0001) and treatment time interaction (d.f.=11, n=120, P<0.0001) effects were also both significant, indicating that the integration values were dependent on both treatment and elapsed time. The system was able to detect a significant difference in the test and control treatment responses in about 10 seconds (FIG. 23).

Figure 24:
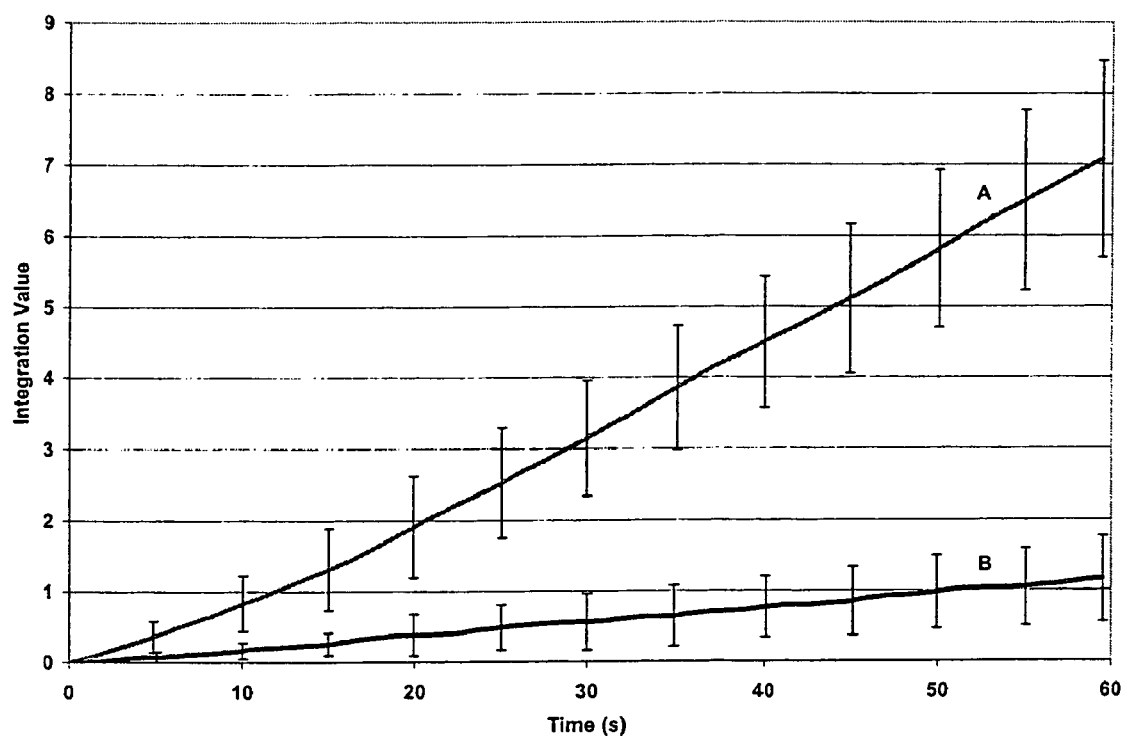
FIG. 24 is a graph showing means and 95% confidence intervals for calibrated control (B) and test (A) treatments at the 0.1 mg of 3-octanone dosage level. There was a significant difference between responses to treatments after about 10 seconds.

Similar results were obtained with five groups of *M. croceipes* (5 individuals per group) receiving both control and test treatments using 0.1 mg of 3-octanone. The behavioral response of *M. croceipes* at the 0.1 mg (1.1 ppm) dosage level was significant across treatments (d.f.=1, n=120, P=0.0002). The mean response of the test treatment (3.5822) was significantly higher than that of the control treatment (0.6117). The time (d.f=11, n=120, P<0.0001) and treatment*time (d.f=11, n=120, P<0.0001) effects were also both significant, indicating that the 120 integration values (12 Obs./Rep. for 5 test and 5 control reps.) were time and treatment dependent. The system was able to detect a significant difference in the test and control treatment responses in ≈10 seconds (FIG. 24).

The system was able to quantify the behavior of the trained wasps in such a way as to successfully distinguish between the crowding behavior exhibited when presented with the target odor at the about 0.5 mg and about 0.1 mg levels and the individual searching behaviors exhibited when presented with only the odor of corn. When looking at individual dosages, a significant difference in the two treatments was detectable in as little as about 10 seconds (FIGS. 23 and 24). When results from the dosages were pooled, a significant difference between the tests and controls was detectable in about 20 seconds (FIG. 22).

Figure 25:
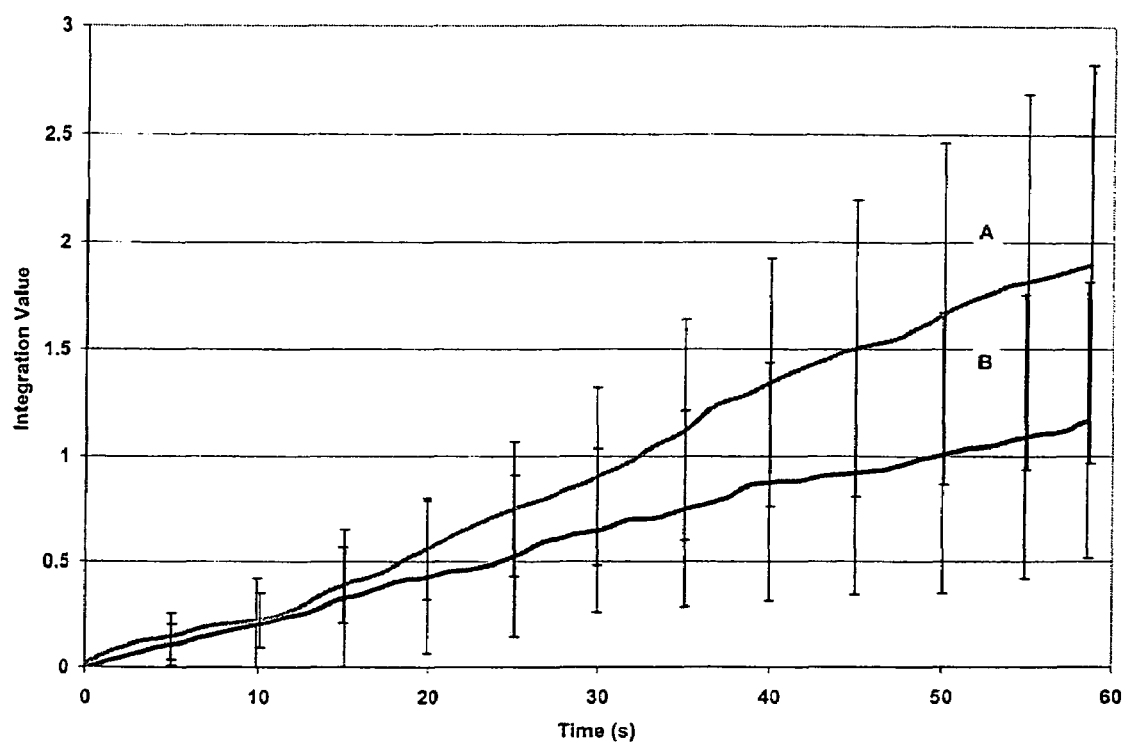
FIG. 25 is a graph showing means and confidence intervals for calibrated control (B) and test (A) treatments at the 0.01 mg of 3-octanone dosage level. There was no significant difference between responses to treatments.

The behavioral response of *M. croceipes* at the 0.01 mg dosage level was not significantly different across treatments (d.f.=1, n=120, P=0.3100). However, the time (d.f.=11, n=120, P<0.0001) and treatment time interaction (d.f.=11, −120, P=0.0498) effects were both significant at $\alpha$=0.05, indicating that the 120 integration values (12 Obs/Rep. For 5 test and 5 control reps) were time dependent (FIG. 25). At this dosage, it appears that the odor concentration was too low to elicit a crowding behavior strong enough for the system to detect as significantly different from the control, or the wasps were unable to detect the odor.

Figure 26:
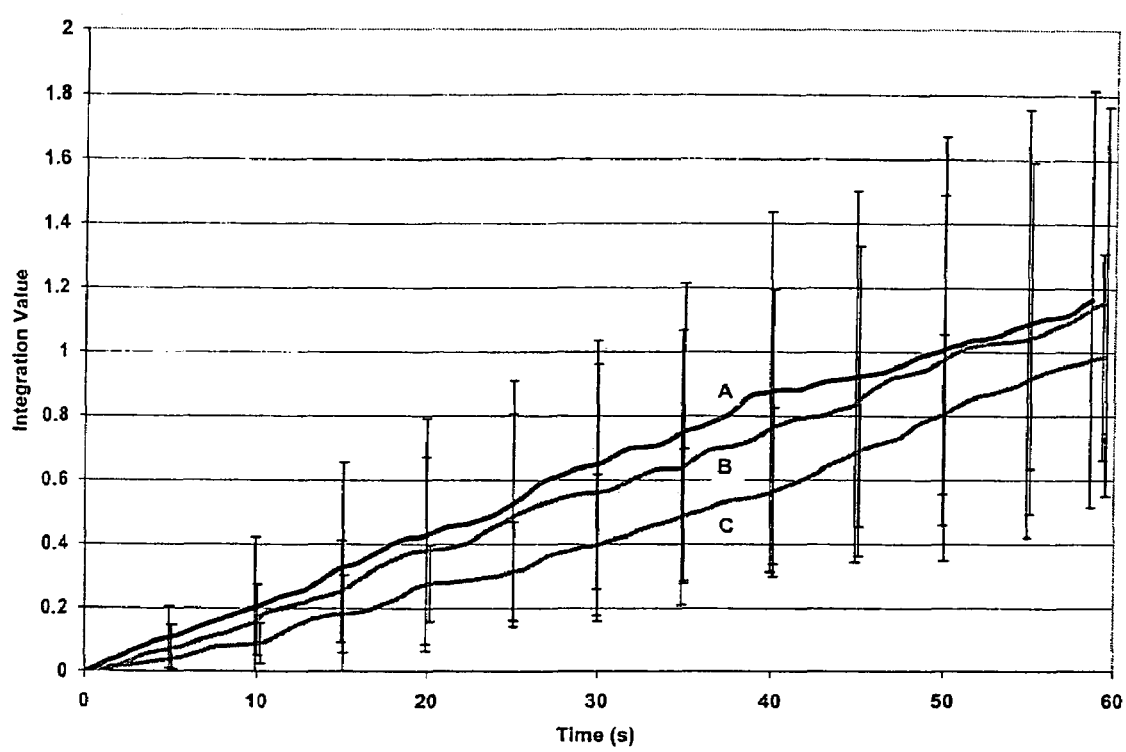
FIG. 26 is a graph showing means and 95% confidence intervals for calibrated control treatments corresponding to test treatments at (B) 0.1 mg, (A) 0.01 mg, and © 0.5 mg dosage levels. Dosage grouping had no significant effect on response to control treatment.

Fifteen groups of *M. croceipes* (5 individuals per group) received control treatments before receiving test treatments at one of three dosages: 0.5 mg, 0.1 mg, and 0.01 mg. Dosage had no significant effect on *M. croceipes* response to the control treatment (d.f.=2, n=180, P=0.7159). Dosage time interaction effects were not significant (d.f.=22, n=180, P=1.0), but time effects were (d.f.=11, n=180, P<0.0001), indicating that the interaction values were affected by time but not by what test treatment dosage they preceded (FIG. 26). These results imply that the groups of wasps exhibited similar searching behaviors. No group spent significantly more or less time within the region of interest that any other group, allowing for the assumption that test treatment results were not biased by the normal searching behavior of trained *M. croceipes*.

Figure 27:
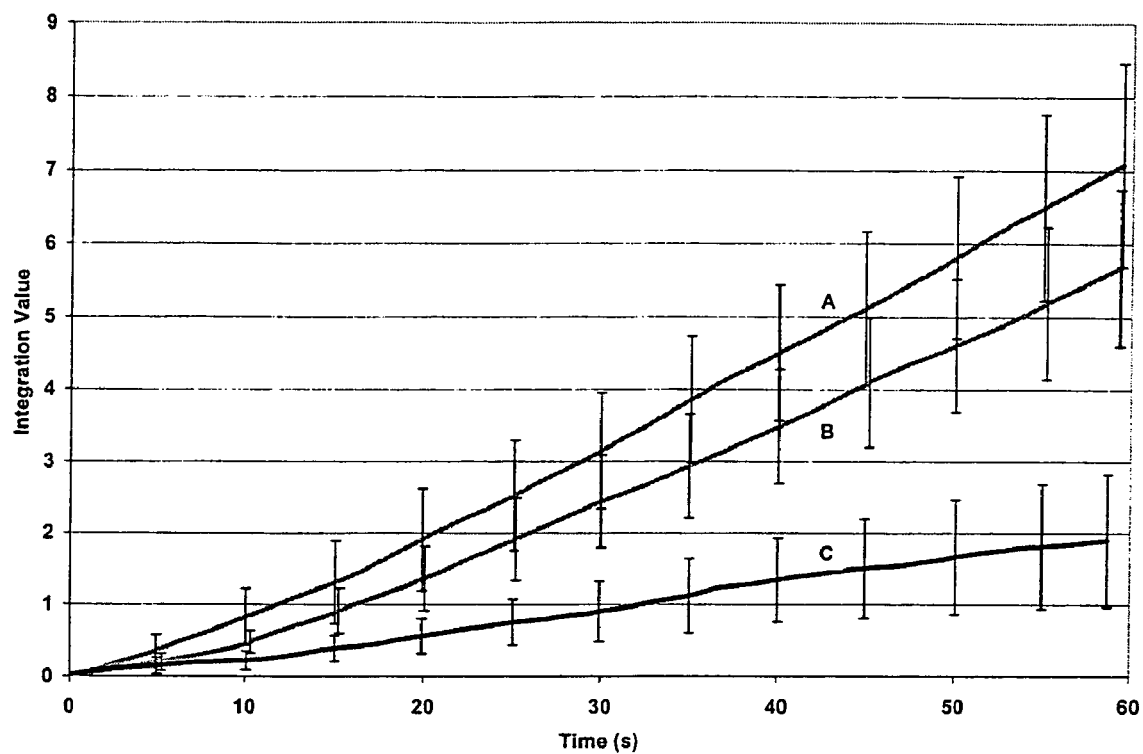
FIG. 27 is a graph showing means and 95% confidence intervals for calibrated test treatments at (A) 0.1 mg, (B) 0.5 mg, and (c) 0.01 mg dosage levels. The response mean of the test treatment at the 0.01 mg dosage level was significantly lower than at the 0.1 mg and 0.5 mg.

Dosage did have significant effect on *M. croceipes* response to the test treatment (d.f.=2, n=180,P=0.0005). The 0.1 mg (3.5822) and 0.5 mg (2.7639) response means were not significantly different from each other, but they were both significantly different from the 0.01 mg response mean (1.0254). Both time (d.f.=11, n=120, P<0.0001) and the dosage time interaction (d.f.=22, n=120, P<0.001) significantly affected the integration values (FIG. 27).

The system was not able to distinguish between responses to dosages that were significantly different from the controls.

Example 3

Female *M. croceipes*, about 2-4 days old were starved (provided water only) for about 26 to 30 hours at the time of the bioassays described below. The wasps were trained to detect myrcene, a plant terpenoid, and 3-octanone, a ketone used in perfume and flavoring, as described in U.S. patent application Ser. No. 09/826,146, which is herein incorporated by reference.

Three corn sample preparations were prepared as described above in Example 2. A total of 10 blanks, 15 controls, 10 tests containing Myrcene, and 10 tests containing 3-octanone. Chamber 30 and insects were prepared for the study as described above in Example 2.

A Fintip™ plastic pipette tip was inserted into the bottom of chamber 30 so that the large end of the pipette tip fit frictionally into the inlet of chamber 30 (FIG. 15). The tip channeled all airflow directly to the inlet of chamber 30. Data was collected using the software described above with both untrained and trained wasps presented with 3-octanone and myrcene odorants. Empty containers over blank corn samples were also tested to check for the uniformity of chambers 30 and lighting. The crowding behavior of *M. croceipes* was observed under 3 conditions:

1) Untrained wasps presented with control sample, then 3-octanone test sample.

2) Untrained wasps presented with control sample, then Myrcene test sample.

3) Wasps trained to 3-octanone presented with control sample, then Myrcene test sample then 3-octanone-test sample.

Images of the behavioral responses of untrained wasps when presented with either odorant were collected to determine if *M. croceipes* has natural attraction to either 3-octanone or myrcene. During this time, the 10 blank replications were preformed.

All pictures collected were analyzed with the software's Process Stills function (FIGS. 11A-11B and 12A-12C). For each set of pictures, a black 320×240 pixel TIF image containing a centered 125 pixel diameter white circle was used as a mask as described above in Example 2.

Initial analysis revealed a large variation between the blank (empty chamber 30 over corn containing no additional odorant) suggesting that some response curves may be inherently offset more than others due to significantly larger numbers of black pixels within the region of interest not representing wasp body mass (background noise). To remove the effects of these variances the control and test treatment data was calibrated. Form each set of images corresponding to single tests, one image was selected in which the wasps contained within chamber 30 were not searching within the region of interest. This image was used to measure the amount of black pixel noise (not representing wasp body mass) present with the region of interest throughout the 60 second test period. The image was masked, normalized, and segmented like all other images processed during this study. The percent of the total black pixels within the ROI was recorded for each image selected and analyzed and then used to create calibration curves for each treatment. Since the lighting and chamber 30 positioning does not change during the 60 second testing period, it was assumed that the same amount of black pixels within the region of interest not contributing to the measurement of the crowding response would have remained constant throughout all images for that single treatment. The time values recorded for each test were copied to a spreadsheet and the percent black pixel values extracted from their corresponding calibration images were copied next to them, repeating the value for each time. The data was then integrated using the Trapezoidal Rule function within LabVIEW to create 35 new time-variant integration value curves to be used for the calibration. The newly created calibration curves were then subtracted from their corresponding treatment response curves.

Microsoft Excel was used to compile, average, and graph the approximately 256 (some variation existed due to computer latency) integration values and their corresponding time stamps for all calibrated replications (untrained wasps: ten controls, five Myrcene tests, five 3-octanone tests). The standard deviation was calculated for the integration values whose corresponding time stamps averaged out to approximately a multiple of five seconds (excluding zero). Confidence intervals were calculated using the resultant standard deviation values, an $\alpha=0.05$, and n=5.

An ANOVA statistical analysis of the data was performed using a general linear model (SAS). Observations were taken from the 15 groups (5 individuals per group) of *M. croceipes* divided unevenly into 2 levels of training (10 groups untrained, 5 groups trained). The untrained groups were further divided into 2 sets (5 groups per set). One untrained set received control and myrcene treatments. The other untrained set received control and 3-octanone treatments. Prior to each control treatment, measurements were taken from an empty chamber 30 over a blank corn sample (i.e. blank treatment). The 5 groups of trained *M. croceipes* received control and myrcene and 3-octanone test treatments. Each treatment was replicated 5 times. The 10 blank treatment replications (120 observations) were analyzed to determine if each was statistically the same. The remaining 35 calibrated replications (15 controls, 10 myrcene tests, 10 3-octanone tests) were analyzed by training and by treatment to determine if either factor had significant effect on the mean response. A total of 45 replications containing 540 observations were collected (Table 2). Table 2. Treatment Layout. Blank (no odor, no wasps) and control (no odor, 5 wasps).

TABLE 2

Treatment Layout. Blank (no odor, no wasps) and control (no odor, 5 wasps).

| Training | Blank | Control | Myrcene | 3-octanone | Σ |
|---|---|---|---|---|---|
| untrained | 10 Reps<br>12 Obs/Rep<br>120 Total Obs | 10 Reps<br>12 Obs/Rep<br>120 Total Obs | 5 Reps<br>12 Obs/Rep<br>60 Total Obs | 5 Reps<br>120 Obs/Rep<br>60 Total Obs | 30 Reps<br>360 Obs |
| Trained | 0 Reps<br>0 Reps/Obs<br>0 Total Obs | 5 Reps<br>12 Obs/Rep<br>60 Total Obs | 5 Reps<br>12 Obs/Rep<br>60 Total Obs | 5 Reps<br>12 Obs/Rep<br>60 Total Obs | 15 Reps<br>180 Obs |
| Σ | 10 Reps<br>120 Obs | 15 Reps<br>180 Obs | 10 Reps<br>120 Obs | 10 Reps<br>120 Obs | 45 Reps<br>540 Obs |

When blank chamber 30 measurements were compared, there were significant differences between the 10 individual blank treatment replications (d.f.=9, n=120, P<0.0001). These results indicate the amount of black pixels measured within the region of interest of the empty chambers 30 varied significantly, suggesting that the physical properties of the chambers 30 and lighting were variable as discussed above in Example 2.

Figure 28:
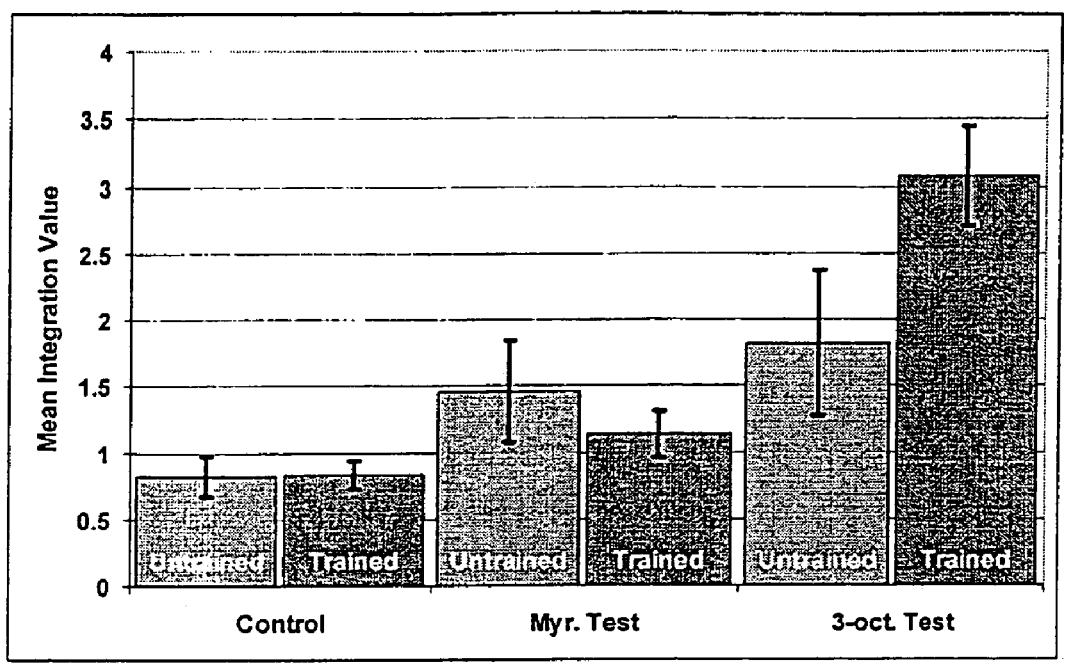
FIG. 28 is a graph showing the mean response for training per treatment. The mean of the controls are not significantly different from each other or the myrcene test treatment of trained *M. croceipes*. The means of the myrcene test treatments for trained and untrained wasps are not significantly different. The means of the myrcene and 3-octanone test treatments for untrained wasps are not significantly different. The mean integration value of the 3-octanone test treatment for wasps trained to detect 3-octanone is significantly different from all other treatment/training pairs.
Figure 29:
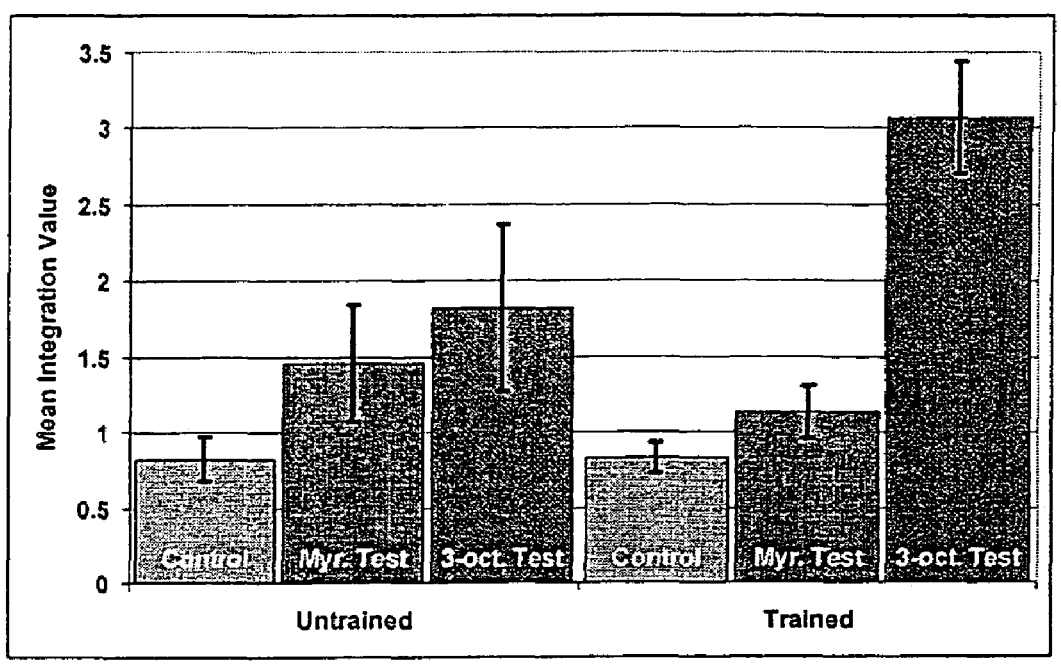
FIG. 29 is a graph showing the mean responses for treatments per training arranged by treatments per training. The means of the controls are not significantly different from each other or the myrcene test treatment of trained wasps. The means of the myrcene test treatments for trained and untrained wasps are not significantly different. The means of the myrcene and 3-octanone test treatments for untrained wasps are not significantly different. The mean integration value of the 3-Octanone test treatment for wasps trained to detect 3-octanone is significantly different from all other treatment/training pairs.
Figure 30:
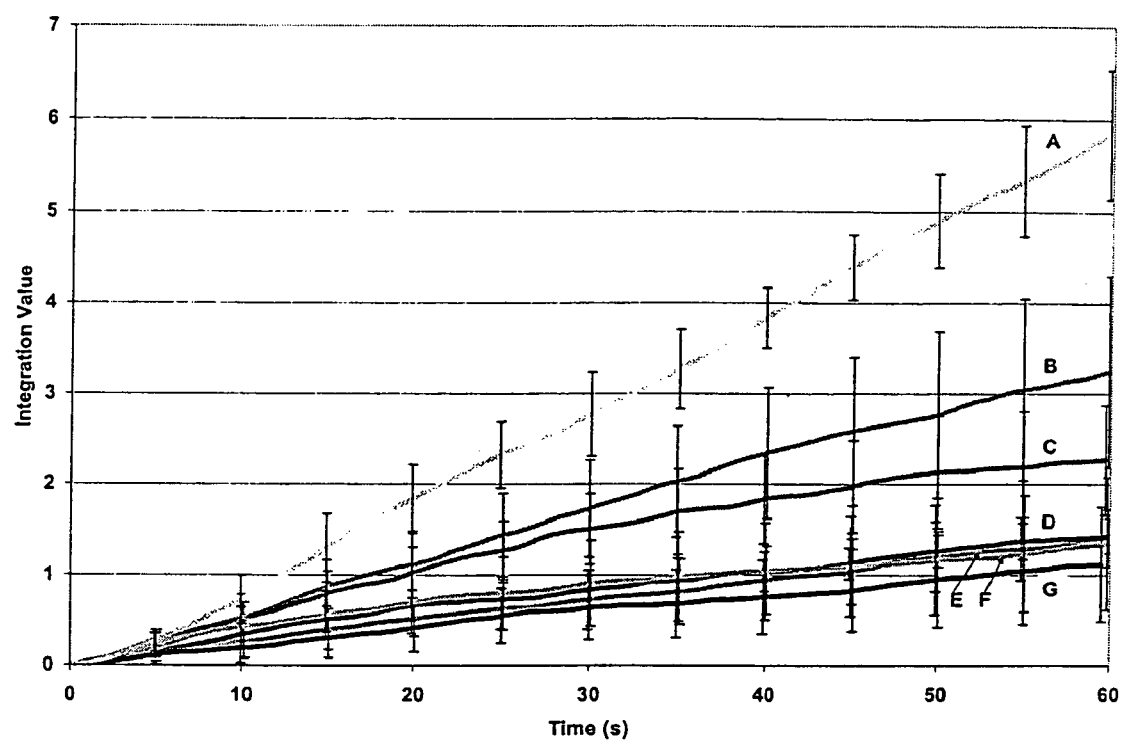
FIG. 30 is a graph showing means and 95% confidence intervals for treatments of trained (A, F, G) and untrained (B, C, D, E) wasps. The mean response of wasps trained to detect 3-octanone receiving 3-octanone test (A) treatments was measured as significantly different from untrained wasps receiving 3-octanone (B) and myrcene (C) test and control (D,E) treatments, trained wasps receiving myrcene test (F) and control (G) treatments after 25 seconds.

When the effects of treatment and training on response was tested, the control and test treatments (420 observations) were calibrated, as discussed above, and then analyzed to determine the effects of treatment and training on the mean response (average integration values over 60 second test period). FIG. 28 shows the mean responses exhibited by untrained and trained wasps grouped by treatment. The error bars were calculated using n=5 and $\alpha=0.05$ for each state of training per treatment. FIG. 29 shows a different grouping of the same data in FIG. 28; treatments are grouped by training, and error bars were calculated using n=5 and $\alpha=0.05$. The response of the wasp groups over the 60 second test period can be seen in FIG. 30. The response of the wasps trained to detect 3-octanone in the presence of the target odor was significantly different from all other treatment/training pairs after 25 seconds.

Figure 31:
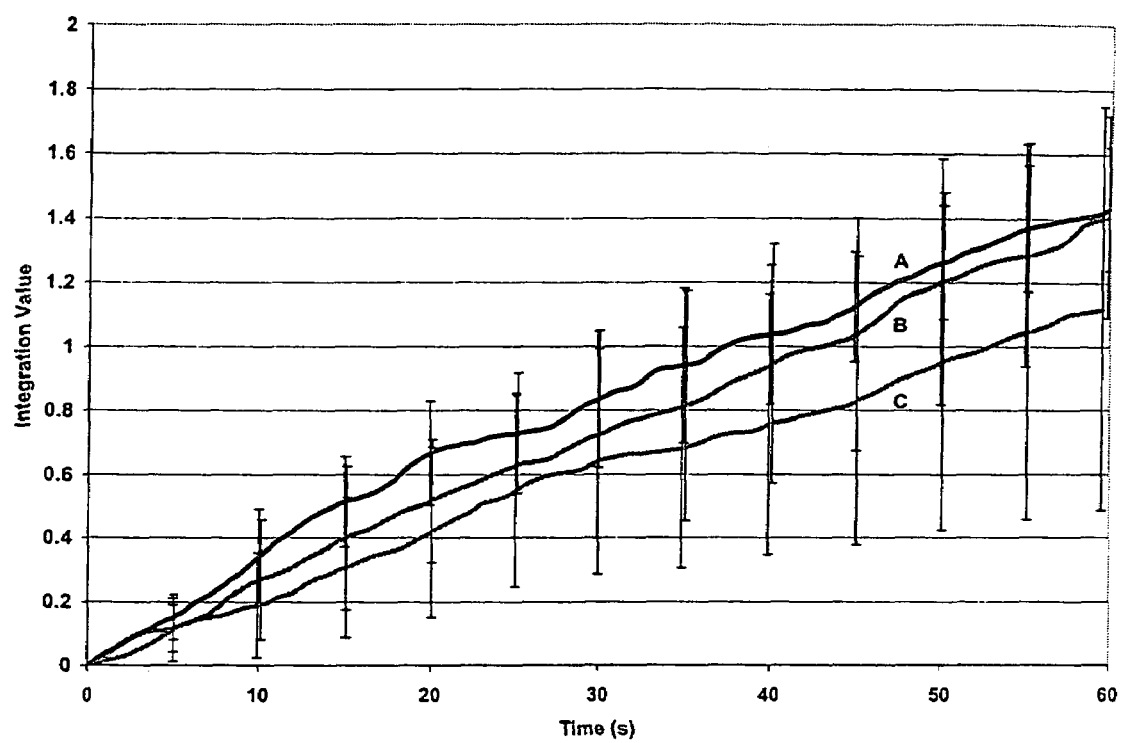
FIG. 31 is a graph showing means and 95% confidence intervals for calibrated no odor treatment responses for wasps trained (C) and untrained (A, B) to 3-octanone. Training had no significant effect on response.

Fifteen groups of wasps received control treatments and were compared. Five groups received prior training to 3-octanone, and ten did not. The behavioral response of wasps receiving the control treatment was not significantly different within or across training (d.f.=2, n=180, P<0.8025). The mean responses of the untrained wasps (0.8670 and 0.7778) were not significantly different from each other or the mean response of wasps trained to detect 3-octanone and receiving the same treatment (0.8316) (FIG. 31). This suggests that any cohort or day difference that existed did not influence or bias the amount of time the wasps spent within the region of interest.

Figure 32:
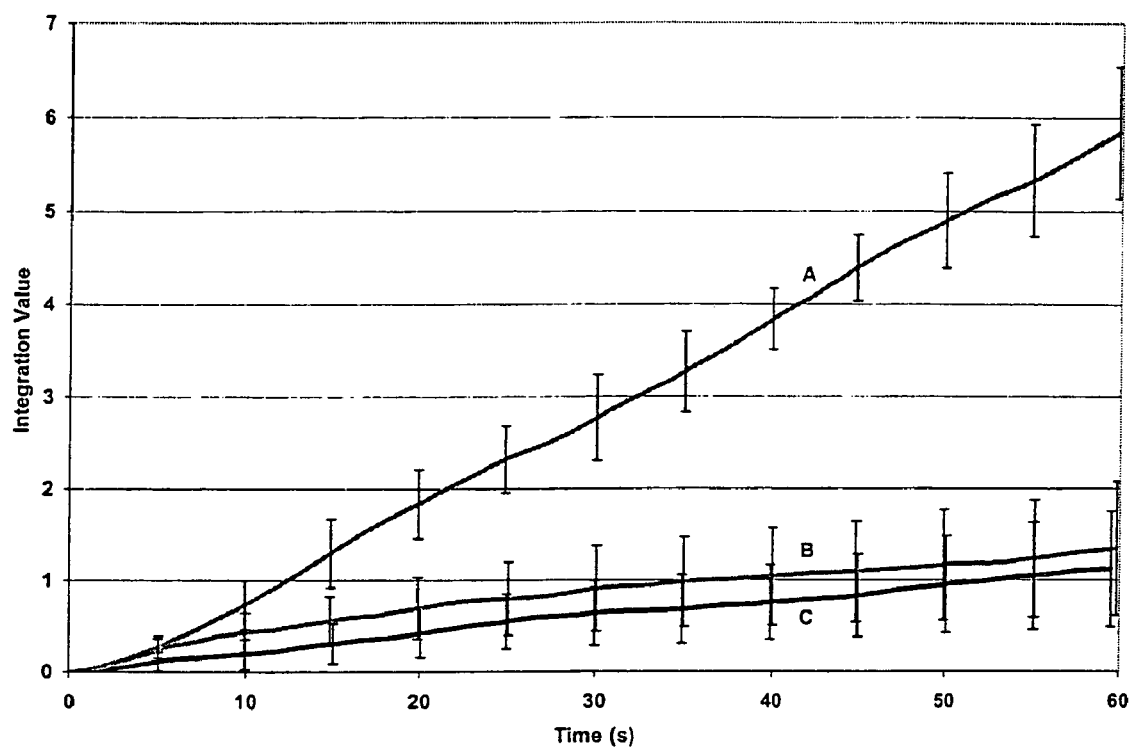
FIG. 32 is a graph showing means and 95% confidence intervals for calibrated 3-octanone (A), myrcene (B), control© treatment responses of wasps trained to detect 3-octanone. The mean response to 3-octanone was significantly larger than those of myrcene and control treatments. There was no significant difference between the myrcene and control treatment responses.

Five groups of wasps trained to detect 3-octanone received control, myrcene, and 3-octanone treatments, in order, to test the effects of treatment on response of the wasps. The behavioral response of the wasps trained to detect 3-octanone was significantly different across treatments (d.f.=2, n=180, P<0.0001)(FIG. 32). The mean response of the trained wasps exposed to 3-octanone (3.0698) was significantly larger than that of trained wasps exposed to myrcene (1.1337) or corn alone (0.8316). However, no significant difference existed between the mean response to myrcene and control treatments. Both time (d.f.=11, n=180, P<0.0001) and the treatment time interaction (d.f.=22, n=180, P<0.0001) had significant effects. Trained wasps showed interest in the myrcene, but the amount of crowding elicited by the 3-octanone was significantly greater than both the myrcene and control treatments within 15 seconds.

Figure 33:
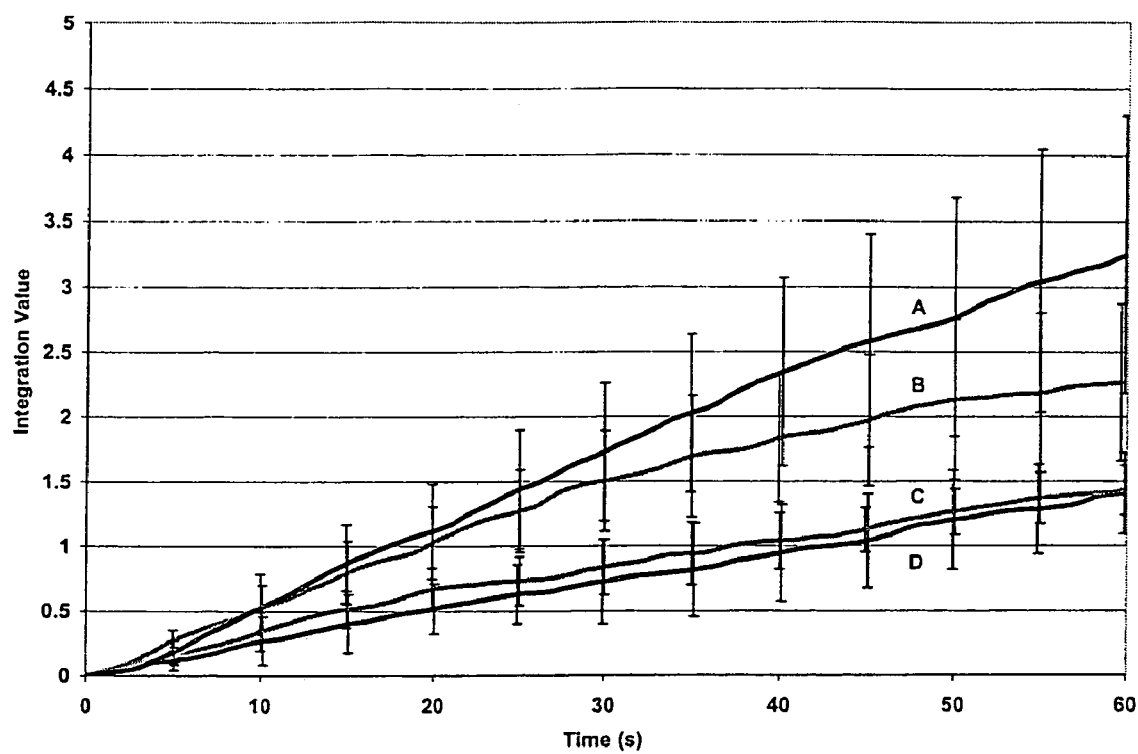
FIG. 33 is a graph showing means and 95% confidence intervals for calibrated 3-octanone (A), myrcene (B) and control (C), D) treatment responses of untrained wasps. There was no significant difference between 3-octanone and myrcene treatment responses. There was no significant difference between control treatments. Both mean responses of the untrained wasps exposed to myrcene and 3-octanone were significantly different from the mean response of the control treatment.

Ten groups of untrained wasps received control and test treatments to see the effects of treatment on the untrained wasps. Five groups were presented with 3-octanone during their test treatment, and five groups were presented with myrcene. The behavioral response of untrained wasps was significantly different across treatments (d.f.=3, n=240, P=0.0033) (FIG. 33). The mean responses of untrained wasps exposed to 3-octanone (1.8190) or myrcene (1.4537) were not significantly different, but they were both significantly different from the mean responses of both control treatments (0.8670 and 0.7778). The control treatment responses were not significantly different. Both time (d.f.=11, n=180, P<0.0001) and the treatment time interaction (d.f.=33, n=180, P<0.0001) had significant effects. Again, the groups were not biased in the amount of time spent searching within the region of interest, but did show a curiosity in the strong odorants though no prior training or exposure had been experienced.

Figure 34:
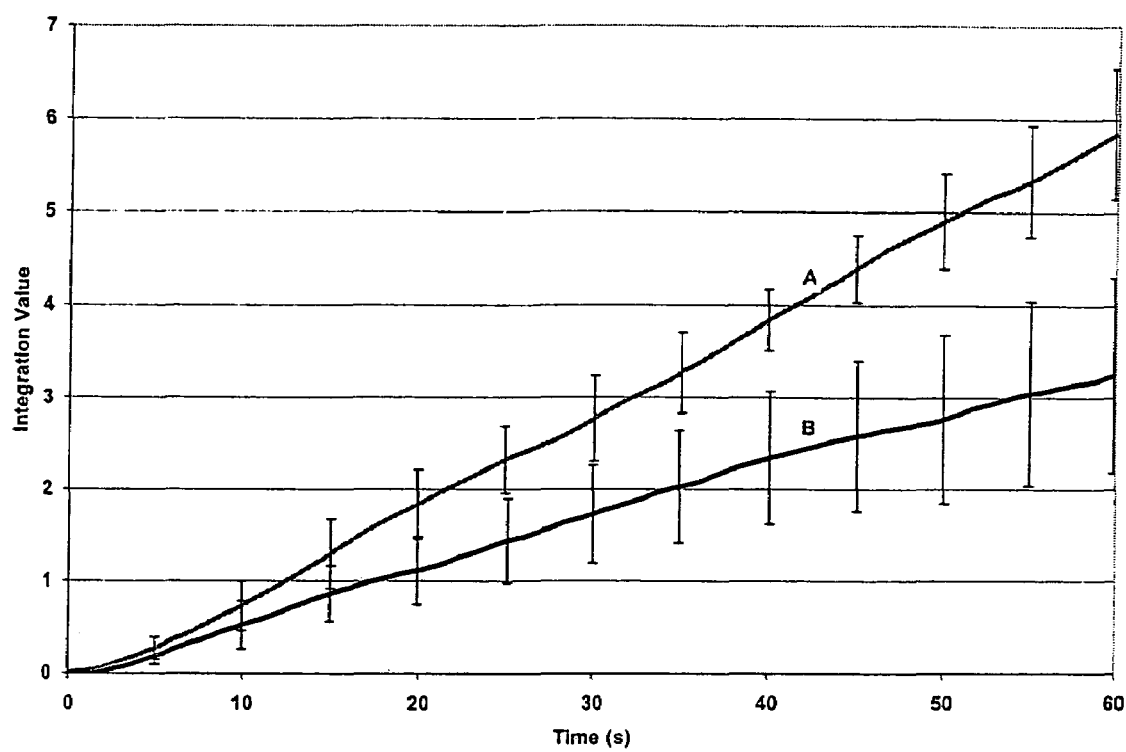
FIG. 34 is a graph showing means and 95% confidence intervals for calibrated 3-octanone treatment responses for trained (A) and untrained (B) wasps. Trained wasps exhibited more crowding when exposed to 3-octanone than did untrained wasps.

Ten groups of wasps were exposed to 3-octanone to see the effects of training to 3-octanone. Five groups had received prior training to 3-octanone and 5 groups were untrained. The behavioral response of the wasps exposed to 3-octanone was significantly different across training (trained vs. untrained) (d.f.=1, n=120, P=0.0059) (FIG. 34). Wasps trained to detect 3-octanone had a significantly higher mean response (3.0698) when presented with 3-octanone than did untrained wasps (1.8190) receiving similar treatment. Both the time (d.f.=11, n=120, P<0.0001) and treatment time interaction (d.f.=11, n=120, P<0.0001) effects were significant. Untrained wasps exhibited a natural curiosity towards 3-octanone, but trained wasps exhibited significantly more crowding.

Figure 35:
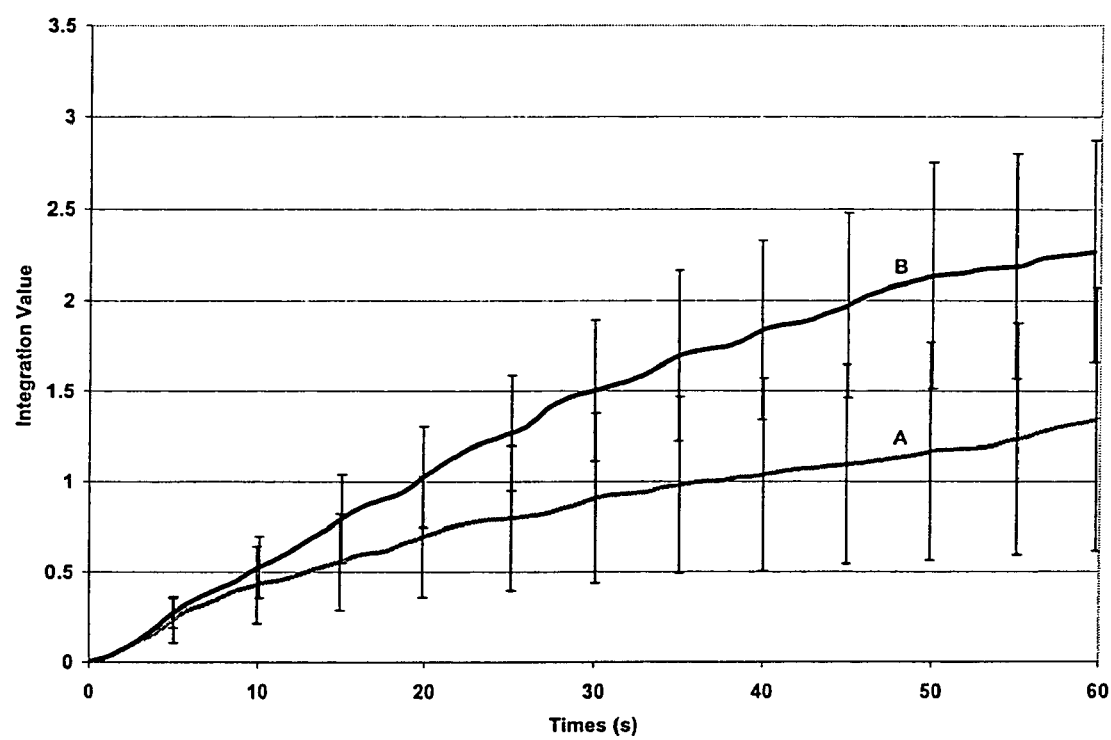
FIG. 35 is a graph showing means and 95% confidence intervals for calibrated myrcene treatment responses for wasps trained (A) and untrained (B) to 3-octanone. Training had no significant effect on response.

Ten groups of wasps were exposed to myrcene to see the effects of training to 3-octanone on the response of the wasps. Five groups had received prior training to 3-octanone and five groups were untrained. The behavioral response of wasps exposed to myrcene was not significantly different across training (d.f.-1, n=120, P=0.1732) (FIG. 35). Wasps trained to detect 3-octanone had a similar mean response (1.1337) when presented to myrcene to untrained wasps (1.4537) receiving similar treatment. Both the time (d.f.=11, n=120, P<0.0001) and treatment time interaction (d.f.=11, n=120, P<0.0010) effects were significant. The response to myrcene was not significant across training.

The above detailed description is for the purposes of illustration. Others skilled in the art can apply the knowledge described to train other invertebrates to detect chemicals for use in a system for chemical detection. Such detail is solely of that purpose and those skilled in the art can make variations therein without departing from the spirit and scope of the invention.

INDEX OF THE ELEMENTS

1. Fastening Means
2. Ventilation Fan
3. SPDT Switch
4. Top Screw
4a. Washer
5. Top
6. Top Opening
7. Camera
8. Body
9. Bottom Opening
10. Device
11. Ventilation Area
12. Lighting Source
13. Lighting Source Bracket
14. Bracket Screws
15. Port
16. Inlet
18. Cap
19. Notch
20. Air System
20b. Ventilation Area
21. Detection Chamber Bracket
22. Bracket Screw
23. Bracket Washer
24. Top Opening
25. Rectangular-shaped Opening
26. Middle Alignment Screw
27. Side Support Screw
28. Cap Align Screw
30. Detection Chamber
31. Chamber Body
32. Chamber Top
33. Wire Mesh Disc
35. Trained Organism
40. Power Source
60. Housing

We claim:

1. A computer vision chemical detection device for detecting a presence of at least one chemical during a chemical detection process, the device comprising:
    at least one organism to detect the at least one chemical,
    a detection chamber enveloping the at least one organism, the detection chamber being structured so that an individual operator can carry the detection chamber from one area of investigation to a subsequent area of investigation;
    a region of interest within the detection chamber, the region of interest being structured so that the at least one organism can relocate and ambulate into and out of the region of interest during a chemical detection process; and,
    a sensor positioned to detect the a presence or absence of the at least one organism in the region of interest and notify the operator of a presence of the at least one chemical.

2. The device of claim 1 wherein the sensor is a camera.

3. The device of claim 1 wherein the device detects the at least one chemical based on a location of the at least one organism relative to the region of interest.

4. The device of claim 2 wherein the camera is positioned to communicate a population density of the at least one organism present in the region of interest.

5. The device of claim 2 wherein the camera is positioned to detect and communicate data regarding crowding behavior of the at least one organism in the region of interest.

6. The device of claim 2 wherein the camera is positioned to detect and communicate data regarding area-restricted searching behavior of the at least one organism in the region of interest.

7. The device of claim 2 wherein the region of interest is defined by and co-located with a gas inlet portion of the detection chamber.

8. The device of claim 1 further comprising a user interface communicating with the sensor.

9. The device of claim 8 wherein the user interface is a laptop computer.

10. The device of claim 1 wherein the at least one organism is at least one invertebrate.

11. The device of claim 10 wherein the at least one invertebrate is at least one wasp.

12. The device of claim 1 wherein the at least one organism is selected from a group consisting of wasps, bees, moths, butterflies, beetles, assassin bugs, spiders, mites, ticks, scorpions, crayfish, lobsters, crabs snails, slugs, squids, and clams.

13. The device of claim 1 wherein the organism is trained to detect the at least one chemical.

14. A computer vision system for detecting a presence of at least one chemical, the system comprising:
    at least one organism for detecting a presence of at least one chemical;
    a detection chamber enclosing the at least one organism, the detection chamber being structured so that an individual user can carry the detection chamber from one area of investigation to a subsequent area of investigation;
    a region of interest within the detection chamber, the detection chamber and the region of interest being structured so that the at least one organism is capable of ambulating and relocating into and out of the region of interest during a chemical detection process;
    a camera positioned so that the region of interest is within a field of vision of the camera;
    a user interface in communication with the camera;
    an elongate housing at least partially enclosing the camera and the detection chamber; and
    a fan directing a gas into the elongate housing and through the detection chamber, the camera communicating a presence or absence of the at least one organism in the detection chamber region of interest to the user interface, the user interface notifying a user of a presence or absence of the at least one chemical in the gas.

15. The system of claim 14 wherein the device detects the at least one chemical based on a location of the at least one organism relative to the region of interest.

16. The system of claim 14 wherein the region of interest is defined by location of a detection chamber gas inlet.

17. A method of detecting a presence of at least one chemical, the method comprising the steps of:
- providing at least one organism for detecting a presence of at least one chemical;
- depositing the least one organism in a detection chamber, wherein the detection chamber is structured so that an individual user can carry the detection chamber from one area of investigation to a subsequent area of investigation;
- identifying a region of interest within the detection chamber, the detection chamber and the region of interest being structured so that the at least one organism is capable of ambulating and relocating into and out of the region of interest during a chemical detection process;
- positioning a camera so that the region of interest is within a field of vision of the camera;
- connecting a user interface to the camera;
- placing the camera and the detection chamber in an elongate housing;
- directing a gas into the elongate housing and through the detection chamber;
- activating the camera to observe a presence or absence of the at least one organism in the region of interest;
- enabling the user interface to analyze observations of the camera so that the user interface notifies a user of a presence of the at least one chemical in the gas based on a presence or absence of the at least one organism in the region of interest.

18. The method of claim 17 further comprising purging the detection chamber with clean air and replacing the at least one organism after 48 hours.

* * * * *